(12) United States Patent
Myers et al.

(10) Patent No.: US 6,639,125 B1
(45) Date of Patent: *Oct. 28, 2003

(54) DULL1 CODING FOR A STARCH SYNTHASE AND USES THEREOF

(75) Inventors: Alan M. Myers, Ames, IA (US); Martha Graham James, Des Moines, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/554,467

(22) PCT Filed: Nov. 12, 1998

(86) PCT No.: PCT/US98/24225
§ 371 (c)(1),
(2), (4) Date: May 12, 2000

(87) PCT Pub. No.: WO99/24575
PCT Pub. Date: May 20, 1999

Related U.S. Application Data

(63) Continuation-in-part of application No. 08/968,542, filed on Nov. 12, 1997, now Pat. No. 5,981,728.

(51) Int. Cl.⁷ .................. C12N 15/29; C12N 15/62; C12N 15/82; A01H 5/00; C12P 19/04
(52) U.S. Cl. ............. 800/284; 800/278; 435/69.1; 435/69.7; 435/101; 435/320.1; 435/419; 435/468; 536/23.6
(58) Field of Search .............. 536/23.6; 435/69.1, 435/320.1, 101, 419, 468, 69.7; 800/278, 284

(56) References Cited

U.S. PATENT DOCUMENTS 5,981,728 A * 11/1999 Myers et al. .............. 536/23.6
6,130,367 A * 10/2000 Kossmann et al. ......... 800/284

FOREIGN PATENT DOCUMENTS

| DE | 44 41 408 | * | 5/1996 |
| EP | 779 363 | * | 6/1997 |
| WO | WO 96/15248 | * | 5/1996 |

OTHER PUBLICATIONS

Accession No. AAQ87587, Dobutsuyo Seibutsugakuteki Seeizai Kyokai, Dec. 1995.*
Kossman et al. Progress in Biotechnol. 10:271–278, 1995.*
Nakatami et al. Jpn. J. Crop Sci. 61(3):463–468, 1992.*
Baba et al. Plant Physiol. 103:565–573, 1993.*
Mu, C. et al., "Association of a 76 KDA Polypeptide with Soluble Starch Synthase I Activity in Maize (CV B73) Endosperm," Plant Journal, Blackwell Scientific Publications, Oxford, GB, vol. 6, No. 2, pp. 151–159 (1994).
Gao, M. et al., "Characterization of dull1, a maize gene coding for a novel starch synthase," The Plant Cell, vol. 10, pp. 399–412 (Mar. 1998).
Boyer, C. et al., "Evidence for independent genetic control of the multiple forms of maize endosperm branching enzymes and starch synthases," Plant Physiology, vol. 67, pp. 1141–1145 (1981).
Dang, P.L. et al., "Maize leaf and kernel starch synthases and starch branching enzymes," Phytochemistry, vol. 27, No. 5, pp. 1255–1259 (1988).
Ozbun, J.L. et al., "Adenosine diphosphoglucose–starch glucosyltransferases from developing kernels of waxy maize," Plant Physiology, vol. 48, pp. 765–769 (1971).
Marshall, J. et al., "Identification of the Major Starch Synthase in the Soluble Fraction of Potato Tubers," Plant Cell, American Society of Plant Physiologists, Rockville, MD, US, vol. 8, No. 7, pp. 1121–1135 (Jul. 1, 1996).
Marjori A. Matzke et al., "How and Why do Plants Inactivate Homologous (Trans)genes?¹", Plant Physiology, 107:679–685 (1985).
Carolyn Napoli et al., "Introduction of Chimeric Chalcone Synthase Gene into Petunia Results in Reversible Co–Suppression of Homologous Genes in trans", The Plant Cell, 2:279–289 (1990).

* cited by examiner

Primary Examiner—David T. Fox
(74) Attorney, Agent, or Firm—Weingarten, Schurgin, Gagnebin & Lebovici LLP

(57) ABSTRACT

The maize gene dull1 (du1) of the present invention is a determinant of the structure of endosperm starch. Mutations of du1 affect the activity of at least two enzymes involved in starch biosynthesis, namely the starch synthase, SSII, and the starch branching enzyme, SBEIIa. Du1 codes for a predicted 1674 residue protein, and is expressed with a unique temporal pattern in endosperm but is undetectable in leaf or root. The size of the Du1 product and its expression pattern match precisely the known characteristics of maize SSII. The Du1 product contains two different repeated regions in its unique amino terminus, one of which is identical to a conserved segment of the starch debranching enzymes. The cDNA provided for in the present invention encodes SSII, and mutations within this gene affect multiple aspects of starch biogenesis by disrupting an enzme complex containing starch synthase(s), starch branching enzyme(s), and possibly starch debranching enzyme.

9 Claims, 19 Drawing Sheets

```
                    MEMVLRSQSPLCLRSGPVLIFRPTVAGGGG                              30

DU1   GTQSLLRTTRFARRRVIRCVVASPGCPNRKSRTASPNVKVAAYSNYAPRLLVESSSKKS               89

DU1   EHHDSSRHREETIDTYNGLSGSDAAELTSNRDVEIEVDLQHISEEELPGKVSINASLGE               148

DU1   METVDEAEVEEDKFEVDTSGIVLRNVAVREVDPKDEHNAKDVFVVDSSGTAPDNAAVEE               207

DU1   VVDEAEVEEDMVDVDILGLDLNNATIEEIDLMEEALLENFDVDSPGNASSGRTYGGVDE               266

DU1   LGELPSTSVDCIAINGKRRSLKPKPLPIVRFQEEQIVLSIVDEEGLIASSCEEGQPVV                325

DU1   DYDKQEENSTAFDEQKQLTDDFPEEGISIVHFPEPNNDIVGSSKFLEQKQELDGSYKQD               384

DU1   RSTTGLHEQDQSVVSSHGQDKSIVGVPQQIQYNDQSIAGSHRQDQSIAGAPEQIQSVAG               443

DU1   YIKPNQSIVGSCKQHELIIPEPKKIES[T]ISYNEIDQSIVG[S]HKQDK[S]VVSVPEQIQSIV         502
SS3                              MDVPFFPLHRSLSCTSVSNAITHLK[I]KPILGFVSHGTT[S]LSVQS[S]SWRKDGMVTGVS  56

DU1   SHSKF[NQS]TVDSYRQAESIIGVPEKVQSITSYDKLDQSIVGSLK[Q]DEPIISVPEKIQSI           561
SS3   FSICA[NFS]GRRRRKVSTPRSQGSSPKGFVPRKPSGMSTQRKVQK[S]NGDKESKSTSTSKE           115

DU1

```
DU1  EQKSIAMNEEQTIVTEEDIPMAKVEIGIDKAKFLFLLSFEESSWDFNEVGIIEADFQYF   738
SS3  VEPQQLKENNAGNWEYKGPVASKLLEITKASDVEHTESNEIDDLDTNSFFKSDLIEEDE   292

DU1  VDETSMSTEQFIQESPNDDLDPQALWSMLQEIAEKNYSIGNKLFTYPDVL-KADSTIDLY   797
SS3  PLAAGTVETCDSSLNLRLEMEANLRRQAIERLAENLLQCIRLCFDEWKPEDVEIF      351

DU1  FNRDLSAVANEPDVLIKGAFNGWKWRFFFTEKLHKSELAGDWWCKLYIPKQAYRMDFVF   856
SS3  LNRGLSTLKNESDVLIMGAFNEWRYSEITRLTETHLNGDWMSCKIHVPKEAYRADFVF   410

DU1  FNGHTVYFNNNDFVIQIESTMDENLFEDFLAEKQRELENLANEEAERRRQTDEQRR      915
SS3  FNGQDVYDNNDGNDFSITVKGGMQIIDFENFLEEKWREQEKLAKEQAERERLAEEQRR    469

DU1  MEEERAADKADRVQAKVEVETKKKNKLCNVLGIARAPVDNLWYIEPITTGQFATVRLYYN  974
SS3  IEAEKAEIEADRAQAKEAAKKKKVLRELMVKATKTRDITWYIEPSEFKCEDKVRLYYN   528

DU1  INSRPLMHSTEIMHGGYNNWIDGLSFAERLVHHDKDCDWWFADVVVPERTYVLDWVF    1033
SS3  KSSGPLSHAKDIMIHGGYNNWKDGLSIVKKLVKSERIDGDWWYTEVVIPDQALFLDWVF  587

DU1  ADGPPGSARNYDNNGGHDFHATLPNNMTEEFYMEEQRIYTRLQQERRREFAIKRKA    1092
SS3  ADGPPKHAIAYDNNHRODFHAISOKHVVXTEPIJOAGSSVTWYNPANTVLNGKPEIWER  646

DU1  ERNAKMKAEMKEKTMRFLMSOKHIVYTEPLEIHAGTIDMLYNPSNTVLHGKPEVWFR   1151
SS3  EKTOLLKIHEIKERITMKSELISOKHVVXTEPLIJOAGSSVTWYNPANTVLNGKPEIWFR 705

DU1  CSFNRWMYPGMLPPQKMVQAENGSILKATVYVPRDAYMMDFVFSESEEGGIYDNRNGL  1210
SS3  CSFNRWTHRLGPLPPOKMSPAENGTHVRATVKVPLDAYMMDFVFSEREDGGIFDNKSGM  764

DU1  DYHIPVFGSIAKEPPMHIVHIAVEMAPIAKVGGLGDVVTSLSRAVQDLGHNVEVILPKY  1269
SS3  DYHIPVFGGVAKEPPMHIVHIAVEMAPIAKVGGLGDVVTSLSRAVQDLNHNVDILPKY   823

DU1  GCINLSNVKNLQIFOSFSWGGSEINWRGLVEGLQVYFLEPQNGMFGVGMVYG RDDR   1328
SS3  DCLKMNNVKDFRFIKNYFWGGTELKUWFGKVEGLSVYFLEPONGIFSKGJVYGCSNDGE  882
```

FIGURE 6A-2

```
DU1  RFGFFCRSALEFLLQGSSFNIIHCHDWSSAPVAWLHKENYAKSSLANARMVFTIHNLE  1387
SS3  RFGFFCHAALEFLLQGFSPDIIHCHDWSSAPVAWLFKEQYTHYGLSKSRIVFTIHNLE   941

DU1  FGAHHIGKAMRYCDKATTVSNTYSKEVSGHGAIMPHIGKFYGILNGIDPPIWDPYNDF  1446
SS3  FGADLIGRAMTNADKATTVSPTYSQEVSGNPVIAPHIHKFHGIVNGIDPPIWDELNDKF 1000

DU1  IPMHYTCENVVEGKRAAKRALQKFGLQQIDMPMVGIVTRLTAQKGIHLIKHAHRTLE   1505
SS3  IPIPYISENVVEGKTRAAKFALQFKIGIKQADIPLVGIIITRLTHQKGIHLIKHAWRTLE 1059

DU1  RNGQVVLLGSAPDQRIIQADFVNLANILHGVNHGQVRISLTYDEPLSHLIYAGSDFILVP 1564
SS3  RNGQVVLLGSAPDHRMQNNFVNLANQLHSKYNDRARICLTYDEPLSHLIYAGADFILVP 1118

DU1  SIFEPCGLTQLVAMRYGIIPIVRKTGGLFDTVFDVDNKERARDRGLEPNGFSFDGADS  1623
SS3  SIFEPCGLTQLTAMRYGSIPMDTVFDVDHDKERAQQCGLEPNGFSFDGADA        1177

DU1  NGVDYALNRAISAWFDARSWFHSLCKRVMEQDWSNRPALDYIELYRSASKL         1674
SS3  GVDYALNRAISAWMDRIMFNSLCKDVMEQDWSNRPALDYELYHAARKLE          1230

DU1  (SEQ ID NO: 12)

SS3  (SEQ ID NO: 35)
```

FIGURE 6A-3

SBE-repeats in DU1:

| Start | Sequence | | End | SEQ ID |
|---|---|---|---|---|
| 478 | DQSIVG | SHKQ | 487 | (SEQ ID NO: 16) |
| 538 | DQSIVG | SLKQ | 547 | (SEQ ID NO: 17) |

↑ 6/6 match

| 448 | NQSIVG | SCKQ | 457 | (SEQ ID NO: 18) |
| 568 | NQSIVG | LPKQ | 577 | (SEQ ID NO: 19) |
| 418 | DQSIAG | SHRQ | 427 | (SEQ ID NO: 20) |
| 428 | DQSIAG | APEQ | 437 | (SEQ ID NO: 21) |
| 404 | DKSIVG | VPQQ | 413 | (SEQ ID NO: 22) |
| 598 | DLSIVG | NEFQ | 607 | (SEQ ID NO: 23) |

↑ 5/6 match

ETVDEAEVEEDK--FEVDTSGIVLRNVAVR (SEQ ID NO: 32)
E-VDPKDEHNAKDVFVVDSSGTAPDNAAVE (SEQ ID NO: 33)
EVVDEAEVEEDM--VDVDILGLDLNNATI (SEQ ID NO: 34)

DULL1 CODING FOR A STARCH SYNTHASE AND USES THEREOF

This application is a U.S. national phase entry of PCT/US98/24225, filed Nov. 12, 1998, which is a continuation-in-part of U.S. patent application Ser. No. 08/968,542, filed Nov. 12, 1997, now U.S. Pat. No. 5,981,728, the whole of which is hereby incorporated by reference herein.

FEDERAL FUNDING LEGEND

This invention was produced in part using funds under USDA Grant number 96-35300-3779. Consequently, the federal government has certain rights in this invention.

BACKGROUND OF THE INVENTION

1. Field of the Invention

The present invention relates generally to carbohydrate biochemistry. More specifically, the invention relates to starch biosynthesis and the enzyme(s) involved.

2. Description of the Related Art

Starch, the most significant carbohydrate reserve in plant storage tissues, comprises the glucose homopolymers amylose and amylopectin. Amylose consists of predominantly linear chains of α-(1→4)-linked glucose residues, whereas amylopectin is a highly branched glucan with a specific "clustered" distribution of α-(1→6) glycosidic bonds (i.e. branch linkages) connecting linear chains (French, 1984; Manners, 1989).

Despite the relatively simple chemical structure of amylopectin, very little is known about the enzymatic processes responsible for formation of the highly specific and complex branching patterns in this polysaccharide. Biosynthesis of amylose and amylopectin involves activities of four groups of enzymes, each of which comprises multiple isozymes. These enzymes are ADPG pyrophosphorylases (AGPase), starch synthases (SS), starch branching enzymes (SBE) and starch debranching enzymes (SDBE) (Preiss, 1991; Hannah et al., 1993; Martin and Smith, 1995; Nelson and Pan, 1995; Ball et al., 1996; Preiss and Sivak, 1996; Smith et al., 1996). These enzymatic steps can account for all chemical linkages in starch, however, the specific roles of individual isozymes in formation of specific branching patterns in amylopectin and determination of starch granule structure and properties remain unknown.

Analysis of maize mutants with abnormal endosperm phenotypes has contributed greatly to the understanding of starch synthesis (Shannon and Garwood, 1984; Nelson and Pan, 1995) and facilitated the identification of many genes coding for starch biosynthetic enzymes. Cloned genes whose products are thought to be involved directly in starch biosynthesis are waxy (wx), coding for the granule-bound starch synthase GBSSI (Shure et al., 1983; Klosgen et al., 1986), amylose extender (ae), coding for SBEIIb (Fisher et al., 1993; Stinard et al., 1993), shrunken2 (sh2) and brittle2 (bt2), coding for the large and small subunits of AGPase, respectively (Bae et al., 1990; Bhave et al., 1990), and sugary1 (su1), coding for the SDBE SU1 (James et al., 1995). The transposon-tagging strategy was used to determine that the abnormal endosperm phenotype of wx-, ae-, or su1-mutants results from primary defects in GBSSI, SBEIIb, or SU1, respectively, and this approach remains the most effective way to identify genes such as dull1 (du1), in which the primary defect can not be associated with a particular enzyme deficiency.

The du1-mutations define a gene with a very important function in starch synthesis, as indicated by extensive structural analyses of starch from du1-mutant endosperms, and by the effects of these mutations when combined with other genetic deficiencies in starch biosynthetic enzymes (Shannon and Garwood, 1984; Nelson and Pan, 1995). The reference mutation du1-Ref was first identified as a recessive modifier of su1-Ref and su1-amylaceous (su1-am) (Mangelsdorf, 1947). Mutations of du1, when homozygous in otherwise non-mutant backgrounds, result in mature kernels with a tarnished, glassy, and somewhat dull appearance referred to as the "dull phenotype". Expression of this phenotype, however, depends on the particular genetic background (Mangelsdorf, 1947; Davis et al., 1955). Total carbohydrate and starch content in mature du1- mutant kernels is slightly lower than normal (Creech, 1965; Creech and McArdle, 1966). The apparent amylose content in starch from du1-mutants is slightly or greatly elevated compared to normal depending on the genetic background (Shannon and Garwood, 1984), although the properties of polysaccharides in the apparent amylose fraction are essentially not altered (Dvonch et al., 1951). Approximately 15% of the starch in du1-mutant endosperms is in a form known as "intermediate material", which is distinguished from amylose and amylopectin by the properties of its starch-iodine complex (Wang et al., 1993b). Analysis of combined amylopectin/intermediate material fractions indicated that starch from du1-mutants has the highest degree of branching among a wide variety of normal and mutant kernels analyzed (Inouchi et al., 1987; Wang et al., 1993a; Wang et al., 1993b). Starch granules from du1-mutants seem to have normal structural and physical properties, although some abnormally shaped granules are found in the mutant endosperm (Shannon and Garwood, 1984).

Despite these subtle effects exerted by the single mutation, du1-alleles when combined with other mutations affecting starch synthesis result in a broad range of more severe alterations (Shannon and Garwood, 1984; Nelson and Pan, 1995). Mutations of du1 have been examined in combination with wx-, ae-, su1-, and sugary2 (su2-) mutations, and in all instances the double mutant kernels contained more soluble sugars and less total starch than when any of the mutations was present alone. In many instances the double mutants also produce polysaccharide forms that are distinct from the starch found in any single mutant kernels. These pleiotropic effects indicate the product of Du1 affects many aspects of starch biosynthesis in maize endosperm, however, without knowing the identity of this protein it is difficult to assess its specific functions.

Consistent with the pleiotropic genetic effects, du1-mutations cause reduced activity in endosperm of two seemingly unrelated starch biosynthetic enzymes, the starch synthase SSII and the branching enzyme SBEIIa (Boyer and Preiss, 1981). SSII is one of two enzymatically distinct starch synthase activities identified in the soluble fraction of maize endosperm; in vitro activity of SSII requires an exogenous glucan primer, and its molecular weight was determined in different studies as either 95 kD or 180 kD (Boyer and Preiss, 1981; Mu et al., 1994). Similarly, SBEIIa is one of the three known SBE isozymes in endosperm cells (Boyer and Preiss, 1978b; Fisher et al., 1993; Fisher et al., 1995; Gao et al., 1997). Several possibilities exist to explain the dual biochemical effects of du1-mutations. Du1 may code for a protein regulating the expression or activity of both SSII and SBEIIa. Alternatively, Du1 may code for either of these two enzymes, and the deficiency in one enzyme might also affect the second enzyme because of a direct or substrate-mediated physical interaction.

DU1 codes for a starch synthase, as indicated by the extensive similarity of its deduced amino acid sequence to potato SSIII, and by the substantial similarity between the C-terminal residues of DU1 and a large group of phylogenetically diverse starch- and glycogen synthases. Particularly striking are two regions that together comprise more than half of the deduced DU1 sequence of 1,674 residues, which share very high similarity of 51% and 73%, respectively, with the corresponding regions of the potato SSIII sequence. Within a stretch of 450 amino acids at the C-terminus of DU1 nearly 30% of the best aligned residues are identical in comparisons to a wide variety of starch- and glycogen synthases, suggesting the location of a domain within DU1 that provides α-1,4-glycosyltransferase activity.

The starch synthase coded for by Du1 is the soluble isozyme identified biochemically as SSII (Ozbun et al., 1971; Boyer and Preiss, 1981). The deduced molecular weight of DU1 including a potential transit peptide, 188 kD, matches closely with that of 180 kD reported for mature SSII lacking a transit peptide (Mu et al., 1994). The size difference of approximate 8 kD may be due to the transit peptide present in the deduced DU1 sequence. The tissue specific expression pattern of the Du1 mRNA also matches the expression pattern of SSII. Du1 transcripts were undetectable in leaves either by RNA gel blot or RT-PCR analyses, corresponding with that fact no detectable SSII activity was present in leaf extracts (Dang and Boyer, 1988). Moreover, the activity of SSII, along with that of SBEIIa, was greatly reduced in du1-mutant endosperm (Boyer and Preiss, 1981). Therefore, it appears that the maize du1 locus codes for the soluble starch synthase SSII, the counterpart of potato SSIII.

This characterization of DU1 implies that the phenotypic effects of du1-mutations, including changes in starch structure, deficiencies of two starch biosynthetic enzymes, and genetic interactions with ae-, su1-, su2-, and wx-mutations, all result either directly or indirectly from alteration of SSII. The reduction of SBEIIa activity in du1-mutant endosperm could result from the SSII deficiency owing to physical interaction between the two enzymes. A direct physical association of SSII and SBEIIa is implied by the observation that peak activities of both SSII and SBEIIa always coincide in the same DEAE-cellulose column fractions (Boyer and Preiss, 1978a; Boyer and Preiss, 1981; Dang and Boyer, 1988). Thus, SSII and SBEIIa may function together in vivo in the form of single multi-enzyme complex. Loss of the intact enzyme complex owing to reduction of SSII in du1-mutant endosperm may result in abnormally rapid proteolytic turnover of SBEIIa, or prevent accumulation of the enzyme by some other mechanism. Alternatively, expression of the Sbe2a gene in du1-mutant endosperm may be inhibited as a more indirect consequence of the deficiency in SSII, for example through reduction of a transcriptional inducer or elevation of a repressor. Although the du1-Ref mutation does indirectly affect expression of other starch biosynthetic genes (Giroux et al., 1994), it actually caused increased gene expression rather than the reduction observed for SBEIIa. Furthermore, considering that large glucose polymers are expected to be the substrate and product of DU1, down-regulation of Sbe2b expression by a transcriptional mechanism seems unlikely. Thus, the former hypothesis may explain the deficiency of SBEIIa in du1-mutant endosperm.

The broad impact of the combination of du1-mutations with various su1-alleles on kernel phenotype and starch synthesis (Cameron, 1947; Shannon and Garwood, 1984) could be explained by the SU1 SDBE also interacting closely with SSII in vivo, perhaps in the same enzyme complex with SBEIIa. This proposed association of SBEIIa and SU1 in a multi-enzyme complex is consistent with the proposed simultaneous branching and debranching actions during amylopectin synthesis by SBE and SDBE (James et al., 1995; Nelson and Pan, 1995; Ball et al., 1996).

Thus, the prior art is deficient in understanding the complex association of enzymes involved in starch synthesis and in cloning genes corresponding to these enzymes. The present invention fulfills this long-standing need and desire in the art.

SUMMARY OF THE INVENTION

To illustrate the role of the du1locus in starch biosynthesis, a transposon-tagging strategy was used to isolate the gene and describe its polypeptide product. The present invention reports tagging of the du1 locus with a Mutator (Mu) transposon, cloning and characterization of a portion of the gene, and the sequence of a near full-length cDNA (SEQ ID No. 1). The amino acid sequence deduced from this cDNA indicates Du1 codes for a 186 kD polypeptide extremely similar to SSIII, a starch synthase from potato tubers (Abel et al., 1996; Marshall et al., 1996). The expression pattern of Du1 also was characterized. Taken together these characterizations indicate that Du1 most likely codes for SSII of maize endosperm. In addition, the product of Du1 contains unique sequence features in its amino terminus that may mediate direct interactions with other starch biosynthetic enzymes.

One object of the present invention is to provide an enzyme with which to regulate the production of starch, and with which to produce altered or novel forms of starch.

In an embodiment of the present invention, there is provided a cDNA corresponding to the dull1 gene of maize.

In yet another embodiment of the present invention, there is provided an expression vector containing the sequence of dull1 with which to produce the starch synthase enzyme in transgenic plants or other prokaryotic or eukaryotic organism.

In yet another embodiment of the present invention, there is provided (1) cDNA having the nucleotide sequence comprising nt 120 to nt 1221 of SEQ ID No. 1, said sequence encoding the first 368 amino acids of DU1; (2) cDNA having the nucleotide sequence comprising nt 655 to nt 1221 of SEQ ID No. 1, said sequence encoding amino acids 180 to 368 of DU1; (3) cDNA having the nucleotide sequence comprising nt 565 to nt 816 of SEQ ID No. 1, said sequence encoding amino acids 150 to 233 of DU1; (4) cDNA having the nucleotide sequence comprising nt 1369 to nt 1944 of SEQ ID No. 1, said sequence encoding amino acids 418 to 609 of DU1; (5) cDNA having the nucleotide sequence comprising nt 1 to nt 1437 of SEQ ID No. 1, said sequence encoding amino acids 1 to 440 of DU1; (6) cDNA having the nucleotide sequence comprising nt 1438 to nt 2424 of SEQ ID No. 1, said sequence encoding amino acids 441 to 769 of DU1; (7) cDNA having the nucleotide sequence comprising nt 2425 to nt 3791 of SEQ ID No. 1, said sequence encoding amino acids 769 to 1225 of DU1

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail.

These drawings form a part of the specification. It is to be noted, however, that the appended drawings illustrate preferred embodiments of the invention and should not be considered to limit the scope of the invention.

FIG. 1A shows the crossing scheme. The specific maize lines used in this procedure are listed below. The allele designation " du1-M" indicates a putative recessive mutation in the du1 locus caused by insertion of a Mu transposon. FIG. 1B shows the dull mutant phenotype. The ear shown was obtained by self-pollination of a du1-R2370::Mu1/Du1 heterozygote. Dull kernels and wild type kernels are present at approximately the Mendelian frequency of 1:3, respectively.

FIG. 2A shows detection of Mu1-containing genomic DNA fragments. BamHI-digested genomic DNA of seedlings grown from segregating (1:1) non-mutant and dull sibling kernels was separated on a 1% agarose gel, blotted, and probed with the 960 bp internal MluI fragment of Mu1 excised from plasmid pMJ9 (Barker et al., 1984). FIG. 2B shows the structure of the cloned 2.0-kb BamHI fragment. The hatched bar indicates the position of Mu1 as revealed by the nucleotide sequence of the cloned fragment. The position of the 500 bp probe fragment F500 is indicated, and the figure is drawn to scale. Restriction sites are indicated for BamHI (B) and NotI (N). FIG. 2C shows detection in genomic DNA of restriction fragments homologous to the cloned fragment. The analysis is the same as that shown in FIG. 2A, except that the blot was hybridized with a single-stranded probe generated by PCR using fragment F500 shown in FIG. 2B as the template.

FIG. 3A shows the identification of genomic fragments containing regions flanking the Mu1 element in the cloned 2.0 kb BamHI fragment. EcoRI- and XbaI-digested genomic DNA from du1-R2370::Mu1/du1-Ref mutants and sibling Du1/du1-Ref non-mutant seedlings was probed with fragment F500. FIG. 3B shows an illustration of the procedure for cloning the near full-length Du1 cDNA. Genomic fragment BE1300 was cloned by nested-primer PCR as detailed below. The wild type counterpart of the original cloned BamHI fragment (indicated by crosshatched boxes) was shown to be part of a 6.0 kb EcoRI fragment in FIG. 3A. A population of EcoRI genomic fragments of about 6.0 kb was ligated to pBluescript SK+(dashed lines). The ligation mixture was used to amplify a 2.0 kb fragment by primers du1-sp1 and T3. Fragment BE1300 was then amplified from the 2.0 kb fragment by primers du1-sp4 and T3. The position of the Mu1 insertion in du1-R2370::Mu1 is indicated by the asterisk. The positions of PCR primers used for fragment amplification are indicated. Restriction sites are indicated for EcoRI (E) and BamHI (B). The near full-length cDNA diagram represents the continuous sequence from the three overlapping cDNA fragments. The solid arrow indicates the location and 5'-3' direction of the Du1 coding sequence. The partial intron-exon structure was deduced by comparing the available genomic sequence to the cDNA sequence.

FIG. 5A shows the RNA gel blot analysis of total RNAs from developing endosperm. Total RNAs extracted from endosperm of W64A kernels harvested at various developmental ages, and from du1-Ref and du1-R2370::Mu1 mutant kernels havested at 20 DAP, were fractionated on a formaldehyde-agarose gel, blotted, and probed by the cDNA insert in pMg6Aa. Minor loading differences were calibrated by hybridization of the 26S rRNA on the same blot, stripped of the cDNA probe, to a tomato rRNA cDNA probe. Transcript size was estimated using a RNA size standard (GibcoBRL). FIG. 5B shows the relative steady state level of the Du1 transcript in developing endosperm. Radioactivity of transcripts hybridized to the Du1 cDNA probe was analyzed using a Phosphorimager, quantified using the program ImageQuant, and expressed as the percentage of the maximal signal strength on the same blot (Relative Level) after calibration of minor loading difference. The data represent the average of three repeats of the analysis with standard error less than 10%. FIG. 5C shows the RT-PCR analysis. DNA fragments amplified from total RNAs by RT-PCR using primers du1-F3 and du1-R1 were separated in an agarose gel and visualized by ethidium bromide staining. Endosperm (En) and embryo (Em) RNAs were from tissue collected 22 DAP. The lane designated "-control" is from the same sample as the En lane, except that the RNA was pretreated with RNAase A prior to amplification. RNAs from the indicated du1-mutants were obtained from endosperm collected 22 DAP.

FIGS. 6A–6B shows the DU1 amino acid sequence is most similar to that of potato SSIII. FIG. 6A shows the primary sequence alignment. The deduced amino acid sequences of DU1 and potato SSIII (GenBank accession number X95759) are aligned. Solid directional arrows indicate the positions of the three 60 amino acid SBE-superrepeats, and dotted arrows denote individual copies of the SBE-repeat. Dashed arrows indicate the positions of the three repeat units that make up the 85 residue repeat. Double-headed arrows labeled with Roman numerals indicate the positions of correspondingly designated conserved sequence blocks identified in the glucan synthase family (Preiss and Sivak, 1996). FIG. 6B shows the domains of DU1. Similarity scores between each segment of DU1 and SSIII are shown under each region. "Catalytic domain" indicates the region of DU1 similar in amino acid sequence to α-(1→4)-glycosyltransferases in general. "SSIII/DU1 homology domain" indicates the region shared specifically by DU1 and SSIII among known proteins. "DU1-specific region" indicates the portion of DU1 that is unique in amino acid sequence among know proteins.

FIGS. 7A–7C show the repeats in the unique DU1 amino terminus. FIG. 7A shows the alignment of the SBE-superrepeats. Numbers refer to positions of residues within the DU1 coding sequence. Each 60 residue SBE-superrepeats comprises six copies of the 10 amino acid SBE-repeat unit (indicated by arrows). The degree of sequence conservation between each SBE-repeat descends toward the C-terminus of each SBE-superrepeat. FIG. 7B shows the alignment of selected copies of the SBE-repeat and conservation of the M-box within branching enzymes. In the first grouping numbers refer to position within the DU1 coding sequence. Boxed residues are identical to the consensus sequence of the SBE-repeat. Arrows indicate the M-box sequence (DQSIVG). The M-box sequence is almost completely conserved in the members of SBEI family, including maize SBEI (GenBank accession no. D11081), pea SBEII (GenBank accession no. X80010), wheat SBEI (GenBank accession no. Y12320). The M-box sequence is also well conserved, with substitution Of two residues of similar properties, in members of the SBEII family and glycogen synthases, including maize SBEIIa (Gao et al., 1997), maize SBEIIb (GenBank accession no. L08065), pea SBEI (GenBank accession no. X80009), glycogen synthase from human liver (GenBank accession no. D29685) and *S. cerevisiae* glycogen synthase (the GLC3 product; GenBank accession no. M76739). Residue numbers refer to the first enzyme in each group. Arrows indicate the occurrence of M-box sequences or related sequences. Asterisks indicate conserved residues that in amylolytic enzymes of determined structure are known to be part of the active site. FIG. 7C shows the sequence conservation of the 28 amino acid repeat. The three repeats within the 85 residue repeat region were best aligned to show the pattern of sequence conservation among the two portions of the 28 residue basic repeating unit. Numbers refer to positions within the DU1 coding sequence.

FIG. 9A: Total soluble extracts from 20 DAP kernels of the W64A genetic background homozygous for the indicated allele were fractionated by SDS-PAGE and probed with anti-DU1N or anti-SSI. An equal amount of protein was loaded in each lane. "du1-M5" indicates the allele du1-R4059. The asterisk indicates full length DU1. FIG. 9B: Extracts of nonmutant W64A kernels and congenic du1-Ref mutant kernels collected 20 DAP were separated into granule (i.e., 10000×g pellet) and total soluble fractions (i.e., 10000×g supernatant). Equal volumes of each fraction were separated by SDS-PAGE, so that each pair of lanes is standardized to kernel fresh weight. The samples were probed with anti-DU1N or anti-SSI, as indicated. FIG. 9C: Total soluble extracts of W64A kernels harvested at various times after pollination, as indicated, were analyzed by SDS-PAGE and immunoblot analysis using anti-DU1. N or anti-SSI.

FIG. 11A: SS activity zymogram. Proteins in total soluble endosperm extracts were separated based on molecular weight by SDS-PAGE and then allowed to renature in the gel. SS substrates were provided to the entire gel, and positions of glucan synthesis were detected by staining with iodine. Two congenic strains in the W64A genetic background were analyzed, one bearing the nonmutant allele Du1 and the other containing du1-Ref (indicates as "du1-"). Two SS activities are evident in the nonmutant endosperm, one of which is missing from the du1-Ref extract. FIG. 11B: Immunoblot analysis. Proteins in duplicates of the gel shown in panel a were transferred to nitrocellulose paper and probed with the indicated antiserum. A polypeptide of the same mobility and genetic specificity as the larger SS activity is recognized by anti-DU1N, whereas a protein of the same mobility as the smaller SS activity is recognized by anti-SSI.

DETAILED DESCRIPTION OF THE INVENTION

Figure 1A:
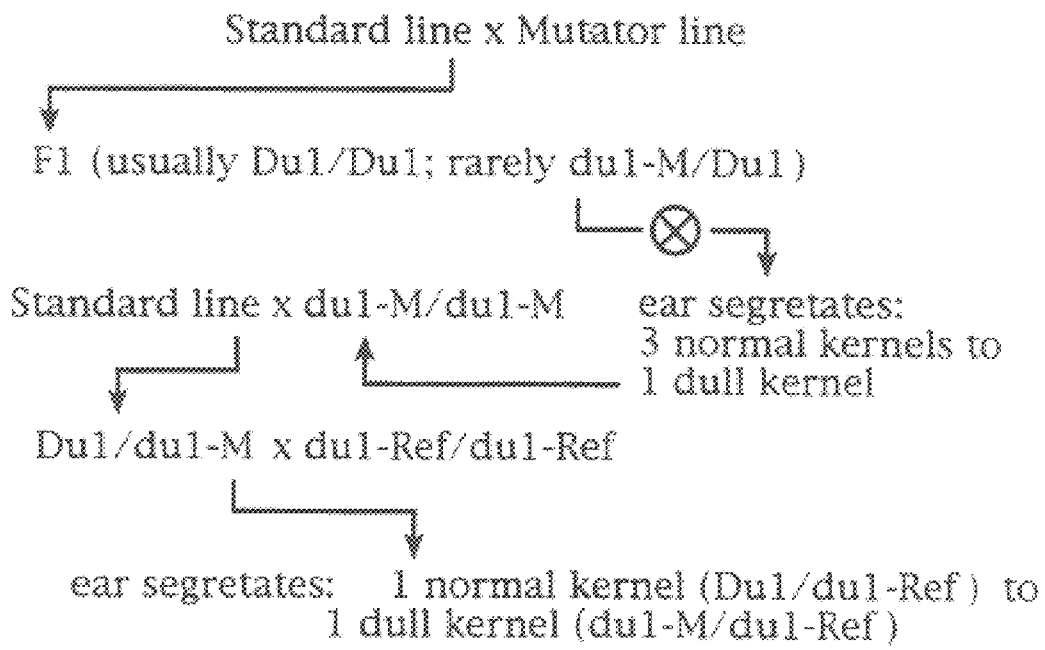
FIGS. 1A–1B show the isolation of du-mutations.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to a n oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must b e sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene which encodes a maize starch synthase enzyme of the present invention can be used to transform a host using any of the techniques commonly known to those of ordinary skill in the art. One preferred embodiment is the use of vectors containing coding sequences for the gene which encodes a maize starch synthase enzyme of the present invention for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris,* mammalian cells and insect cells, and more preferentially, plant cells such as *Arabidopsis thaliana* and *Nicotiana tabacum.*

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is a n identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

In addition, the invention also includes fragments (e.g., antigenic fragments or enzymatically functional fragments) of the maize starch synthase enzyme. As used herein, "fragment," as applied to a polypeptide, will ordinarily be at least 10 residues, more typically at least 20 residues, and preferably at least 30 (e.g., 50) residues in length, but less than the entire, intact sequence. Fragments of the starch synthase enzyme can b e generated by methods known to those skilled in the art, e.g., by enzymatic digestion of naturally occurring or recombinant starch synthase protein, by recombinant DNA techniques using a n expression vector that encodes a defined fragment of starch synthase, or by chemical synthesis. The ability of a candidate fragment to exhibit a characteristic of starch synthase (e.g., binding to an antibody specific for starch synthase, or exhibiting partial enzymatic or catalytic activity) can be assessed by methods described herein. Purified fragments of starch synthase or antigenic fragments of starch synthase can be used to generate new starch regulatory enzyme using multiple functional fragments from different enzymes, as well as to generate antibodies, by employing standard protocols known to those skilled in the art.

A standard Northern blot assay can be used to ascertain the relative amounts of starch synthase mRNA in a cell or tissue obtained from plant or other transgenic tissue, i n accordance with conventional Northern hybridization techniques known to those persons of ordinary skill in the art. Alternatively, a standard Southern blot assay may be used to confirm the presence and the copy number of the starch synthase gene in transgenic systems, in accordance with conventional Southern hybridization techniques known to those of ordinary skill in the art. Both the Northern blot and Southern blot use a hybridization probe, e.g. radiolabelled maize starch synthase cDNA, either containing the full-length, single stranded DNA having a sequence complementary to SEQ ID No. 1 or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also b e labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can b e detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, b-glucuronidase, b-D-glucosidase, b-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "metabolism" is defined as the sequence of enzyme-catalyzed reactions in which a molecule is either degraded to more simple products, or synthesized from simple precursors.

The present invention is directed towards a cDNA corresponding to the gene encoding the maize starch synthase enzyme. That is, the present invention provides an isolated cDNA having the sequence shown in SEQ ID No. 1 encoding a starch synthase enzyme from maize. The present invention is also directed to an expression vector comprising this cDNA o r fragments or derivatives thereof operably linked to a promoter allowing expression of this cDNA. Such an expression vector can be used to transfect a host cell to produce desired quantities of the maize starch synthase enzyme.

The present invention is also directed to a starch synthase protein or fragments or derivatives thereof, wherein the protein has a molecular weight of approximately 180 kDA, maximal transcript level in endosperm at 12 days after pollination, a C-terminal region possessing α-1,4-glycosyltransferase catalytic activity, and an N-terminal region containing the amyloplast targeting peptide and repeat motifs comprising, but not limited to, the M-box (SEQ ID No. 9).

In another embodiment, the present invention also provides for an antibody directed towards the maize starch synthase polypeptide, or fragments thereof.

In yet another embodiment, the present invention is directed towards a transgenic plant, wherein the transgene is a n expression vector comprising the cDNA corresponding to the maize starch synthase gene.

In another aspect, the present invention is directed to a method of producing starch, comprising the steps of transforming a cell with the vector described herein, and extracting and purifying said starch using methods described in the instant specification and readily known to one of skill in the art. This method can be used in conjunction with cells that carry additional mutations in genes involved in starch synthesis and/or metabolism, glucose synthesis and/or metabolism, glycogen synthesis and/or metabolism, and carbohydrate synthesis and/or metabolism.

In another aspect, the present invention is directed to a method of using N-terminal "arms" of DU1 expressed in transgenic plants for the purpose of binding other proteins so as to alter the function or activity of those proteins. The 1225 amino acid residues that are N terminal to the catalytic domain of DU1 (residues 1226 to 1674) define a region designated "DU1 N-terminal arm". This region contains features suggesting the entire arm or specific portions thereof are involved in interactions with other proteins. The DU1N-terminal arm may be expressed in its entirety in transgenic plants to bind one or more proteins that interact with different portions of the arm. In addition, specific regions of the DU1N-terminal arm may be expressed in transgenic plants to bind proteins that associate uniquely with those regions. Representative portions of the DU1N-terminal arm that can be expressed in transgenic plants include: (1) the nucleotide sequence comprising nt 120 to nt 1221, encoding the first 368 amino acids of DU1. This region of the protein specifically binds the branching enzyme isoform, SBEIIa; (2) the nucleotide sequence comprising n t 655 to nt 1221, encoding amino acids 180 to 368 of DU1. This region of the protein can function to activate transcription of a reporter gene in combination with the DNA binding domain from the Gal4 transcriptional activator from *Saccharomyces cerevisiae*; (3) the nucleotide sequence comprising nt 565 to nt 816, encoding amino acids 150 to 233 of DU1. This region of the protein consists of 85 residues that form three tandem repeats of 28 residues each; (4) the nucleotide sequence comprising nt 1369 to nt 1944, encoding amino acids 418 to 609 of DU1. This region of the protein consists of 180 residues that form three tandem hierarchical repeats of 60 residues each. Each of the three 60-residue repeats is designated "SBE superrepeat". Each SBE superrepeat is composed of six tandem repeats of 10 residues, which are designated "SBE repeat". The designation "SBE" in the name reflects the fact that the repeating unit is similar to a sequence found in all SBEs. The nature of the 180-residue repeat suggests that it is involved in a specific function of DU1; (5) the nucleotide sequence comprising nt 1 to nt 1437, encoding amino acids 1 to 440 of DU1. This region of the protein is unique to DU1, indicating its function is specific to DU1; (6) the nucleotide sequence comprising nt 1438 to nt 2424, encoding amino acids 441 to 769 of DU1. This region of the protein has approximately 15% identity with the corresponding region from SSIII of potato; (7) the nucleotide sequence comprising nt 2425 to nt 3791, encoding amino acids 769 to 1225 of DU1. This region of the protein is immediately N-terminal to the catalytic domain, and has approximately 51% identity with the corresponding domain in the potato SSIII enzyme.

In another aspect, the present invention is directed to a method of using full-length DU1, a DU1N-terminal arm, portions of DU1N-terminal arm, or DU1 catalytic domain as fusion proteins to purify these polypeptide regions or to identify proteins or other factors that interact with these polypeptide regions. Full-length DU1 comprising residues 1 to 1674, or the catalytic domain of DU1 comprising residues 1226 to 1674, or the DU1N-terminal arm comprising residues 1 to 1225, or portions of the DU1. N-terminal arm (described above) may be cloned into translation vectors for the purpose of expressing fusion proteins. Fusion proteins would include a affinity purification peptide or peptide tag to allow convenient detection or purification of expressed DU1 polypeptides, facilitated by binding of the peptide tag region to an affinity resin or matrix. After binding of the fusion protein to the affinity matrix, protein or whole cell extracts from plant tissues could then be incubated with the mixture, with the result that proteins or other factors that physically interact with the expressed region of the DU1 would also be bound. An example of this, a description of expression of a portion of DU1 in pET expression vector, is given below.

In another aspect, the present invention is directed to a nucleic acid sequence comprising the Du1 Promoter. The Dull1 promoter directs the expression of the Dull1 gene within a specific developmental time period and within specific tissues of the maize plant. RNA gel blot analysis indicates that Dull1 is highly expressed in developing maize endosperm, commencing approximately 12 days after pollination (DAP) and continuing through at least 32 DAP. This analysis also shows that Dull1 is slightly expressed in the maize embryo and in maize tassel tissue at approximately 20 DAP. These results were confirmed by RT-PCR analysis, which showed that Dull1-specific fragments were amplified from reverse-transcribed total RNAs isolated from developing maize endosperm, embryo, and tassel tissues, but not from leaf or root tissues. Thus, features of the Dull1 promoter ensure that Dull1 is expressed in the reproductive tissues of the plant during the period that starch is synthesized, but is not expressed in the vegetative tissues. Given the teachings disclosed herein, a person having ordinary skill in this art would readily be able to determine the sequence of the Du1 Promoter.

In another aspect, the present invention is directed to an amino acid sequence that comprises a polypeptide fragment (transit peptide) that targets the DU1 protein to the maize amyloplast. The amino acid sequence of the DU1 polypeptide predicts a transit peptide of 71 amino acids with a predicted cleavage site (VKVA_A) following amino acid 71. This cleavage sites is similar to the consensus sequence V/I-X-A/C-_-A reported for chloroplast transit peptides. Furthermore, the predicted cleavage site of DU1 has an arginine residue in the −10 position, which also is a feature consistent with chloroplast transit peptides. The DU1 protein is enriched in the maize amyloplast stromal fraction, strongly indicating that it is specifically targeted to the amyloplast by means of a transit peptide.

In another aspect, the present invention is directed to an expression vector wherein the fragment of the cDNA of SEQ ID No. 1 is selected from the group consisting of nucleotide 120 to nucleotide 1221 of SEQ ID No. 1, nucleotide 655 to nucleotide 1221 of SEQ ID No. 1, nucleotide 565 to nt 816 of SEQ ID No. 1, nucleotide 1369 to nucleotide 1944 of SEQ ID No. 1, nucleotide 1 to nucleotide 1437 of SEQ ID No. 1, nucleotide 1438 to nucleotide 2424 of SEQ ID No. 1, and nucleotide 2425 to nucleotide 3791 of SEQ ID No. 1. The present invention is also directed to a transgenic plant, wherein the transgene is the vector described above.

In another aspect, the present invention is also directed to a fusion construct, comprising part or all of the DNA the maize starch synthase enzyme fused to DNA encoding an affinity purification peptide. The present invention is also directed to the fusion protein expressed by such fusion constructs.

In another aspect, the present invention is also directed to an antisense nucleotide sequence, wherein said sequence is antisense to the cDNA of the present invention or fragments thereof. Further, the present invention is directed to a n expression vector comprising this antisense nucleotide sequence operably linked to elements that allow expression of said antisense nucleotide sequence and to a transgenic plant, wherein the transgene is this vector.

In another aspect, the present invention is also directed to starch extracted from a transgenic plant disclosed herein.

The following examples are given for the purpose of illustrating various embodiments of the invention and are not meant to limit the present invention in any fashion:

EXAMPLE 1

Nomenclature. Plant Materials and Isolation of du1-Mutations

Nomenclature follows the standard maize genetics format (Beavis et al., 1995). Alleles beginning with a capital letter indicate a functional, i.e. non-mutant, form of the gene (e.g. Du1). Unspecified mutant alleles are indicated by dashes with no following designation (e.g. du1-). Gene products are indicated by non-italicized upper-case letters (e.g. DU1).

Transcripts and cDNAs are indicated by the non-italicized gene symbol (e.g. Du1).

Standard lines used were the F1 hybrids B77/B79 or Q66/67, products of four inbred lines that have no history of Mutator activity. The Mu-active parents used in the mutant isolation scheme were described by Roberston (1978). Maize inbred line W64A was used for detection of the Du1 transcript in kernels and other tissues.

Mutant alleles du1-R2197, du1-R2339, du1-R2649, du1-R2370::Mu1, du1-R4059, and du1R-1178 were identified from the ears of self-pollinated F1 plants 87-2197-9, 87-2339-2, 87-88-2649-11, 87-2370-20, 82-4059-23, 89-1178-3, respectively (FIG. 1A). Inclusion of the letter R in the allele names indicates the stocks originally are from the laboratory of Dr. D. S. Robertson, and inclusion of the term Mu1 in allele name du1-R2370::Mu1 indicates this transposon has been identified definitively within the mutant gene. Stock number X10A from the Maize Genetics Cooperation Stock Center (Urbana, Ill.), homozygous for the reference allele du1-Ref, was used for complementation tests and to generate segregating populations (FIG. 1A).

EXAMPLE 2

Cloning

The methods used for genomic DNA extraction and DNA gel blot analysis were as described (James et al., 1995). Most probes were $^{32}$P-labeled by the standard random-primed method (Boehringer Mannheim, Indianapolis Ind.). The 2.0 kb BamHI fragment that contains Mu1 and cosegregates with du1-R2370::Mu1 was isolated from a size-selected λXZAPII-express library constructed from BamHI-digested genomic DNA from a du1-R2370::Mu1/du1-Ref plant essentially as described (James et al., 1995), and subcloned in pBluescript SK+ to form plasmid pJW3. Fragment F500 (FIG. 2B) was amplified for use as a probe by PCR from pJW3 using primers du1-sp1 (5'-GTACAATGACAACIATCCC-3') (SEQ ID No. 2) and du1-sp2 (5'-CATTCTCACAAG-TGTAGTGGACC-3') (SEQ ID No. 3). The single-stranded, $^{32}$P-labeled, F500 probe was generated by PCR using primer du-sp1 and the gel-purified BamHI fragment from pJW3 as a template according to Konat et al. (1994).

For PCR amplification of a longer genomic fragment overlapping the sequence flanking the Mu1 element in the 2.0 kb BamHI fragment, size-selected fragments were prepared from 80 μg of EcoRI-digested genomic DNA of sibling wild type plants (DU1/du1-Ref, see FIG. 1A) fractionated on a 0.5% preparative agarose gel. Five fractions of EcoRI fragments were isolated by electroelution (Sambrook et al., 1989) from consecutive gel slices bracketing the 6.0 kb size marker, and checked for the presence of Mu1-flanking sequences in the original cloned BamHI fragment by PCR using primers du1-sp1 and du1-sp2. Aliquots of two fractions containing the highest amounts of the target fragment were ligated to EcoRI-linearized pBluescript SK+, and 1 μl of each ligation mixture was used directly for PCR amplification of the region overlapping the cloned BamHI fragment using primer du1-sp1 or du1-sp2 in pairwise combination with primer T3 or T7 in pBluescript SK+. A fragment of about 2.0 kb amplified by the primer pair du1-sp1 and T3 was confirmed to contain the BamHI fragment by subsequent PCR amplification using primers du1-sp1 and du1-sp2, and was used as template for another round of PCR using the nested primer du1-sp4 (FIG. 3A) (5'-GTCGTAGGAATCGTCACTCG-3') (SEQ ID No. 4) and primer T3. The specifically amplified 1.3 kb fragment was polished with T4 DNA polymerase, digested with EcoRI to remove the remaining vector sequence, and then cloned into the EcoRV and EcoRI sites of pBluescript SK+ to form plasmid pMg1A.

EXAMPLE 3 cDNA Library Screen

Random-primed maize endosperm cDNA libraries in λgt11 were provided by Dr. Karen Cone (University of Missouri, Columbia, Mo.). Standard procedures were followed for preparation of phage lifts, phage amplification, and single-plaque purification (Ausubel et al., 1989; Sambrook et al., 1989). Phage lifts were hybridized at 65° C. for 16–18 hours to probes labeled with $^{32}$P-dCTP by the random-primed method and washed under high stringency conditions as described by Church and Gilbert (1984). cDNA inserts in phage clones were subcloned in pBluescript SK+ or pBluescript KS+ from phage DNAs prepared by the Wizard DNA purification kit (Promega).

cDNA inserts in purified phage were characterized regarding their length by direct PCR amplification from disrupted phage using two primers, λ1030 (5'-ATTGGTGGCGACGA-CTCCTG-3') (SEQ ID No. 5) and λ1356 (5'-GTGTGGGGGTGATGGCTTCC-3') (SEQ ID No. 6), located 19 bp proximal to the EcoRI cloning site in the left arm and 281 bp distal to EcoRI site in the LacZ' region of the right arm in λXgt11 phage DNA, respectively. An aliquot of homogeneous purified phage (1 μl of a 1×10$^{10}$ pfu/μl phage suspension) was disrupted in 20 μl of optimal PCR buffer (10 mM Tris-HCl, pH 9.2, 1.5 mM MgCl$_2$, 25 mM KCl) containing 0.2 μM each of the two primers and 0.2 mM each of four dNTPs for 15–20 min at 96° C., and then directly used for PCR amplification of the cDNA inserts typically as follows: 94° C. for 4 min, one cycle (add 1 unit Taq DNA Polymerase at the end); 10 cycles of 58° C. for 45 sec, 72° C. for 0.5 to 3 min (depending on the insert size) and 94° C. for 45 sec; 20 cycles of 61° C. for 1 min, 72° C. for 0.5 to 3 min (depending on the insert size) and 94° C. for 1 min; and 1 cycle of 61° C. for 5 min and 72° C. for 7 min. Lengths of cDNA inserts were determined by gel electrophoresis of 5–10 l of the PCR products.

The cDNA library screening was as follows. In the first round, about 340 positive signals were obtained in primary screening of approximately 0.5×10$^6$ pfu using fragment BE1300 as a probe. The longest cDNA insert among 15 further purified and characterized clones was 3.2 kb in length (nt 2577 to nt 5782 in the near full-length sequence). This insert was subcloned as two EcoRI fragments in plasmids pMg271L and pMg271S containing the 2.7 kb cDNA at the 5' end and the 0.5 kb cDNA at the 3' end, respectively. In the second round, the 0.5 kb EcoRI/ScaI fragment at the extreme 5' end of the 2.7 kb cDNA insert in pMg271L and the 0.5 kb EcoRI fragment of pMg271S were used separately as probes in the primary screening of an additional 1.5×10$^6$ pfu of phage. The longest insert identified by the 5' end probe in one of 24 purified and characterized phage clones, 4.3 kb in length, was subcloned in plasmid pMg6Aa. The probe from pMg271S identified an approximately 4.0 kb cDNA insert containing a 3' end EcoRI fragment of 0.67 kb that overlapped with and extended the original cloned 3' end fragment. The 1.4 kb portion from the 3' end of this 4.0 kb cDNA insert was amplified by PCR directly from purified phage and cloned as a BamHI/HindIII fragment in pMgt6-2M. The original terminal EcoRI site was mutated to a HindIII site during PCR amplification to facilitate subsequent reconstruction of the complete cDNA. The BamHI fragment of 240 bp at the 5' end of the cDNA in pMg6Aa was then used as a probe for the primary screening of another 1.0×10⁶ pfu in the third round. Among 19 purified and characterized phage clones, the cDNA insert that overlapped with the insert in pMg6Aa and containing the longest extension at the 5' end, about 1.5 kb in length, was subcloned in plasmid pMgf10. The continuous sequence of three overlapping cDNA fragments in plasmids pMgf10, pMg6Aa, and pMgt6-2M represents the near full-length cDNA sequence (FIG. 3B). Nucleotide sequences were obtained using ABI Prism automated sequencing system (Perkin Elmer) at the Iowa State University Nucleic Acid Sequencing and Synthesis Facility, using double-stranded plasmid templates. All nucleotide sequences were confirmed by analysis of both strands. Computational analyses were performed using the Wisconsin Package (Genetics Computer Group, Madison, Wis.) and the Lasergene software package (DNASTAR Inc., Madison, Wis.).

EXAMPLE 4

RNA Gel Blot Analysis and RT-PCR

Extraction of total RNA from various tissues of maize inbred W64A and RNA gel blot analysis were essentially as described (Gao et al., 1996). Radioactivity of transcripts hybridized to the Du1 cDNA probe was analyzed and quantified using a Phosphorimager (Molecular Dynamics, Sunnyvale, Calif.), and expressed as the percentage of the maximal signal strength on the same blot (Relative Level or R.L %). Minor loading differences among samples on each blot were calibrated using a tomato cDNA probe hybridizing to the 26S rRNA in the appropriate lane to normalize the Du1 mRNA signal strength.

The RT-PCR assay utilized the Titan RT-PCR system (Boehringer Mannheim) following manufacturer's instruction. The two primers used were du1-F3 (5'-ATAAATGTGTGGCGT-GGACT-3') (SEQ ID No. 7) and du-R1 (5'-CGTTCCTTGTCATTGTCCAC-3') (SEQ ID No. 8) spanning the 934 bp cDNA region from nt 3997 to nt 4930. Total RNA (1 μg) from various samples were used as templates. To distinguish RT-PCR amplification of mRNA from PCR amplification of potential residual genomic DNA, total RNA from one of the samples (22 DAP endosperm) was treated with RNase A (100 ng/ml) for 10 min at 37° C. prior to its use as a template. The RT-PCR products were analyzed on a 1% agarose gel, then blotted and hybridized using the cDNA insert of pMg6Aa as the probe to confirm the identity of the product.

EXAMPLE 5

Identification of du1- Mutations

Figure 1B:
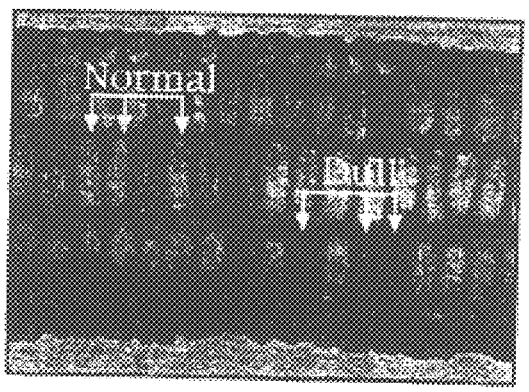

Novel du1- mutations were identified in plants derived from parental lines containing an active Mu transposable element system by the strategy outlined in FIG. 1A. Standard non-Mu lines were pollinated by Mu-active plants, and the resultant F1 progeny were self-pollinated. Six F1 ears were found that contained kernels with the dull phenotype at a frequency of approximately 25%, as illustrated in FIG. 1B. Plants grown from the dull kernels were crossed to standard lines to generate presumed DU1/du1 heterozygous kernels. These were grown to maturity and crossed to du1-Ref/du1-Ref tester plants, resulting in a 1:1 segregating population of dull and normal sibling kernels for each of the six putative Mu-induced du1-alleles. Thus, in all instances the dull phenotype is a single gene trait conditioned by a mutation that most likely is allelic to du1-Ref. The novel du1-mutations are termed du1-R2370::Mu1 , du1-R2339, du1-R2649, du1-R4059, du1-R2197, and du1-R1178.

EXAMPLE 6

Cloning and Characterization of the du-Genomic Loci

Figure 2A:
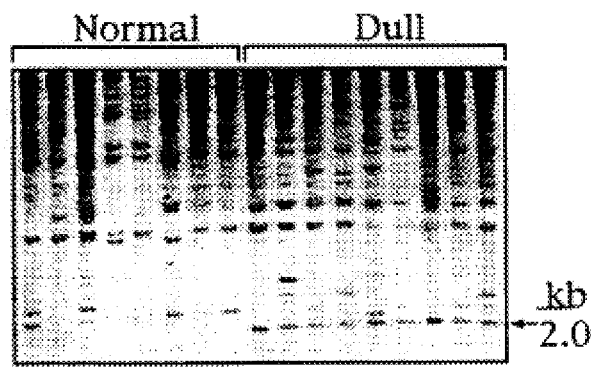
FIGS. 2A–2C show a Mu1-containing BamHI Genomic DNA Fragment Cosegregates with du1-R2370::Mu1.

A specific Mu1 transposon was found to cosegregate with the dull phenotype among progeny of a du1-R2370::Mu1/Du1 heterozygote. The heterozygous parent was crossed to a du1-Ref homozygote, generating ears containing approximately 50% dull kernels (du1-R2370::Mu1/du1-Ref) and 50% normal kernels (Du1/du1-Ref). Genomic DNAs were extracted from seedlings germinated from 35 kernels of each type, digested with BamHI, and subjected to gel blot analysis using the 960 bp internal MluI fragment of Mu1 as a probe. FIG. 2A shows representative data from these analyses; a 2.0 kb Mu1-containing fragment was detected in all analyzed plants bearing du1-R2370::Mu1, but not in any plants lacking this allele.

Figure 2B:
Figure 2C:
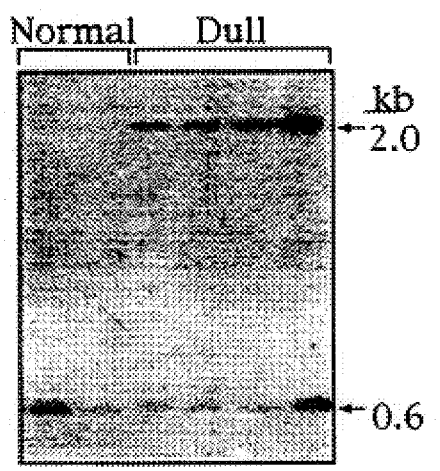

The 2.0 kb Mu1-containing genomic DNA fragment that cosegregated with the dull mutant phenotype was cloned by screening a size-fractionated genomic library, prepared from a du1-R2370::Mu1/du1-Ref heterozygote in the vector λZAPII-express, using an internal fragment of Mu1 as a probe. FIG. 2B shows the structure of the cloned fragment. As expected, the nucleotide sequence of this fragment revealed two 9 bp direct repeats (5'-GTGAGAATG-3') flanking a Mu1 element. FIG. 2C illustrates a subsequent DNA gel blot analysis confirming that the cloned Mu1-containing fragment was derived from the genomic interval that cosegregates with du1-R2370::Mu1. The single stranded probe F500, which is adjacent to the Mu1 element (FIG. 2B), detected a fragment of approximately 0.62 kb in all plants of the segregating population, and also a fragment of approximately 2.0 kb specific to plants derived from dull kernels (du1-2370::Mu1/du1-Ref). In all, 27 kernels of each type were characterized. The 1.4 kb size difference indicates that the larger 2.0 kb BamHI fragment most likely arose from insertion of a 1.4 kb Mu1 element within the 0.62 kb region delineated by these two BamHI sites. Taken together these data indicate that the cloned Mu1-containing fragment either is located within the du1 locus or is closely linked to it.

Figure 3A:
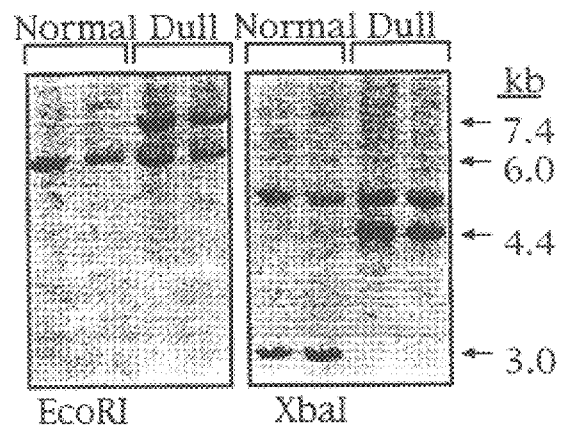
FIGS. 3A–3B show the isolation of a near full-length Du1 cDNA clone.
Figure 3B:
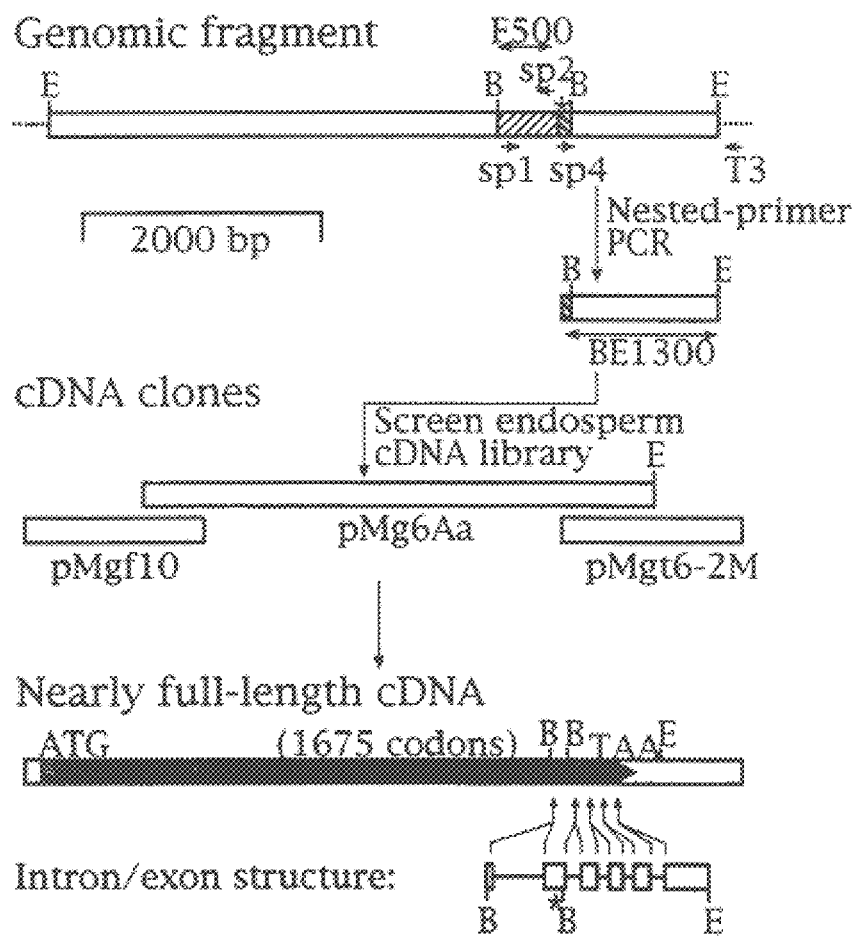

Further support for this conclusion is shown in FIG. 3A, which illustrates DNA gel blot analyses of other restriction fragments using fragment F500 as a probe. The size difference of 1.4 kb, indicating a Mu1 insertion, was also observed between the 6.0 kb EcoRI fragment detected both in Du1/du1-Ref plants and du1-2370::Mu1/du1-Ref plants and the 7.4 kb fragment found specifically in the latter. Owing to allelic variation two different XbaI fragments were detected in the Du1/du1-Ref plants of the segregating population. In sibling plants carrying du-2370::Mu1 the smaller of these two fragments, approximately 3.0 kb in size, invariably was replaced by a fragment 1.4 kb larger. The genomic DNAs used in these two analyses were derived from eight dull kernels and eight normal kernels. In all instances the difference of 1.4 kb between the larger fragment detected solely in plants bearing the mutant allele du-2370::Mu1 and the smaller fragment associated with the wild type allele Du1is consistent with insertion of this Mu1 element having caused the du1-mutation. These data also revealed larger genomic fragments that encompass the cloned 2.0 kb BamHI fragment, and thus facilitated isolation of cDNA clones corresponding to the Du1 mRNA.

EXAMPLE 7

Du1 Codes for a Transcript of at Least 6.027 bp

To obtain additional coding sequence for the purpose of screening an endosperm cDNA library, a longer genomic fragment overlapping the cloned 2.0 kb BamHI fragment was isolated from wild type genomic DNA. As described above, a 6.0 kb EcoRI fragment from wild type genomic DNA contains sequences flanking the Mu1 element in the original cloned fragment (FIG. 3A). A 1.3 kb portion of this EcoRI fragment, termed BE1300 was cloned by one-sided, nested-primer PCR amplification. FIG. 3B illustrates that fragment BE1300 extends from within the shorter Mu1-flanking region of the original cloned 2.0 kb BamHI fragment to one of the termini of the 6.0 kb EcoRI fragment. The nucleotide sequence of fragment BE1300 confirmed its overlap with the 2.0 kb BamHI fragment. Fragment BE1300 was then used as a probe to screen a maize endosperm λgt11 cDNA library.

A near full-length cDNA sequence of 6,027 bp was obtained from three overlapping cDNA clones (FIG. 3B). These clones were isolated from three consecutive rounds of screening of approximately $3 \times 10^6$ total pfu of phage. Plasmid pMg6Aa contains a 4.3 kb cDNA insert internal to the near full-length cDNA (nt 1002 to nt 5367), and the cDNA inserts in plasmids pMgf10 (nt 1 to nt 1657) and pMgt6-2M (nt 4433 to nt 6027) overlap and extend the cDNA sequence in this central cDNA fragment at the 5' and 3' ends, respectively (FIG. 3B). The continuous sequence of these three cDNA fragments revealed an ATG-initiated coding sequence of 1674 codons (FIG. 3B). Multiple stop codons in all three reading frames at the 5' end of the cDNA insert of pMgf10 indicate that the coding sequence begins within this fragment. The size of a DNA fragment amplified from endosperm total RNA by 3' RACE indicated that the 3' end of the cloned cDNA is very close to the polyadenylation site(s) of the corresponding transcript. The cloned cDNA, therefore, is nearly-full length and contains the entire coding sequence. This conclusion was supported further by detection of a 6 kb transcript in non-mutant endosperm RNA using the cDNA insert of pMg6Aa as a probe.

EXAMPLE 8

Verification of the Cloned cDNA as a Product of the du1 Locus

Figure 4:
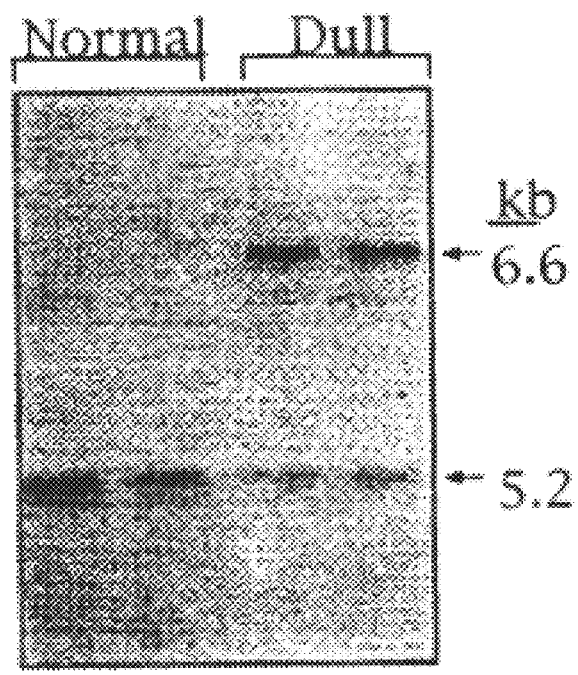
FIG. 4 shows the physical alteration of the cloned locus in plants bearing du1-R2649. SalI-digested genomic DNA of seedlings grown from du1-R2649/du1-Ref mutant and sibling Du1/du1-Ref non-mutant kernels was blotted and probed with the cDNA insert from pMgf10.

Physical characterization of another independently isolated du1 allele, du1-R4059, indicated that the cloned cDNA is coded for by the du1 locus, rather than by a different gene closely linked to du1. Genomic restriction fragments from sibling du1-R4059/du1-Ref and Du1/du1-Ref plants (FIG. 1A) were analyzed by DNA gel blot analysis using the cDNA insert of plasmid pMgf10 as the probe. As illustrated in FIG. 4, a 6.6 kb SalI fragment was detected invariably in all plants bearing du1-R4059, in addition to the 5.2 kb fragment that also was the only signal obtained from the Du1/du1-Ref plants. The size shift of 1.4 kb in the SalI fragment associated with du1-R4059 is likely to have resulted from insertion of a Mu1 element. This alteration is distinct from the one associated with du1-R2370::Mu1, because the probe that detects that polymorphism does not identify any abnormal fragment in du1-R4059 mutants (data not shown). The fact that two independent genomic rearrangements in the same gene coincide with appearance of the dull phenotype most likely is explained by Mu1 insertions being the causative agents of the du1-mutations.

Accordingly, the cloned cDNA most likely is coded for by Du1. The structure of du-R2370::Mu1 is consistent with this conclusion. FIG. 3B shows the intron/exon structure deduced by comparing the sequences of the cloned cDNA and genomic fragments. The Mu1 insertion in the cloned 2.0 kb BamHI fragment is within an exon, and thus is expected to disrupt the integrity of the transcript corresponding to the cloned cDNA in du1-R2370::Mu1 endosperm.

Figure 5A:
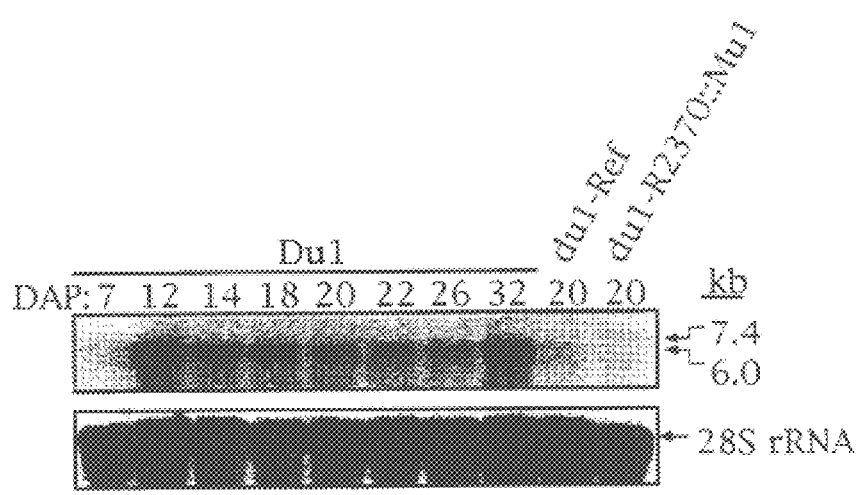
FIGS. 5A–5C show the Du1 gene has a unique expression pattern.
Figure 5B:
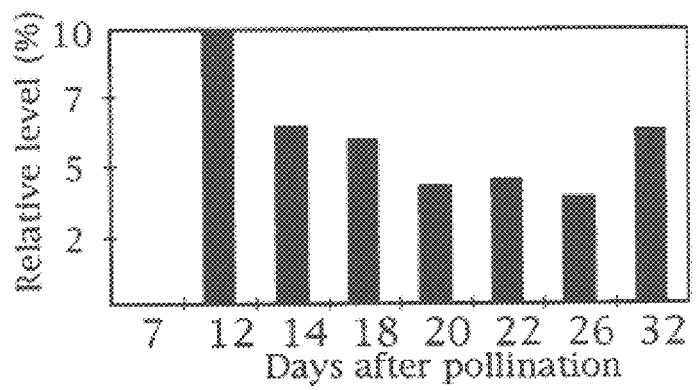
Figure 5C:
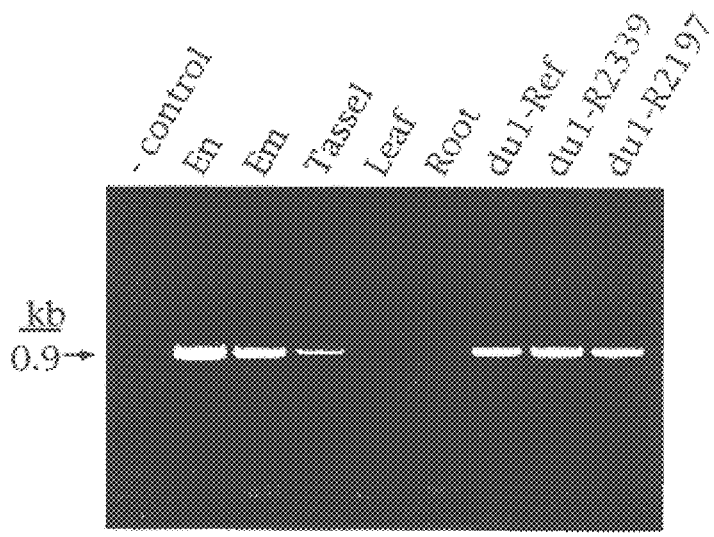

As predicted, the steady state levels of transcripts hybridizing to the cloned cDNA in du1-R2370::Mu1 and other du1-mutant endosperms were drastically reduced in comparison to non-mutant endosperm of the same developmental age. FIG. 5A shows these results for du1-R2370::Mu1 and du1-Ref endosperm as determined by RNA gel blot analyses using a portion of the cloned cDNA as a probe, and similar data were obtained for du1-R2339 and du1-R2197 endosperms. The residual transcripts in endosperm of du1-R2339 or du1-2370::Mu1 mutants were approximately 1.4 kb larger than normal (FIG. 5A) possibly resulting from transcriptional read-through of the inserted Mu1 element. The residual transcripts hybridizing to the cloned cDNA were of normal size in du1-Ref and du1-R2197 mutant endosperms (FIG. 5A and data not shown). In summary, four independently isolated du1-mutant alleles including du1-Ref are associated with disruption of the transcript detected by the cDNA probe, providing definitive confirmation that Du1 codes for the cloned cDNA. Du1 transcripts were not completely eliminated in endosperm of any of the du1-mutants examined, typical of many maize mutations affecting endosperm starch biosynthesis (Giroux et al., 1994; James et al., 1995; Fisher et al., 1996); FIG. 5C shows that residual Du1 transcripts, although possibly non-functional, were clearly detectable in endosperm of three independent du1-mutants by the more sensitive RT-PCR method, confirming the RNA gel blot results.

EXAMPLE 9

Du1 has a Unique Spatial and Temporal Expression Pattern

Gel blot analysis of total RNA from endosperm of inbred W64A collected at various days after pollination (DAP) revealed a unique temporal expression pattern of a 6.0 kb transcript hybridizing to the Du1 cDNA (FIG. 5A). Du1 transcripts were not detected in endosperm collected at 7 DAP. The transcript level was maximal in endosperm at the early developmental age of around 12 DAP, at which time other starch synthetic genes such as Sbe1, Sbe2b, Bt2, Sh2 and Wx in the same W64A inbred have little or no expression (Gao et al., 1996). The steady state level of the Du1 transcripts declined gradually over time, in contrast to other starch synthetic genes that increase expression as the endosperm develops (Gao et al., 1996). The lowest Du1 transcript level, only about 40% of maximum, was found in endosperm of 22–26 DAP, which has the highest rate of starch synthesis (Jones et al., 1996). The Du1 transcript level rebounded to about 62% of maximum in more mature endosperm of 32 DAP kernels.

Du1 transcript also was detected in other reproductive tissues, specifically embryo and tassel (most likely in pollen). Very low levels of the mRNA were barely detectable by gel blot analysis of total RNAs from these tissues. The presence of Du1 transcripts was demonstrated clearly, however, by the more sensitive RT-PCR analysis (FIG. 5C). The expected 940 bp cDNA fragment was amplified from total RNA extracted from embryo or tassel; this fragment was not amplified from RNase-digested total RNA from 22

DAP endosperm (FIG. 5C), indicating that it was amplified from mRNA rather than from residual contaminating genomic DNA. DNA gel blot analysis using a Du1 cDNA probe confirmed that the 940 bp fragment is amplified from the Du1 mRNA. The additional fragment of approximately 500 bp did not hybridize to the Du1 cDNA probe, and thus is a non-specific amplification product. Du1 transcripts were not detectable by the RT-PCR analysis in total RNAs from leaves and roots (FIG. 5C). These data suggest that the enzyme coded for by Du1 is specialized for the synthesis of storage starch in reproductive organs, but not involved in production of transient starch in leaves.

EXAMPLE 10

Du1 Codes for a Putative Starch Synthase with Conserved Features

The amino acid sequence deduced from the cloned cDNA indicates that Du1 codes for a starch synthase. The longest open reading frame of the continuous Du1 cDNA sequence codes for a polypeptide, termed DU1, of 188 kD including a potential amyloplast transit peptide. Sequence similarity searches found that the deduced amino acid sequence of DU1 is most similar to that of the potato starch synthase SSIII (Abel et al., 1996; Marshall et al., 1996) among all proteins in the public databases.

Figure 6B:
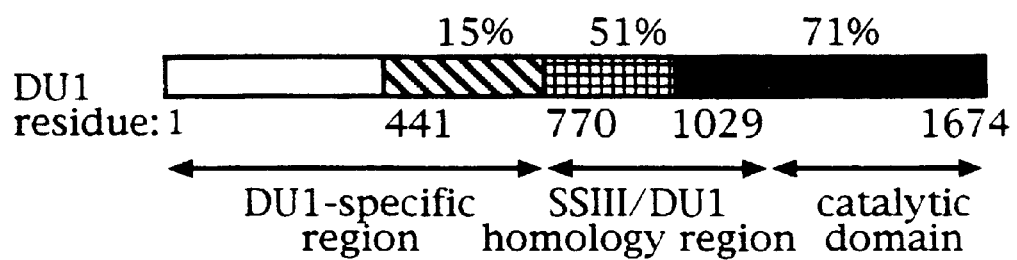

FIG. 6 shows the alignment of the DU1 and SSIII deduced amino acid sequences, and indicates three discrete regions with varying degrees of similarity between the two proteins. The C-terminal regions, over a span of 645 amino acids (DU1 residues 1029 to 1674), share the highest degree of similarity in the alignment; 73% of the aligned residues are identical in these sequences with only a single gap of one amino acid. In the central regions of DU1 and SSIII, corresponding to DU1 residues 770–1028, 51% of the 259 aligned residues are identical with no gaps in the alignment. This central region was defined by a sharp decrease in the degree of similarity between short stretches of DU1 and SSIII amino acid sequence as the alignment is examined along the lengths of the two proteins. The remaining N-terminal region of DU1 (residues 1 to 769) does not have any significant similarity to that of the potato SSIII, nor to any polypeptide sequence available in the databases. A 440-residue extension relative to SSIII is present in the DU1 N-terminus.

Further comparison of the deduced amino acid sequence of DU1 to cloned starch synthases and glycogen synthases from various species indicates that part of the C-terminal region is likely to provide α-1,4-glycosyltransferase catalytic activity. A stretch of 450 amino acid residues close to the DU1 C-terminus is substantially similar to the corresponding amino acid sequence near the C-termini of many distinct types of α-1,4-glycosyltransferase, including glycogen synthases from E. coli (Genbank accession no. P08323), yeast (Genbank accession nos. M60919 and M65206), and human liver (Genbank accession no. S70004), pea granule-bound starch synthases GBSSI and GBSSII (Genbank accession nos. X88789 and X88790), and maize GBSSI (Genbank accession no. X03935). The degree of sequence conservation in these alignments increases towards the C-termini. As an example, 28% of 438 aligned C-terminal residues are the same in both DU1 and E. coli glycogen synthase, and 67% of the 48 aligned residues of DU1 from position 1550 to 1597 are identical in the corresponding region of the E. coli enzyme with no gaps in the alignment (data not shown). Three sequence blocks are located within this region of DU1 that are highly similar to the conserved regions identified by comparison of E. coli glycogen synthase to GBSSI from a wide variety of plant species (FIG. 6A) (Preiss and Sivak, 1996).

Substantial amino acid sequence conservation at the C-termini of such a phylogenetically divergent group of α-1,4-glycosyltransferases suggests this region of DU1 is highly likely to constitute the complete catalytic domain for such an enzymatic activity. This speculation is further supported by the observation that the central regions of DU1 and SSIII, in which 51% of the amino acids are the same, have no significant similarity to any of the other cloned glycogen synthases or starch synthases. This exclusive sequence conservation, therefore, is expected to define functions belonging solely to a subgroup of plant starch synthases represented by SSIII and DU1. The unique 769 residue sequence at the N-terminus of DU1 is expected to contain an amyloplast targeting peptide and to define functions unique to this enzyme.

EXAMPLE 11

Two Groups of Repeats in the Unique N-terminal Region of DU1

Figure 7A:
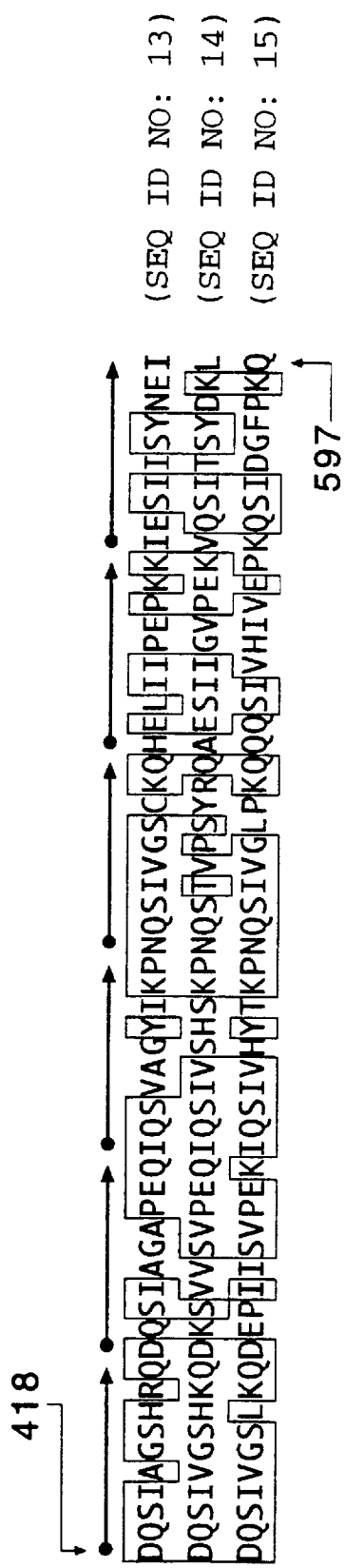

FIGS. 6A and 7 show two distinct groups of repeats comprising a total of 180 and 85 amino acids, respectively, that were identified in the unique N-terminal region of DU1 by intra-sequence dot-plot analysis. The larger group of 180 residues (positions 418–597) is a hierarchical repeat. This sequence contains three tandem repeats of 60 residues designated the "SBE-superrepeat", each of which in turn is composed of six tandem repeats of 10 residues designated the "SBE-repeat" (FIG. 7A); these names reflect the fact that the repeating unit is similar to a sequence found in all SBEs. This two-level repeating structure was deduced from the pattern of sequence conservation among the 18 SBE-repeats, i.e., each individual SBE-repeat is most similar to the two repeats positioned either 60 or 120 residues distant (FIG. 7A). Moreover, within single SBE-superrepeats, each individual SBE-repeat is always more similar to the repeat that precedes it in the N-terminal direction than to the one that follows it. These patterns of sequence similarity strongly indicate a hierarchical repeating process involving duplication of the SBE-superrepeat as a unit, rather than 18 individual repeating events. Each SBE-repeat consists of two "half-repeats", of six and four residues, respectively, as deduced from 1) the different degrees of sequence conservation exhibited by the first and second half-repeats among all SBE repeats, and 2) the presence of 4 residues between two complete SBE repeats (FIG. 6A; residues 414–417) probably resulting from an unequal crossover mechanism (Smith, 1976; Lewin, 1997).

The nature of the 180 residue repeat suggests it is involved in a specific function of DU1. The SBE-repeats that begin each SBE-superrepeat are more similar to each other than to the SBE-repeats at any of the other five positions in the superrepeat (FIG. 7A). This suggests that these three SBE-repeats were subjected to the highest selection pressure and thus may represent a functional domain. In contrast, if the first SBE-repeats were not important for function, then mutations should accumulate in those sequences at the same rate that they have appeared in other portions of the SBE-superrepeat, which is not the case. The consensus sequence among these three conserved SBE-repeats is DQSIVG (SEQ ID No. 9) in the first half-repeat, designates as the "M-box", and SHKQ (SEQ ID No. 10) in the second half-repeat. When the M-box sequence was searched for in known polypeptides only a single type of enzyme was found to contain an exact match, namely SBEI family members.

Figures 2, 7B:
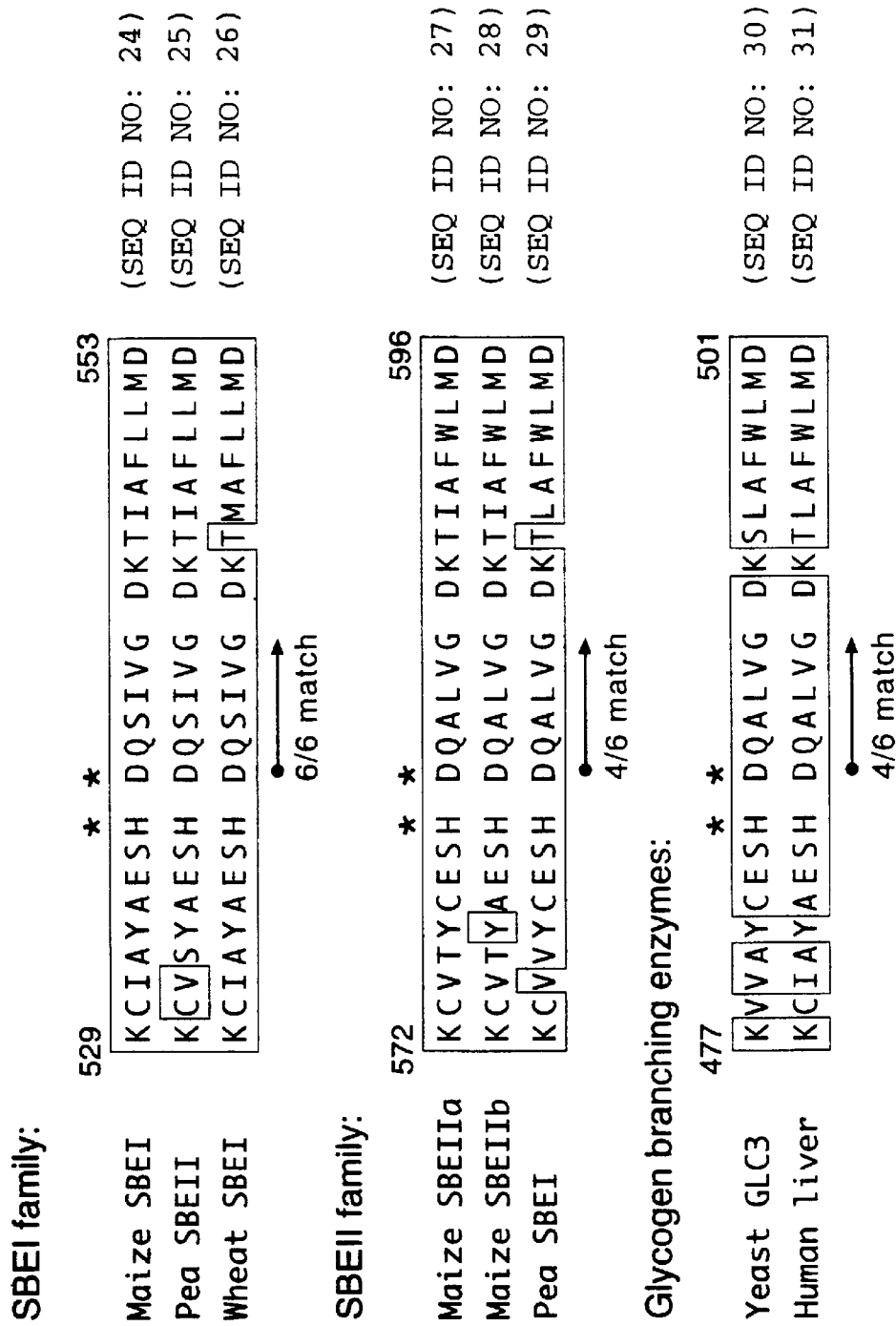

As illustrated in FIG. 7B, the M-box sequence is invariant in maize SBEI, pea SBEII, wheat SBEI, rice RBEI, and potato SBEI. The M-box is well conserved, with substitutions of two residues of similar properties yielding the sequence DQALVG (SEQ ID No. 11), in the corresponding region of SBEII family members including maize SBEIIa and SBEIIb, pea SBEI, rice RBEIII, wheat SBEII, and Arabidopsis SBE2.1 and SBE2.2 (FIG. 7B). The DQALVG sequence also is present in glycogen branching enzymes from yeast and humans (FIG. 7B).

The smaller group of repeats of 85 residues in the N-terminus of DU1 (amino acid 150-233) is composed of three tandem repeats of 28 residues (FIG. 6A and 7C). The basic repeating unit also consists of two halves, 12 and 16 resdiues each, which again are likely to have evolved via imperfect tandem duplications through the unequal cross-over mechanism. This conclusion was supported by the distinct degree of sequence conservation of the two half-repeats among the three tandem repeats. The first half-repeat is highly conserved in the first and the third copies of the 28 residue repeat, whereas the second half is more conserved in the first and third copies of the repeats (FIG. 7C).

The following four lines of evidence support the conclusion that the genomic locus cloned is a portion of the du1 gene. First, the cloned genomic interval is either within or tightly linked to the du1 locus, because it co-segregated with the dull phenotype in 70 progeny plants. Second, two independent mutations of du1 arose coincidentally with 1.4 kb insertions at distinct positions in the cloned transcription unit, one of which is known to be a Mu1 element located within an exon. Third, transcript hybridizing to the cloned cDNA is reduced drastically to the same extent in endosperm of du1-Ref and three independently isolated du1-mutants. In two of these mutants associated with Mu insertions in du1, the residual transcript is 1.4 kb larger than the wild type mRNA, consistent with insertion of a Mu1 element in an exon. Fourth, the cloned gene codes for a putative starch synthase, consistent with the fact that du1-mutants are greatly reduced in the activity of the soluble starch synthase SSII.

Assuming that the Du1 transcript level reflects enzyme activity, these observations suggest DU1 is involved in starch biosynthesis at a chronologically very early step, possibly closely associated with the initiation event. Conservation of the M-box sequence, the presumed first half-repeat within the amplified SBE-repeat, specifically in starch- and glycogen branching enzymes from phylogentically very divergent species is particularly striking considering that SBEs and SSII act in a concerted biosynthetic pathway. The M-box sequence, therefore, may be a basic structural motif for a particular function shared by all these enzymes, possibly including glucan binding, protein-protein interaction, or serving as regulatory sites. In addition, many consensus sites for N-glycosylation and phosphorylation were found within these repeats, suggesting that they may serve as regulatory sites. The whole group of repeats may form a helix-turn-helix structure, reminiscent of the DNA-binding helix-turn-helix motifs in many transcription factors (Mitchell and Tjian, 1989). Considering the helical architecture of both DNA and α-(1→4)-linked glucan polymers, the 85 residue repeat may mediate binding of SSII and associated proteins to growing glucan chains.

Thus, the present invention is directed to an isolated cDNA having the sequence shown in SEQ ID No. 1 encoding a starch synthase II enzyme from maize. Typically, a person with ordinary skill in this art could contruct an expression vector comprising this cDNA, or functional fragments thereof, operably linked to elements that allow expression of the cDNA. Further, one could transfect a host cell with this vector.

The present invention is also directed to a starch synthase II enzyme from maize encoded by this cDNA. The present invention is also directed to a polypeptide encoding a starch synthase II protein, wherein said protein has a molecular weight of approximately 180 kDA, maximal transcript level in endosperm at 12 days after pollination, a C-terminal region possessing α-1,4-glycosyltransferase catalytic activity, and an N-terminal region that contains the amyloplast targeting peptide and repeat motifs comprising, but not limited to, the M-box (SEQ ID No. 9). In one embodiment, the protein has the amino acid sequence shown in SEQ ID No. 12. The present invention is also directed to an antibody directed towards the polypeptide described herein, or functional fragments thereof.

In a separate embodiment, a person having ordinary skill in this art could manipulate a plant to create a transgenic plant, having as the transgene the vector described above. Using this technology, one could produce starch, comprising the steps of: transforming a cell with the vector described herein; and extracting and purifying said starch. Preferably, the cells carry a mutation. Representative examples of useful mutations include a gene encoding an enzyme involved in starch synthesis, starch metabolism, glucose synthesis, glucose metabolism, glycogen synthesis, glycogen metabolism, carbohydrate synthesis and carbohydrate metabolism.

Manipulation of the enzymatic machinery of starch production in higher plants can be used to create starch forms that have specific branching patterns and specific chain lengths. Properties of chain length and/or degree of branching confer specific characteristics on starch such as swelling, polarity, water retention, clarity, ability to disperse pigments, and freeze-thaw properties. The production of tailored starches with defined and predictable properties is expected to be useful for a variety of specific food and industrial applications. Altering the activity of the DU1 starch synthase through the transgenic approaches listed below can be used to create novel starch forms with chain lengths and/or branching patterns that differ from those in traditional starches. For example, one can modify starch in transgenic plants by the over-expression of DU1 starch synthase. Secondly, one could modify starch in transgenic plants by reducing or eliminating the expression of DU1 starch synthase, either by 1) introduction of DU1 in the antisense orientation, or by 2) cosuppression of DU1 resulting from over-expression of the DU1 transgene the over-expression of DU1 starch synthase. Thirdly, one could modify starch in transgenic plants by the introduction of an altered Du1 sequence, thereby producing an altered DU1 protein. Fourthly, one could modify starch in transgenic plants by the introduction of a polypeptide fragment of the DU1 protein, or by introduction of a polypeptide fragment of the DU1 protein in the antisense orientation, or by introduction of an altered polypeptide fragment of the DU1 protein. Additionally, one could modify glycogen production in transformed bacterial and/or yeast cells by the expression of DU1 starch synthase. DU1 expression may be placed under the control of constitutive or inducible promoters. One could propagate the transgenic plants to produce a described starch form with specific characteristics, or cross the transgenic plants with plants in distinct genetic backgrounds or which have distinct genetic traits to produce additional altered starch forms. These starches could be marketed for their unique features to various industries; for example, as food or beverage additives, or as processing agents in the manufacturing of paper or textiles. Also, a licensee could grow recombinant yeast or bacteria engineered to express DU1 starch synthase in large-scale to produce an altered glucan which would have industrial utility.

Also provided by the present invention are polypeptide fragments comprising regions of the DU1 starch synthase recognized by an antibody specific for a DU1 determinant. A polypeptide comprising a DU1 fusion protein could be prepared by one having ordinary skill in this art as is an antibody reactive with the DU1 protein or polypeptide fragments.

One having ordinary skill in this art could also prepare a transgenic plant comprising a genome including a foreign DNA sequence encoding the DU1 protein under the control of its own promoter or another promoter; or including a sequence encoding DU1 modified to produce altered DU1 activity.

EXAMPLE 12

Construction of Expression Plasmids

Plasmid pHC1 was constructed as an intermediate in generation of the antigens used to raise anti-DU1N and anti-DU1F; this plasmid contains the entire Du1 cDNA coding region delineated by two EcoRI sites, one located immediately upstream of the presumed initiation codon, and the second 225 bp downstream of the termination codon. A 1.5 kb fragment was PCR-amplified from the partial Du1 cDNA clone pMgf10 (Gao et al., 1998) using primers HCp1 and M13F. HCp1 (5'-AAACCCGGGAATTCGATGGAGATGGTCCTACG-3') (SEQ. ID. No: 37) contains SmaI and EcoRI sites located upstream of the presumed initiation codon (restriction sites and the initiation codon are underlined), and M13F is located downstream of the cDNA insert on the noncoding strand. The amplified fragment was cleaved at the SmaI site of the primer and the unique AgeI site within the cDNA sequence. This fragment was cloned in the SmaI and AgeI sites of pMg10-6, which contains the Du1 cDNA extending from 125 bp upstream of the presumed initiation codon to the downstream EcoRI site. The resultant plasmid is pHC1.

Plasmid pHC2 expresses a fusion protein containing the *Schistosoma japonicum* glutathione-S-transferase (GST) protein at its N terminus and DU1 residues 1–648 at its C terminus; this polypeptide was used as the DU1N antigen. pHC2 was constructed by cloning the EcoRI-SalI fragment from pHC1 into pGEX4T-3 (Pharmacia) digested with the same enzymes. Plasmid pHC4 expresses a fusion protein containing thioredoxin at its N terminus and full-length DU1 at its C terminus; this protein was used as the DU1F antigen. pHC4 was constructed by cloning the EcoRI fragment from pHC1 into pET-32b(+) (Novagen).

Plasmids pHC5 and pHC6 express the C terminal region of DU1 (DU1C) in *E. coli*. The Du1 cDNA from codon 1226 to termination codon 1675 was PCR-amplified using pHC1 as the template. The upstream primer was HCp2 (5'-GCA GAATTCGATGCACA-TTGTCCAC-3'), which places an EcoRI site adjacent to codon 1226 (the EcoRI site and codon 1226 are underlined). The downstream primer was M13F. The amplified fragment digested with EcoRI was cloned into pET-29b(+) and pET-32b(+) (Novagen) to form pHC5 and pHC6, respectively. The sequence of the entire DU1C insert and the junction with the T7 promoter was determined in clones with correct restriction maps. Two amino acid substitutions were found relative to the cDNA sequence, Q for H at position 1281, and N for K at position 1294. Neither of these residues is in a conserved region of the plant SSs.

EXAMPLE 13

Production of anti-DU1N and anti-DU1F

To produce the DU1N antigen, 1 L exponential phase cultures of *E. coli* cells containing pHC2 were grown for 2 hours at 37° C. in the presence of 0.1 mM IPTG. Cells were collected by centrifugation and the pellet (7 g wet weight, from 2 L of culture) was suspended in 100 mL of 140 mM NaCl, 2.7 mM KCl, 10 mM $Na_2HPO_4$, 1.8 mM $KH_2PO_4$, 1 mM PMSF, 0.01 mM E-64, 10 mM EDTA, 5 mM DTT, 1 mg/ml lysozyme; all subsequent treatments were at 0° C. Cells were lysed by sonication. GST-DU1N fusion protein was affinity purified using glutathione-agarose beads. The fusion protein was eluted in 100 mM Tris-HCl, pH 8.0, 120 mM NaCl, 20 mM glutathione.

To produce the DU1F antigen 0.5 L exponential phase cultures of *E. coli* cells containing pHC4 were grown for 1.5 hours at 37° C. in the presence of 0.5 mM IPTG. Cells were collected by centrifugation, suspended in 25 mL of 50 mM Tris-HCl, pH 7.0, 1 mM PMSF, 10 mM EDTA, 5 mM DTT, 10% glycerol, 3% of 10× proteinase inhibitor cocktail (Sigma no. P2714), and broken by sonication. Lysates were centrifuged at 10000×g for 10 min, and the pellets were dissolved by boiling for 10min in 1× SDS-PAGE sample buffer. A band of greater than 200 kD was observed in SDS-PAGE that was specific to cells containing pHC4 and reacted with anti-DU1N in immunoblot analysis. This protein, therefore, was identified as the DU1F antigen. The DU1F antigen band was cut out of large scale 6% polyacrylamide gels, crushed to a powder, and used for immunization.

Antisera were raised in rabbits by standard procedures (Harlow and Lane, 1988). For initial immunization with the DU1N antigen 300 μg of protein was injected in complete Freund's adjuvant. Booster immunizations of 200 μg fusion protein were supplied three times at three week intervals. Immunization with DU1F followed a similar protocol except that approximately 50 μg of antigen was supplied in all four injections.

EXAMPLE 14

Expression of DU1C in *E. coli*

*E. coli* BL21(DE3) strains containing pHC5 or pHC6 were grown in LBK or LBA medium, respectively. Overnight cultures were inoculated into fresh medium at a 1:10 dilution and grown at 37° C. until the density was 0.8 $A_{600}$/ml. IPTG was added to 0.5 mM and the cultures were grown for 5 hours at 25° C. Cells were collected by centrifugation, suspended in $1/20^{th}$ culture volume of sonication buffer (50 mM Tris-HCl, pH 7.0, 10% glycerol, 10 mM EDTA, 5 mM DTT, 3% of 10× proteinase inhibitor cocktail [Sigma no. P8465]), and broken by sonication. Lysates were cleared by centrifugation in a microfuge and the supernatants were used for subsequent analyses. The S-tag Rapid Assay Kit (Novagen) was used for detection of S-tag sequences by measurement of reconstituted ribonuclease A activity.

EXAMPLE 15

Zymogram Analysis

Zymograin analysis was performed essentially as described by Buleon et al. (1997) with a few modifications. Endosperm from 3–4 kernels was frozen in liquid nitrogen, crushed to a fine powder, and suspended by vortexing in 50 mM Tris-acetate, pH 8.0, 10 mM EDTA 5 mM DTT, (1 mL per gram kernel fresh weight). The crude homogenate was cleared by centrifugation at 10,000×g for 10 min at 4° C. and protein concentration in the supernatant was determined. Protein samples (225 μg) were boiled in SDS-PAGE buffer (65 mM Tris-HCl, pH 6.8, 2% SDS, 10% glycerol, 5% 2-mercaptoethanol) and loaded onto an 8% acrylamide gel containing 0.1% glycogen. Electrophoresis was performed under denaturing conditions (25 mM Tris-HCl, pH 8.3, 192 mM glycine, 0.1% SDS, 5 mM DTT) for 3 hours at 4° C. at 80 V in a BioRad Mini-Protean II cell. The gel was washed four times for 30 min each at room temperature in 40 mM Tris-HCl, pH 7.0, 5 mM DTT, to remove SDS and allow proteins to renature. The gel was then incubated in reaction buffer (100 mM Bicine, pH 8.0, 0.5 M citrate, 25 mM potassium acetate, 0.5 mg/mL BSA, 5 mM ADPGlc, 5 mM 2-mercaptoethanol, 20 mg/mL glycogen) for 36 hours at room temperature. Enzyme activities were detected by adding iodine stain (0.2% iodine and 2% potassium iodide in 10 mM HCl) and the zymograms were photographed immediately.

EXAMPLE 16

Fractionation of Maize Kernel Extracts

Kernels were collected from developing ears, immediately frozen in liquid nitrogen, and stored at −80° C. Frozen kernels were ground on ice with a mortar and pestle in homogenization buffer (50 mM Tris-HCl, pH 7.0, 10% glycerol, 10 mM EDTA, 5 mM DTT, 1 mM PMSF, 50 μl per gm tissue of 10× proteinase inhibitor cocktail [Sigma no. P2714]; 2.5 mL/gm tissue). The homogenate was centrifuged at 10000×g for 10 min, and the supernatant was used for SS assays and protein concentration determination. To obtain starch granules the 10000×g pellet was vortexed vigorously in homogenization buffer and centrifuged again. The pellet from the third such wash was suspended in homogenization buffer and used as the starch granule fraction.

EXAMPLE 17

Glucan Synthase Assays

Glucan synthase assays were performed in microfuge tubes in a total volume of 0.1 mL. The standard reactions contained 100 mM Bicine-NaOH, pH 8.0, 5 mM EDTA, 0.5 M sodium citrate, 0.5 mg/mL BSA, 10 mg/mL glycogen, 1 mM ADP-[$^{14}$C]glucose (150 cpm/nmol) (Amersham no. CFB144) and various amounts of total soluble extract. Reactions were initiated by addition of the labeled ADPG, incubated for 30 min at 30° C., and terminated by addition of 1 mL 75% methanol/1% KCl Incorporation of radioactive label into methanol-insoluble glucan was determined according to Cao and Preiss (1996). All assays were performed in duplicate or triplicate, and the maximal observed variation was approximately 10%. Preliminary experiments demonstrated that the amount of $^{14}$C incorporated into methanol-precipitable glucan is linear with the amount of protein in the assay. Furthermore, approximately 10% of the $^{14}$C cpm in the assay was recovered in insoluble glucan. Thus, the assays were performed in conditions of substrate excess.

Some assays varied from the standard procedure by omission of glycogen and/or sodium citrate. When glycogen was omitted from the assay, it was added to the standard concentration after the reaction was stopped by methanol addition.

EXAMPLE 18

Immunoblot and Immunodepletion Methods

Protein concentrations were determined according to Bradford (1976). SDS-PAGE and transfer of protein from the gels to nitrocellulose filters followed standard methods (Sambrook et al., 1989). Primary antisera were anti-SSI (Mu et al., 1994) diluted 1:1000 or 1:3000, anti-DU1N diluted 1:10,000 or 1:75,000, and anti-DU1F diluted 1:2000. Secondary antibody was goat anti-rabbit IgG-alkaline phosphatase conjugate (Bio-Rad Laboratories) diluted 1:3000, which was detected using the BCIP/NBT reagent system (Bio-Rad Laboratories). Fusion proteins containing the S-tag amino acid sequence were detected by the same procedure except that S-protein alkaline phosphatase conjugate (Novagen) diluted 1:5000 was used instead of a primary antibody.

Immunodepletion experiments were performed as follows. Total soluble kernel extracts were mixed with an equal volume of immune serum plus preimmune serum. In all instances the total volume of serum added to the protein extracts was constant; the variable was the ratio of immune/preimmune serum in the mixture. The solutions were incubated on ice for 90 min with gentle mixing every 10–15 min. Protein A-Sepharose CL-4B (Sigma) was added ($\frac{1}{10}^{th}$ volume of bead slurry/protein solution). The mixtures were gently shaken continuously for 30 min, centrifuged for 10 min at 10000×g, and the supernatants were assayed for SS activity. The pellets were washed with buffer three times prior to immunoblot analysis of the precipitated proteins.

EXAMPLE 19

Sequence Motifs Conserved in DU1 and SSs

Three conserved sequence blocks identified previously in comparisons of various WX proteins and *E. coli* glycogen synthase (GS) are all present in the DU1C terminal region. This comparative analysis was extended to include 28 SS or GS sequences from 17 species. Thirty-three residues are conserved in all 28 enzymes. Five conserved sequence motifs were identified in addition to the three noted previously. The eight conserved sequence blocks are designated motifs I-VIII, in order from the N terminus to the C terminus; according to this notation motifs I, VII, and VIII correspond to regions I, II, and III, respectively, as designated previously. The conserved sequences are distributed in the 359 residues of DU1 between positions 1237 and 1595.

EXAMPLE 20

Recombinant DU1 Protein Exhibits SS Activity

Figure 8:
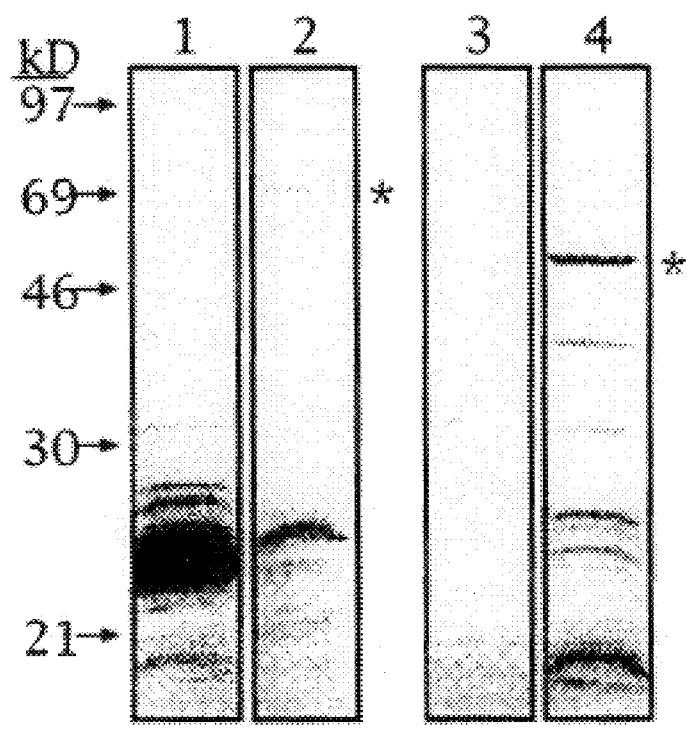
FIG. 8 shows the expression of DU1C in *E. coli*. Gene expression from the T7 promoter of the indicated plasmid was induced in exponential phase *E. coli* cells. Total soluble lysates were fractionated by SDS-PAGE and specific proteins containing the S-tag sequence (specified by the pET plasmid) were detected by S-protein AP conjugate. Lane 1: pET-32b; Lane 2: pHC6 (DU1C in pET-32b); Lane 3: pET-29b; Lane 4: pHC5 (DU1C in pET-29b). Asterisks indicate polypeptides of approximately the size predicted from the plasmid and Du1 cDNA sequence, which are present only when the DU1C coding region is contained within the plasmid.

Sequence similarity of DU1 to glucan synthases suggests that its C terminal region beginning upstream of residue 1237 possesses SS activity. To test this hypothesis the 449 C terminal residues (position 1226-1674; designated DU1C) were expressed in *E. coli* from plasmids pHC5 or pHC6. These plasmids are based in the expression vector pET-29b (+) or pET-32b(+), respectively, and thus produce DU1C fusion proteins containing either 35 or 167 plasmid-derived residues at their N terminus. Expression of the fusion proteins was monitored by enzymatic and immunoblotting analyses that detected the S-tag sequence present in these N terminal extensions. Proteins of the expected sizes were expressed specifically when the DU1C coding region was present (FIG. 8).

Increased glucan synthase activity was observed in total soluble extracts of *E. coli* cells expressing DU1C. Cells containing pHC5 or pHC6 were exposed to IPTG to induce expression of the DU1C proteins and total soluble extracts were tested for glucan synthase activity. DU1C expression caused approximately 5-fold increased SS activity compared to control cells lacking the maize coding region (Table 1). A similar increase occurred also in the reconstituted ribonuclease A activity conferred by the S-tag sequence of the N terminal extension (data not shown). Nearly identical results were obtained when DU1C was expressed in pET-29b(+) or pET-32b(+). The activity increase relative to the endogenous level was relatively modest, although similar levels were detected also for zSSI expressed in *E. coli*. In addition the level of recombinant enzyme activity observed for DU1C was comparable to that of potato GBSSII expressed in a similar system. These data provide direct evidence that DU1 is a starch synthase and that its C terminal 449 residues are sufficient to provide this enzymatic activity.

TABLE 1

Starch synthase activity in total soluble *E. coli* extracts

| Plasmid | Insert | Specific Activity nmol min$^{-1}$ mg$^{-1}$ | % |
|---|---|---|---|
| pET-29b(+) | None | 2.10 ± 0.29 | 100 |
| pHC5 | DU1-C$^b$ | 10.41 ± 1.93 | 496 |
| pET-32b(+) | None | 2.88 ± 0.18 | 100 |
| pHC6 | DU1-C | 14.19 ± 1.60 | 493 |

$^a$nmol glucose incorporated min$^{-1}$ mg$^{-1}$. Values indicate the mean ± standard error (n = 4).
$^b$Total activity units obtained for the appropriate plasmid vector with no insert are assigned a value of 1.
$^c$pET-29b(+) and pET-32b(+) are from Novagen. pHC5 and pHC6 are based in these two vectors, respectively.
$^d$DU1 residues 1226–1674. Gene expression was induced for five hours in exponential phase *E. coli* cells transformed with the indicated plasmid. Total soluble extracts were assayed for starch synthase activity in the presence of citrate and glycogen primer.

nmol glucose incorporated min$^{-1}$ mg$^{-1}$. Values indicate the mean ± standard error (n=4). $^b$Total activity units obtained for the appropriate plasmid vector with no insert are assigned a value of 1. $^c$pET-29b(+) and pET-32b(+) are from Novagen. pHC5 and pHC6 are based in these two vectors, respectively. $^d$DU1 residues 1226–1674. Gene expression was induced for five hours in exponential phase *E. coli* cells transformed with the indicated plasmid. Total soluble extracts were assayed for starch synthase activity in the presence of citrate and glycogen primer.

Several efforts were made to express full-length DU1, however, in all instances the protein did not accumulate as judged by immunoblot analysis. Full-length DU1 expressed from pHC4 was found exclusively in the insoluble phase of *E. coli* cells. Growth in media shown previously to increase solubility of recombinant SSs did not result in expression of soluble DU1. Attempts to express full-length DU1 as a fusion protein targeted to the periplasmic space of *E. coli* (IBI FLAG Expression System; Sigma no. E5769) or in *Saccharomyces cerevisiae* as a presumed cytosolic protein (pYES2; Invitrogen) also were unsuccessful.

EXAMPLE 21

Immunological Detection of DU1 in Kernel Extracts

Figure 9A:
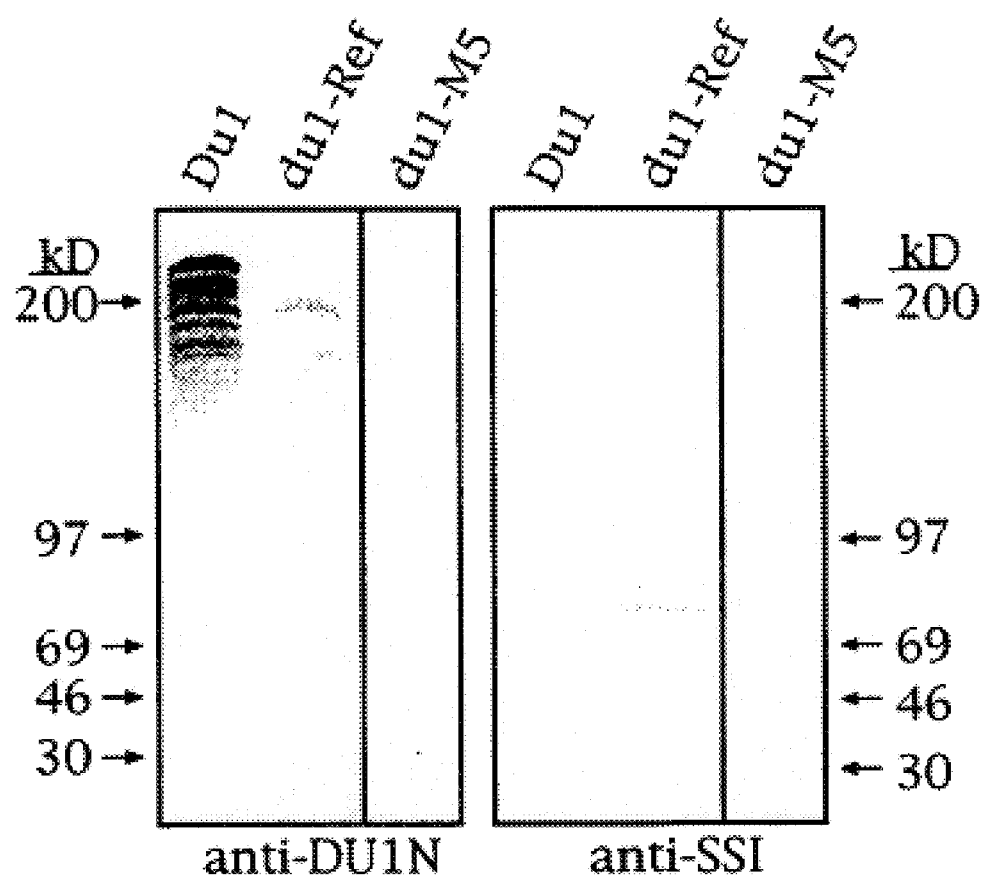
FIGS. 9A–9C show the immunologic detection of DU1 and SSI in kernel extracts.

Detection of DU1 in kernel extracts revealed the apparent size of this SS, its temporal expression pattern, and its lack of association with starch granules. The polyclonal antiserum anti-DU1.N was raised in rabbits against the N terminal 648 residues of DU1. This region of DU1 is unique among known protein sequences so anti-DU1. N is expected to react specifically with DU1 and not with other SSs. FIG. 9A shows that in immunoblot analysis of total soluble kernel extracts (i.e., the 10,000×g supernatant) from nonmutant kernels anti-DU1N detected a protein that migrated at an apparent molecular weight of greater than 200 kD. This protein was missing in two different du1-mutants. In kernels homozygous for the reference mutation, du1-Ref, a smaller immunoreactive protein was detected, whereas in kernels homozygous for the presumed transposon-induced allele du1-R4059 the protein was completely eliminated (FIG. 9A). Identical results were obtained using a different antiserum, anti-DU1F, which was raised against full-length DU1. Thus, both anti-DU1N and anti-DU1F recognize DU1, the product of the du1 gene.

The zSSI protein of apparently 76 kD also was identified in immunoblot analysis of these same kernel extracts, using anti-SSI antiserum (FIG. (9A). Anti-DU1N did not recognize SSI, and anti-SSI did not recognize DU1. In this assay, therefore, both antisera react specifically with a distinct isozyme. DU1 was found to be located primarily in the soluble fraction of kernel extracts as opposed to being associated with starch granules. Kernels harvested 20 DAP were fractionated into soluble and granule fractions. The identity of the granule fraction was verified by enrichment for zSSI (FIG. 9B), which is known to be both granule-associated and soluble. The amount of DU1 present in the granule and soluble fractions was determined by immunoblot analysis of protein samples standardized based on kernel fresh weight. In contrast to zSSI, the anti-DU1. N signal was found almost exclusively in the soluble fraction (FIG. 9B), indicating that DU1 is not stably associated with starch granules in 20 DAP endosperm.

Figure 9B:
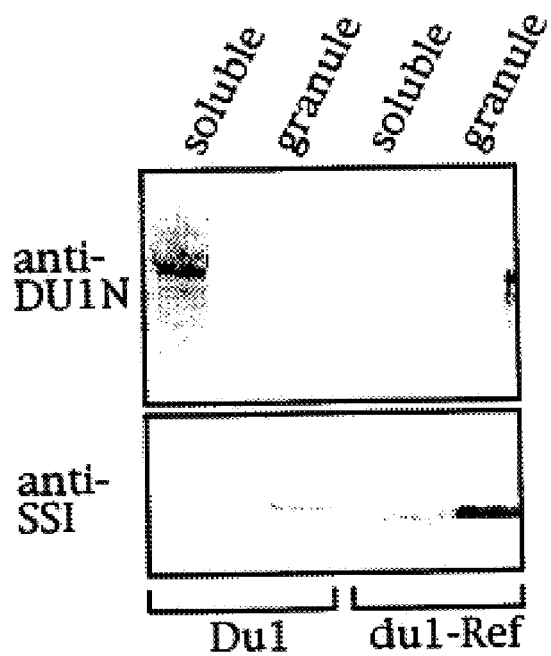
Figure 9C:
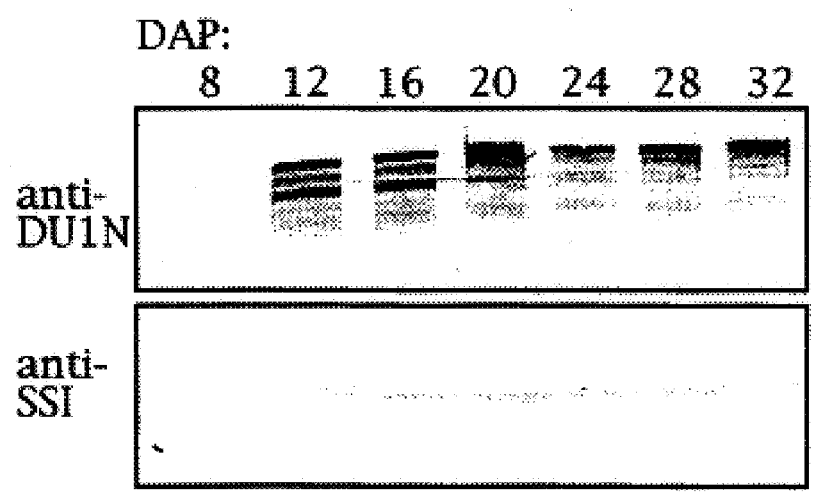

The temporal expression pattern of DU1 and SSI in kernels at various times after pollination was monitored. DU1 was detected first at 12 DAP and was maintained at a nearly constant level throughout the period of starch biosynthesis up to at least 32 DAP (FIG. 9C). Anti-SSI produced a signal in the 8 DAP kernel extract (FIG. 9C), indicating that in these tissue samples zSSI was expressed earlier than DU1.

EXAMPLE 22

Immunodepletion of SS Activity in Kernel Extracts

Figure 10:
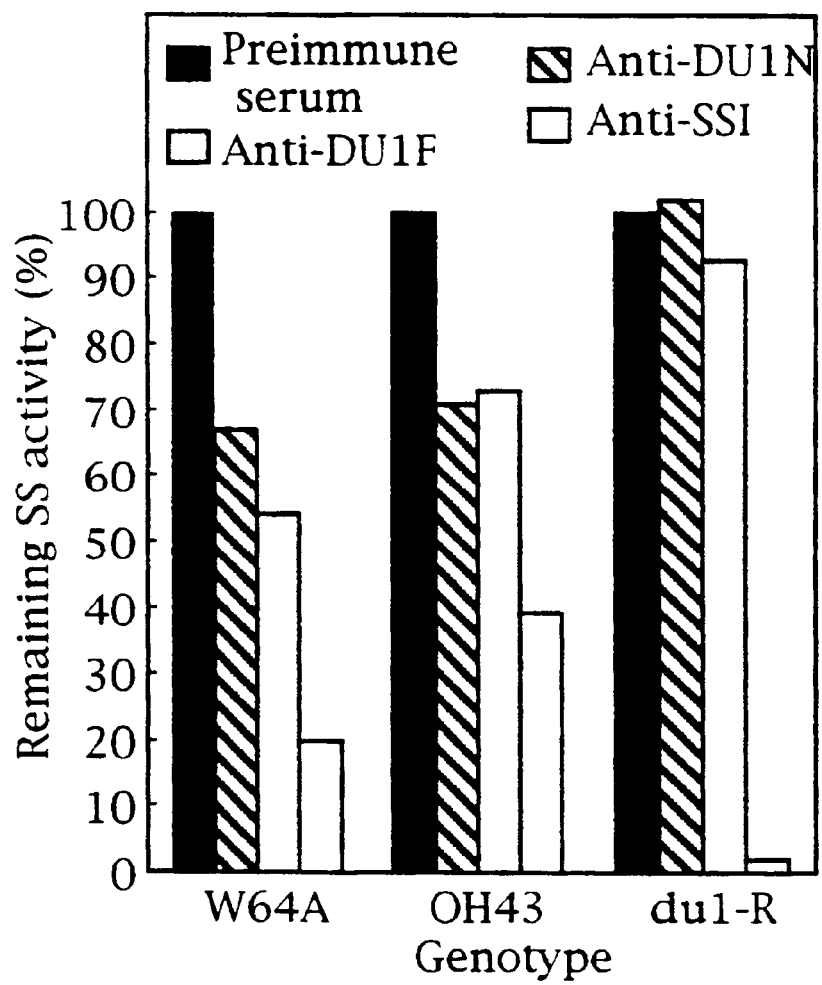
FIG. 10 shows the immunodepletion of SS activity. Total soluble extracts from kernels of the indicated genotype collected 20 DAP were treated with preimmuine serum, or saturating amounts of the indicated antiserum, and residual SS activity was assayed following removal of the immune complexes. The du1-Ref mutant was in the W64A genetic background. SS activity remaining after treatment with preimmune serum was defined as 100%. These values were 7.0 nmol min$^{-1}$ mg$^{-1}$ for W64A, 12.9 nmol min$^{-1}$ mg$^{-}$for the du1-Ref mutant, and 16.4 nmol min$^{-1}$ mg$^{-1}$ for Oh43.

Immunodepletion experiments investigated the amount of SS activity in endosperm provided by DU1 and zSSI. Total soluble extracts of kernels harvested 20 DAP were treated with anti-DU1N, anti-DU1F, anti-SSI, or preimmune serum. Immune complexes were removed from solution after binding to protein A-Sepharose beads, and residual SS activity in the supernatant was determined in the presence of citrate and exogenous primer. Preliminary experiments titrated the amount of serum; the following data were obtained in conditions of antibody excess. Nonmutant extracts of either the W64A or Oh43 background were depleted of approximately 35–45% of their total SS activity by either anti-DU1 serum (FIG. 10). Anti-SSI depleted 80% and 60% of the total SS activity in the two genotypes, respectively. Treating du1-mutant extracts with either anti-DU1 serum had virtually no effect on total SS activity, suggesting that the particular enzyme affected by these sera is specifically that coded for by Du1. Treatment of the du1-mutant extracts with anti-SSI depleted virtually all of the SS activity. These data demonstrate that the great majority of SS activity in the soluble fraction of 20 DAP endosperm is provided by a combination of zSSI and DU1.

EXAMPLE 23

Fractionation of SS Activities in Total Endosperm Extracts

Figure 11A:
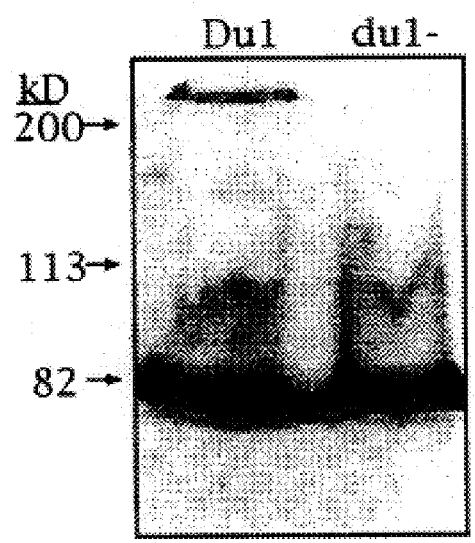
FIGS. 11A–11B shows the specific identification of SS isozymes.
Figure 11B:
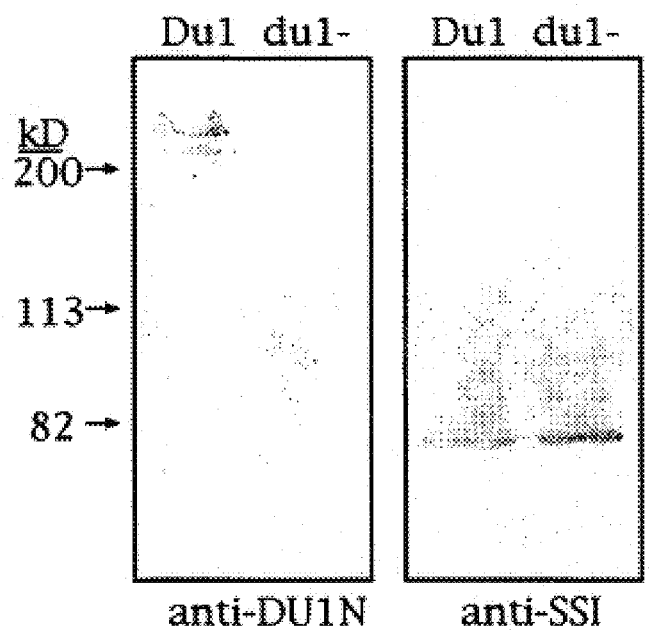

The SS activities present in 20 DAP endosperm also were correlated with particular cloned cDNAs by a combination of zymogram, immunoblot and mutational analyses. These SSs were fractionated by SDS-PAGE and detected by their activity in gels following protein renaturation. Two activity bands were observed, one of greater than 200 kD and the other of approximately 76 kD (FIG. 11A). The sizes of these isozymes correlate roughly with those predicted by the Du1 cDNA and the Ss1 cDNA, respectively. Immunoblot analysis of the same protein samples revealed that the >200 kD isozyme reacted with anti-DU1N, whereas the 76 kD isozyme reacted with anti-zSSI (FIG. 11B). Extracts from du1-mutant endosperm entirely lacked activity of the >200 kD isozyme. These results suggest that there are two major soluble SSs present in developing endosperm cells, and that one of these is DU1, the product of the du1 gene, and the other is zSSI, the product of the Ss1 cDNA.

EXAMPLE 24

Increased Total SS Activity in Du1-mutant Extracts

Figure 12:
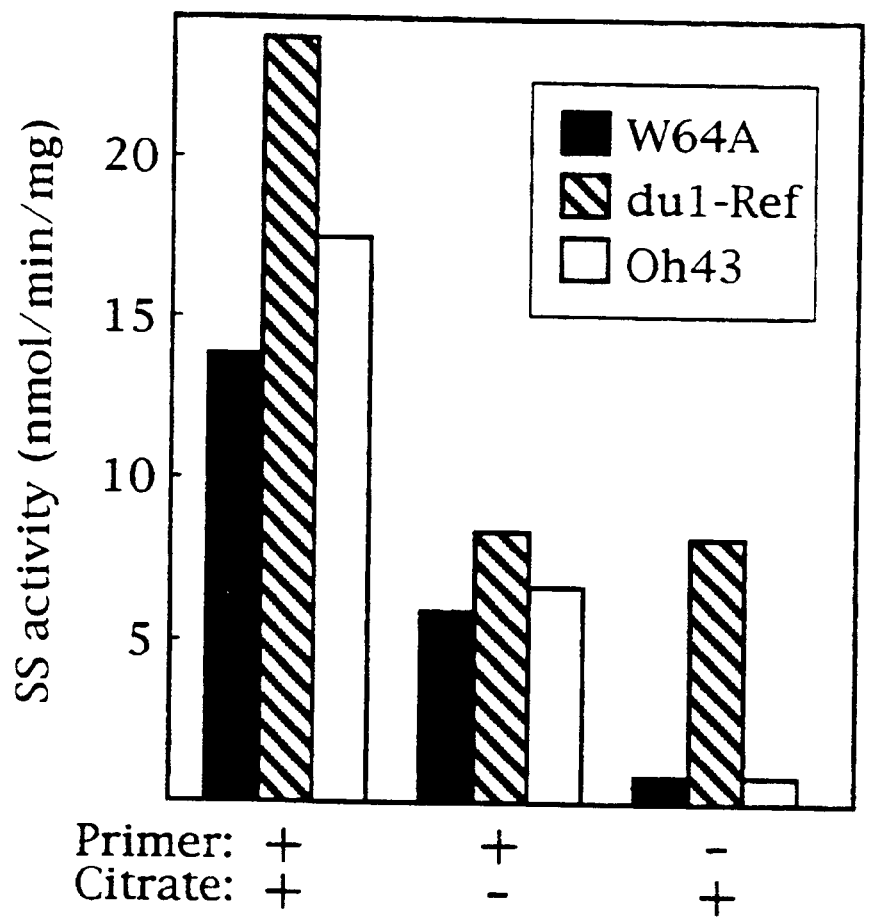
FIG. 12 shows the SS activity in total soluble kernel extracts. Total soluble extracts from kernels of the indicated genotype collected 20 DAP were assayed for SS activity in the presence or absence of exogenous primer (10 mg/mL glycogen) and 0.5 M citrate, as indicated. The du1-Ref mutant was in the W64A genetic background.

The conclusion that du1 specifies a SS disagrees with previous results indicating soluble SS activity is not decreased in a du1-mutant. In that study the total soluble SS activity was reported to be increased approximately 2-fold in du1-Ref mutant extracts; this observation was repeated independently in the current study (FIG. 12). Congenic strains were analyzed, ruling out genetic background differences as the explanation for the different total SS levels. A possible explanation for this phenomenon is that a SS other than DU1 is hyperactive in du1-mutants. To test this possibility SS activity in total soluble kernel extracts was assayed in the presence or absence of citrate and/or exogenous glucan primer. These experiments were intended to differentiate between zSSI, which is known to be stimulated significantly by citrate and be independent of exogenous primer, and SSII which is primer-dependent and largely citrate-independent.

Citrate-stimulated, primer-independent SS activity was increased approximately 8-fold in du1-Ref mutant extracts compared to congenic nonmutant extracts (FIG. 12). Similar results were obtained for six other du1-mutants. The immunodepletion data described above indicate that the only SS remaining in du-mutants is zSSI (FIG. 10). Thus, it appears that the activity of zSSI is increased in du1- mutants. Stimulation of zSSI activity cannot be explained simply by increased enzyme abundance, because immunoblot analysis revealed that the zSSI level was nearly the same in du1-Ref mutant extracts as in nonmutant extracts (FIG. 9A).

To understand the mechanisms of starch biosynthesis one must identify the SS isozymes active at each stage of endosperm development. Multiple soluble SSs are present in endosperm, as shown initially by biochemical fractionation. Two activity peaks were observed, designated SSI, which does not require exogenous glucan primer and is stimulated by citrate, and SSII, which is dependent on exogenous primer and largely insensitive to citrate. Five different cDNA clones are known that code for SSs, however, so it is necessary to correlate each enzymatic activity with a particular genetic element.

The cDNA that codes for zSSI was identified recently, however, the protein(s) responsible for the second SS activity had not been clearly assigned prior to this study. zSSI associates with an apparent 76 kD protein. Sequence comparison indicated the Ss1 cDNA codes for this polypeptide, and this cDNA directs expression of an active SS that is immunologically cross-reactive with zSSI. Thus, the genetic element responsible for synthesis of zSSI is now identified. Presumably at least one additional protein also provides a distinct SS activity in the soluble fraction, because of the enzymatic characteristics and apparent molecular weight of SSII. Detailed characterization of this second enzyme is lacking because it has proven difficult to purify.

The gene du1 was proposed to code for a soluble SS activity based in part on the facts that du1-mutants lack SSI and that Du1 codes for a protein similar in sequence to known SSs. This study confirms the identification of DU1 as an active SS. Expression of the DU1C terminus correlated with induction of SS activity, and DU1-specific antibodies immunodepleted a significant portion of the enzyme present in kernel extracts. Furthermore, a specific SS enzyme activity identified by zymogram analysis migrated in SDS-PAGE at the same rate as DU1 and was missing in a du1-mutant. Taken together these data identify a second genetic element that specifies a soluble SS. The SS activity of DU1 resides within the C terminal 450 residues; the functions of the remaining 1224 residues remain to be determined.

Inferences drawn from the immunodepletion data presume that anti-DU1N is specific for DU1. Immunologic specificity was indicated by three observations. First, in immunoblot analysis anti-DU IN failed to detect zSSI (and anti-SSI failed to detect DU1). Secondly, when du1-mutant extracts were treated with anti-DU1N there was no decrease in residual SS activity, even though anti-SSI treatment of the same extracts reduced the activity almost completely. Thus anti-DU1N does not neutralize zSSI. Thirdly, the anti-DU1 and anti-SSI immunoprecipitates were analyzed by immunoblotting using both antisera; the anti-DU1N complexes did not contain zSSI, and visa versa.

DU1 and zSSI most likely account for almost all of the soluble SS activity in developing kernels. Two enzymes were observed in zymograms, and each of these could be correlated with either DU1 or zSSI. Mutation of du1 completely eliminated the larger of the two SSs, and treating extracts with anti-SSI eliminated almost all of the remaining soluble SS activity. Although unlikely, the possibility remains that anti-SSI immunodepletes more than one isozyme. Any additional isozymes, however, would have to co-migrate with zSSI in the zymogram gels or fail to renature after SDS-PAGE. Furthermore, antibodies reactive with either of the remaining known SSs, zSSIIa or zSSIIb fail to detect polypeptides in soluble extracts of 20 DAP kernels. zSSIIa and zSSIIb, therefore, provide at most minor activities at this developmental stage, possibly accounting for the residual SS that is not eliminated by anti-SSI and a du1-mutation combined. Evolutionary sequence conservation of zSSIIa and zSSIIb with pea and potato SSII, however, suggests that despite their low level of expression these two enzymes are likely to provide specific functions in starch biosynthesis.

The present study suggests that DU1 accounts for the SSII enzyme activity. There are two SS peaks in anion exchange chromatography and two enzymes in the zymograms, which is most simply explained by a direct correspondence. Such a correspondence is further indicated by molecular weight comparisons: immunoblots indicated DU1 is greater than 200 kD, and native SSII in one study was estimated to be 180 kD. The >200kD protein detected by anti-DU1N was not present in du1-mutants. Most tellingly, zymogram analysis revealed the existence of a >200 kD SS that is missing in du1-mutants, as is the case also for the SSII chromatography fraction. All of these diverse observations can be explained by identity between DU1 and SSII.

Assignment of DU1 as a soluble protein of >200 kD was supported in an independent study. A polypeptide of this size was absent from the purified amyloplast stromal fraction of a du1-mutant. This protein most likely is the same one as the >200 kD SS and >200 kD anti-DU1N-reactive protein shown here to be absent in du1-kernels. Taken together these data indicate that DU1, as expected, is located within plastids.

The proteolytically labile nature of DU1 may explain the facts that purification of native SSII has been problematic and different molecular weights of 180 kD and 90 kD have been reported. Immunoblot analysis typically detects DU1 as a series of bands with the largest migrating at >200kD (FIG. 9), suggestive of proteolytic degradation. Incubation of kernel extracts lacking proteinase inhibitors at 0° C. for as few as 2 hours resulted in nearly complete loss of the full-length DU1 immunoblot signal, again indicating rapid proteolysis. Full-length DU1 expressed in $E.$ $coli$ also was unstable, even when cells were homogenized in the presence of protease inhibitors or lysed directly in SDS-PAGE loading buffer. This phenomenon might be an inherent property of DU1 owing to its large size, low pI of 4.74, and/or uneven charge distribution (e.g., DU1 residues 1–648 have a net charge of –50 and a pI of 4.45, whereas the DU1C fragment has a net charge of –2 and a pI of 7.30). The low overall pI of DU1 compares to values from 6.14–6.98 for other maize SSs. The amount of SS activity depleted by anti-DU1 sera might underestimate the prevalence of DU1 in vivo, again because of susceptibility to proteolysis.

DU1 and zSSI share the property that their mobility in SDS-PAGE is slower than predicted from their cDNA sequence. The Ss1 cDNA predicts a 64 kD protein, whereas zSSI runs in gels at 76 kD. The Du1 cDNA predicts a 188 kD protein, however, DU1 in kernel extracts runs significantly slower than the 200 kD marker. Anomalous migration in SDS-PAGE is thought to be an intrinsic property of zSSI and other SSs. The same phenomenon may apply to DU1, or it could be post-translationally modified.

Removal of DU1 from the soluble endosperm fraction apparently causes some change that results in increased activity of zSSI. A possible explanation is that DU1 deficiency causes accumulation of a glucan not present normally, and this provides an efficient primer for the zSSI. This observation explains the fact that total SS activity is not reduced in du1-mutant extracts even though a specific SS isozyme is lacking.

Comparison of DU1 to 27 other SS or GS sequences identified conserved residues that may provide clues regarding the enzymatic mechanisms of α-(1→4) bond formation. Thirty three residues are conserved in all 28 sequences, suggesting they are important for enzyme function either because they are located within the active site or are required for maintenance of catalytic structure. Motif I contains the conserved KT(S)GGL sequence in which the lysine and both glycines are thought to have specific functions in catalysis. This motif is present in all known glucosyltransferases, as well as other enzymes known to bind ADPG such as the amyloplast envelope transport protein BT1. Enzymes of the SSIII class, including DU1, are unique among SSs because the second residue of motif I is a variant valine, and that the sequence KTGGL occurs in motif VIII. The KTGGL sequence also occurs in motif VIII of several procaryotic glycogen synthases. Although the function of motif VIII remains to be determined, these data suggest the possibility that in the SSIII class it also is an ADPG binding site.

Motif IV contains a conserved lysine residue that in $E.$ $coli$ GS is known to be involved in catalysis. This lysine occurs in proximity to several other highly conserved residues in motif IV. Motif VII contains the only cysteine that is conserved in all 28 enzymes, which suggests it is involved in ADPG binding. Chemical modification studies indicated a cysteine residue mediates ADPG binding in $E.$ $coli$ GS. In that study cysteine was also implicated in glucan binding, however, other starch binding enzymes such as BEs and DBEs do not contain a conserved cysteine. Thus, the cysteine residue in motif VII may form part of the ADPG binding site. Finally, the conserved arginine in motif V is proposed be involved in starch binding. All the starch-binding enzymes of the α-amylase superfamily, including BEs and DBEs, contain a conserved arginine followed by a hydrophobic residue. Chemical modification studies indicated an arginine is involved in glucan binding by maize BEs, so this function is suggested also for the arginine of motif V in the glucan synthases.

The reason that multiple soluble SSs are utilized in storage starch biosynthesis is not known at present. DU1 clearly is distinct from zSSI in that it is located almost entirely within the soluble phase of endosperm cells, whereas zSSI is abundant in both the granule and soluble fractions (FIG. 9B). The fact that du1-mutations alter starch structure indicates DU1 provides a specific function(s) that cannot be compensated for by zSSI. Similarly, severe reduction of potato SSIII by antisense RNA expression causes significant changes in granule structure that cannot be compensated for by the remaining soluble SS activity. Although the specific functions of each soluble SS remain to b e determined, identification of the genetic sources of the two major isoforms in maize will provide new tools for such investigations.

The following references were cited herein:

Abel, G. J. W. et al. (1996). Plant J. 10, 981–991.
Ausubel, F. M. et al (1989). Current Protocols in Molecular Biology. (NY: John Wiley and Sons).
Bae, J. M. et al. (1990) Maydica 35, 317–322.
Ball, S. et al. (1996). Cell 86, 349–352.
Barker, R. F. et al. (1984). Nucl. Acids Res. 12, 5955–5967.
Beavis, et al. (1995). Maize Genet. Coop. Newsl. 69, 182–184.
Bhave, M. R. et al. (1990). Plant Cell 2, 581–588.
Boyer, C. D. et al. (1977). Amer. J. Bot. 64, 50–56.
Boyer, C. and Preiss, J. (1978a). Carbohydr. Res. 61, 321–334.
Boyer, et al. (1978b). Biochem. Biophys. Res. Commun. 80, 169–175.
Boyer, et al. (1981). Plant Physiol. 67, 1141–1145.
Boyer, C. D. et al. (1976). Cereal Chem. 53, 327–337.
Buléon, et al. (1997). *Plant Physiol.* 115, 949–957.
Cameron, J. W. (1947). Genetics 32, 459–485.
Cao, H. and Preiss, J. (1996) *J Protein Chem* 15, 291–304.
Chou, P. Y., and Fasman, G. D. (1978). In Advances in Enzymology, A. Meister, ed (NY: John Wiley and Sons), pp. 45–148.
Church, et al. (1984). Proc. Natl. Acad. Sci. 81, 1991–1995.
Creech, R. G. (1965). Genetics 52, 1175–1186.
Creech, R. G., and McArdle, F. J. (1966). Crop Sci. 6, 192–194.
Dang, et al. (1988). Phytochemistry 27, 1255–1259.
Davis, J. H. et al. (1955). Argon. J. 232–235.

Dvonch, W. et al. (1951). Cereal Chem. 28, 270–280.
Fisher, D. K. et al. (1993). Plant. Phsiol. 102, 1045–1046.
Fisher, D. K. et al. (1996). Plant Physiol. 110, 611–619.
Fisher, D. K. et al. (1995). Plant Physiol. 108, 1314–1314.
Fontaine, T. et al. (1993). J. Biol. Chem. 268, 16223–16230.
French, D. (1984). In Starch: Chemistry and technology, R. L. Whitaker, ed (Orlando: Academic Press), pp. 183–248.
Gao, M. et al. (1996). Plant Mol. Biol. 30, 1223–1232.
Gao, M. et al. (1997). Plant. Physiol. 114, 69–78.
Garnier, J. R. et al. (1978). J. Mol. Biol. 120, 97–120.
Giroux, M. J. et al. (1994). Plant Physiol. 106, 713–722.
Hannah, L. C. et al. (1993). Sci. Hortic. 55, 177–197.
Inouchi, N. et al. (1987). Starch/Staerke 39, 259.
James, M. G. et al. (1995). Plant Cell 7, 417–429.
Jespersen, H. M. (1993). J. Prot. Chem. 12, 791–805.
Jones, R. J. et al. (1996). Crop Sci. 36, 301–306.
Klösgen, R. B. et al. (1986). Mol. Gen. Genet. 203, 237–244.
Konat, G. W. et al. (1994). In PCR Technology, Current Innovations, (Boca Raton, Fla.: CRC Press), pp. 37–42.
Kuriki, T. et al. (1996). J. Prot. Chem. 15, 305–313.
Lewin, B. (1997). Genes VI. (Oxford: Oxford Univ. Press).
Mangelsdorf, P. C. (1947). Genetics 32, 448–458.
Manners, D. J. (1989). Carbohydrate Polymers 11, 87–112.
Marshall, J. et al. (1996). Plant Cell 8, 1121–1135.
Martin, C., and Smith, A. M. (1995). Plant Cell 7, 971–985.
Mitchell, J. P., and Tjian, R. (1989). Science 245, 371–378.
Mu, C. et al. (1994). Plant J. 6, 151–159.
Nelson, et al. (1995). Ann. Rev. Plant. Phys. Plant Mol. Biol. 46, 475–496.
Ozbun, J. L. et al. (1971). Plant Physiol. 78, 765–769.
Preiss, J. (1991). Oxford surveys of plant molecular and cell biology 7, 59–114.
Preiss, J., and Sivak, M. (1996). In Photoassimilate Distribution in Plants and Crops, (NY: M. Dekker, Inc.), pp. 63–96.
Robertson, D. S. (1978). Mutat.Res. 51, 21–28.
Sambrook, J. et al. (1989). Molecular Cloning. A Laboratory Manual. (Plainview, N.Y.: Cold Spring Harbor Laboratory Press).
Shannon, J.C., and Garwood, D.L. (1984). In Starch. Chemistry and Technology, (San Diego: Academic Press, Inc.), pp. 25–86. Shure, M. et al. (1983). Cell 35, 225–233.
Smith, A. et al. (1996). Annu. Rev. Plant Physiol. Plant Mol. Biol. 48, 67–87.
Smith, G. P. (1976). Science 191, 525–535.
Stinard, P. S. et al. (1993). Plant Cell 5, 1555–1566.
Takeda, et al. (1993). Carbohydr. Res. 240, 253–363.
Wang, Y.-J. et al. (1993a). Cereal Chem. 70, 521–525.
Wang, Y.-J. et al. (1993b). Cereal Chem 70, 171–179.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

SEQUENCE LISTING

```
<160> NUMBER OF SEQ ID NOS: 37

<210> SEQ ID NO 1
<211> LENGTH: 6027
<212> TYPE: DNA
<213> ORGANISM: maize
<220> FEATURE:
<223> OTHER INFORMATION: cDNA sequence corresponding to the gene
      encoding the starch synthase enzyme DU1.

<400> SEQUENCE: 1
gaattcccta gttcagagaa agaaagaagt tgagaatgag aagcaagtga ggcgcgtttg      60
ctgggaagtg gttcttgtga ggtttaggag ttcacccttc ttttcttccc cttctagaaa     120
tggagatggt cctacggtcg cagagccctc tctgccttcg gagtgggccg gtgctcattt     180
ttcgaccaac cgtcgcgggc ggaggagggg gcactcagtc tttgttgagg actaccagat     240
ttgcgagaag aagggtcatt cgatgcgttg tagcaagtcc aggttgtcct aataggaaat     300
ctaggacagc gtctcccaac gtaaaagtag ctgcttatag caactatgcg ccaagactcc     360
tcgttgagtc aagctccaag aagagcgaac accatgatag cagcagacac cgtgaagaaa     420
ctattgtaca atacaatggg ctgtcaggtt ctgatgcagc agaattgaca agtaatagag     480
atgtagaaat tgaagtggat ttgcagcaca tttctgagga ggaattgcca ggaaaagtat     540
cgattaatgc atcattagga gaaatggaaa cagtggatga agctgaggtc gaggaggata     600
```

-continued

```
agtttgaggt agatacctca ggaattgtat tgcgcaatgt tgcagttcgg gaagtggatc      660
caaaggatga acataatgct aaagatgtat ttgtggtaga ttcgtcagga actgcaccag      720
ataatgctgc agtggaggaa gtggtagatg aagctgaggt tgaagaggat atggttgatg      780
tggatatctt gggacttgac ttgaataatg caacgatcga ggaaattgat ttgatggaag      840
aggctttact ggagaacttc gacgtggatt caccaggcaa tgcttctagt ggtcgaacct      900 atggggtgt ggatgagttg ggtgagctgc cttcaacatc cgtggattgc atcgccatta      960
acggaaaacg tagaagtttg aagcctaagc ccttgccaat tgtcaggttc caggaacaag     1020
aacagatagt tttaagcatt gttgacgaag aagggttgat tgctagttca tgtgaagaag     1080
gccaaccggt ggtagattac gataagcaag aggaaaactc taccgctttc gatgaacaga     1140
agcaattaac tgatgatttc cctgaagaag gcatatctat agttcacttc cctgagccaa     1200
acaatgatat tgttggatcc tcaaaattct tggagcaaaa acaagaattg gatggttctt     1260
ataaacaaga tcgatcaacc actggattgc atgaacaaga tcagtctgtt gttagttcac     1320
acggacaaga taaatcaatt gttggtgtgc ctcagcaaat ccagtacaat gatcaatcta     1380
ttgctggttc tcatagacaa gatcaatcaa ttgccggtgc acctgagcaa atccaatccg     1440
ttgctggcta tataaaacca aatcaatcta ttgttggttc ttgtaaacaa catgaattga     1500
ttattcctga gcctaagaaa atcgaatcca tcatcagtta caatgaaata gatcaatcta     1560
ttgttggttc tcacaaacaa gacaaatctg ttgttagtgt gcctgagcaa atccaatcca     1620
ttgttagtca cagcaaacca aatcaatcta ctgttgattc ttatagacaa gctgaatcaa     1680
ttattggtgt gcctgagaaa gtccaatcca tcaccagtta cgataaacta gaccagtcca     1740
ttgttggttc tcttaaacaa gatgagccta ttattagcgt gcctgagaaa atccaatcca     1800
ttgtccatta cactaaacca aatcagtcta ttgttggctt gcccaaacaa caacaatcaa     1860
ttgttcatat cgttgaacca aaacagtcca tagatggttt ccctaaacaa gatctatcaa     1920
tcgttggtat ctccaatgag tttcaaacaa agcaactggc tactgttggg actcatgatg     1980
gattgcttat gaagggtgtg gaagctaagg agacatctca aaagactgaa ggggatacac     2040
ttcaggcaac gttcaatgtc gacaacttgt cacagaaaca ggaaggctta actaaagaag     2100
cagacgagat aacaattatt gagaaaatca atgatgaaga ccttgtgatg attgaagaac     2160
agaaaagcat agccatgaat gaagaacaga cgattgttac cgaagaagac attccaatgg     2220
ctaaggttga gataggaatt gacaaggcca aatttttaca tctgctttct gaagaagaga     2280
gttcatggga tgaaaatgaa gtgggaataa ttgaggctga tgaacagtat gaagtcgatg     2340
agacatctat gtccactgaa caagatatcc aggaatcacc taatgatgat ttggatccac     2400
aagcactatg gagtatgctt caagagcttg ctgaaaaaaa ttattcgctg ggaaacaagt     2460
tgtttactta tccagatgta ttgaaagctg attcaacaat tgatctctat ttcaatcgtg     2520
atctatcagc tgtggccaat gagcctgatg tacttatcaa aggagcattc aatgggtgga     2580
agtggagatt tttcactgaa aaattgcaca agagcgagct ggcagggac tggtggtgct     2640 gcaaactata cattcctaag caggcataca gaatggactt tgtgttttt aacggacaca     2700 cggtatatga aaataataac aataatgatt tcgtgataca aatagaaagc accatggatg     2760
aaaatttatt tgaggatttc ttggctgaag aaaagcaacg agaacttgag aaccttgcaa     2820
atgaggaagc tgaaaggagg agacaaactg atgagcagcg gcgaatggag gaagaaaggg     2880
ccgcagataa agctgacagg gtacaagcca aggttgaggt agagacgaag aagaataaat     2940
```

-continued

| | |
|---|---|
| tgtgcaatgt attgggttta gccagagctc ctgttgataa tttatggtac attgagccca | 3000 |
| tcacgactgg acaagaggct actgtcagat tgtattataa cataaactca agacctctag | 3060 |
| ttcacagtac tgagatatgg atgcatggtg gctataacaa ttggattgat ggactctctt | 3120 |
| ttgctgaaag gcttgttcat catcatgaca aagattgtga ttggtggttt gcagatgttg | 3180 |
| tcgtgcctga aagaacatat gtattggact ggggttttgc tgacggccca ccagggagtg | 3240 |
| caaggaatta tgacaacaat ggaggacatg attttcatgc taccctccta aataacatga | 3300 |
| ctgaggaaga gtattggatg gaagaagaac aaaggatcta acaaggctt caacaagaga | 3360 |
| ggagggaaag ggaggaggct attaaaagga aggctgagag aaatgcaaaa atgaaagctg | 3420 |
| agatgaagga aaagactatg agaatgttcc tggtttctca gaaacacatt gtttacaccg | 3480 |
| aaccacttga aatacatgct ggaactacta ttgatgtgct ttataatcct tctaatacag | 3540 |
| ttctaactgg aaagccagag gtttggtttc gatgttcctt taatcgttgg atgtatccag | 3600 |
| gtggggtgtt gccacctcag aagatggtac aagcagaaaa tggttcacac ctaaaagcaa | 3660 |
| cagtttacgt tccacgagat gcctatatga tggacttcgt tttctcggag tcagaagaag | 3720 |
| gtggaattta tgataacaga aatgggttag actatcatat tcctgttttt gggtcaattg | 3780 |
| caaaggaacc acctatgcac attgtccaca ttgctgttga gatggcacca atcgcaaagg | 3840 |
| ttggaggtct tggtgatgtt gtcactagtc tttcacgtgc tgtgcaagat ttaggacaca | 3900 |
| atgtggaggt tattcttcca aagtacggtt gcttgaatct aagcaatgtc aagaatctac | 3960 |
| aaatccatca gagtttttct tggggtggtt ctgaaataaa tgtgtggcgt ggactagtcg | 4020 |
| aaggcctttg tgtttacttc ctggaacctc aaaatgggat gtttggagtc ggatatgtat | 4080 |
| atggcaggga cgatgaccgc cgatttggct tcttctgtcg ttctgctcta gagtttctcc | 4140 |
| tccaaagtgg atcttctccg aacataatac attgccatga ttggtcaagt gctcctgttg | 4200 |
| cctggctaca caaggaaaac tacgcgaagt ctagcttggc aaacgcacgg gtggtattca | 4260 |
| ccatccacaa tcttgaattt ggagcgcatc atattggcaa agcaatgaga tattgtgata | 4320 |
| aagcaacaac tgtctctaat acatattcaa aggaagtgtc aggtcatggt gccatagttc | 4380 |
| ctcatcttgg gaaattctat ggcattctca atggaattga tccggatata tgggatccgt | 4440 |
| acaatgacaa ctttatcccg gtccactaca cttgtgagaa tgtggttgaa ggcaagaggg | 4500 |
| ctgctaagag ggcactgcag cagaagtttg ggttacagca aatcgatgtc cccgtcgtag | 4560 |
| gaatcgtcac tcgcctgaca gcccaaaagg ggatccacct gatcaagcat gcgattcacc | 4620 |
| gtacactcga acggaacgga caggtggttt tgcttggttc agcgccggac tctcgaatcc | 4680 |
| aagctgattt tgtcaacctg gcgaatacgc tccacggcgt aaaccatggg caagtgaggc | 4740 |
| tttccttgac ctacgacgag cctctctcgc atctgatata cgctggctct gacttcattc | 4800 |
| tggtcccatc tatatttgag ccttgcggcc taactcagct cgtcgccatg cggtatggaa | 4860 |
| ccatcccgat tgtccgcaag actggagggc tcttcgacac tgtcttcgat gtggacaatg | 4920 |
| acaaggaacg agcccgagat cgaggccttg agcccaacgg gtttagcttt gacggagctg | 4980 |
| atagcaacgg tgttgactac gcgctgaaca gggcgatctc agcttggttc gatgcccgga | 5040 |
| gctggttcca ctcccttttgc aagagagtca tggagcagga ctggtcgtgg aaccgacctg | 5100 |
| ccctcgacta catcgagctc taccgttcag cgtccaaatt gtaataatcc aaacaacggc | 5160 |
| caatgtagtg tgttgtctgc aggtctcaga tgcagccatt cagcttttgc aggttcctgg | 5220 |
| gcattgctgt acagcctcct tgtctttagt tagctccatt ccccgaggag cacagtgcaa | 5280 |
| tttttttatcc tcagttatta tgcatagatt gtctcagtag aatgctttct tcgggcatgt | 5340 |

-continued

```
atgtttgttt cctctgttgt tgaattctgg tgttaagtcg cgtataggaa tctacaggaa    5400
atgaaaaagt ccatttcctg cgtcaacctt ttagggctac catgcacatg agacctttca    5460
agtgcaaaga atattaggac tagactacta gtatgtgaac tctattttc caagagattt     5520 caattttcc aatgaaaaat aaactaattt ttcttggaaa aatggaaatc ccttggaaaa     5580
atggggttcc caaactagcc cgtagagtat agatcataga attggtctag tggttcctcg    5640
agagagaaaa aaacatagac ttttcttgtc atatgcttat ttaagtttat tttgtacaaa    5700
ctttgagaac cttcaaaaac accccaatgg ctggttaagt gaccagggaa ataaagagga    5760
tctataggga ggaatccccc gcctctctct cacagatgtt gcctagcacc ggccagcctc    5820
atccgtccag tggaattaag gttggttgcg acgacagccc atcaatggaa accaacctcg    5880
tgccccgtgc cgggatctac cttccttcct caccaccacg ccgatctcac cttccatagg    5940
agcttcctat gcactgttac ctattatagg tacatgacat tgtacatctt tgtatgaact    6000
tacatcaatg ccaaaaatcc ggaattc                                        6027
```

<210> SEQ ID NO 2
<211> LENGTH: 21
<212> TYPE: DNA
<213> ORGANISM: artificial sequence
<220> FEATURE:
<221> NAME/KEY: primer_bind
<223> OTHER INFORMATION: Primer du1-sp1 used to amplify fragment F500
      from pJW3

<400> SEQUENCE: 2
gtacaatgac aactttatcc c                                              21

<210> SEQ ID NO 3
<211> LENGTH: 23
<212> TYPE: DNA
<213> ORGANISM: artificial sequence
<220> FEATURE:
<221> NAME/KEY: primer_bind
<223> OTHER INFORMATION: Primer du1-sp2 used to amplify fragment F500
      from pJW3

<400> SEQUENCE: 3
cattctcaca agtgtagtgg acc                                            23

<210> SEQ ID NO 4
<211> LENGTH: 20
<212> TYPE: DNA
<213> ORGANISM: artificial sequence
<220> FEATURE:
<221> NAME/KEY: primer_bind
<223> OTHER INFORMATION: Primer du1-sp4 used to amplify cloned BamHI
      fragment.

<400> SEQUENCE: 4
gtcgtaggaa tcgtcactcg                                                20

<210> SEQ ID NO 5
<211> LENGTH: 20
<212> TYPE: DNA
<213> ORGANISM: artificial sequence
<220> FEATURE:
<221> NAME/KEY: primer_bind
<223> OTHER INFORMATION: (1030 primer located 19 bp proximal to EcoRI
      cloning site in the left arm in (gt11 phage DNA used to amplify
      cDNA inserts

<400> SEQUENCE: 5

```
attggtggcg acgactcctg                                               20

<210> SEQ ID NO 6
<211> LENGTH: 20
<212> TYPE: DNA
<213> ORGANISM: artificial sequence
<220> FEATURE:
<221> NAME/KEY: primer_bind
<223> OTHER INFORMATION: (1356 primer located 281 bp distal to EcoRI
      cloning site in the LacZ' region in the right arm in (gt11 phage
      DNA used to amplify cDNA inserts.

<400> SEQUENCE: 6
gtgtgggggt gatggcttcc                                               20

<210> SEQ ID NO 7
<211> LENGTH: 20
<212> TYPE: DNA
<213> ORGANISM: artificial sequence
<220> FEATURE:
<221> NAME/KEY: primer_bind
<223> OTHER INFORMATION: Primer du-F3 used to amplify Du1 mRNA

<400> SEQUENCE: 7
ataaatgtgt ggcgtggact                                               20

<210> SEQ ID NO 8
<211> LENGTH: 20
<212> TYPE: DNA
<213> ORGANISM: artificial sequence
<220> FEATURE:
<221> NAME/KEY: primer_bind
<223> OTHER INFORMATION: Primer du-R1 used to amplify Du1 mRNA

<400> SEQUENCE: 8
cgttccttgt cattgtccac                                               20

<210> SEQ ID NO 9
<211> LENGTH: 6
<212> TYPE: PRT
<213> ORGANISM: maize
<220> FEATURE:
<222> LOCATION: REPEAT
<223> OTHER INFORMATION: Six residue M-box sequence in first half-repeat
      of ten residue sequence of SBE-repeat in DU1.

<400> SEQUENCE: 9

Asp Gln Ser Ile Val Gly
 1               5

<210> SEQ ID NO 10
<211> LENGTH: 4
<212> TYPE: PRT
<213> ORGANISM: maize
<220> FEATURE:
<222> LOCATION: REPEAT
<223> OTHER INFORMATION: Four residue sequence of second half-repeat of
      ten residue SBE-repeat sequence in DU1.

<400> SEQUENCE: 10

Ser His Lys Gln
 1

<210> SEQ ID NO 11
<211> LENGTH: 6
<212> TYPE: PRT
<213> ORGANISM: unknown
```

```
<220> FEATURE:
<222> LOCATION: REPEAT
<223> OTHER INFORMATION: M-box sequence in SBEI enzyme.

<400> SEQUENCE: 11

Asp Gln Ala Leu Val Gly
 1               5

<210> SEQ ID NO 12
<211> LENGTH: 1674
<212> TYPE: PRT
<213> ORGANISM: maize
<220> FEATURE:
<223> OTHER INFORMATION: Deduced amino acid sequence of starch synthase
      DU1.

<400> SEQUENCE: 12

Met Glu Met Val Leu Arg Ser Gln Ser Pro Leu Cys Leu Arg Ser
 1               5                  10                  15

Gly Pro Val Leu Ile Phe Arg Pro Thr Val Ala Gly Gly Gly Gly
                20                  25                  30

Gly Thr Gln Ser Leu Leu Arg Thr Thr Arg Phe Ala Arg Arg Arg
                35                  40                  45

Val Ile Arg Cys Val Val Ala Ser Pro Gly Cys Pro Asn Arg Lys
                50                  55                  60

Ser Arg Thr Ala Ser Pro Asn Val Lys Val Ala Ala Tyr Ser Asn
                65                  70                  75

Tyr Ala Pro Arg Leu Leu Val Glu Ser Ser Lys Lys Ser Glu
                80                  85                  90

His His Asp Ser Ser Arg His Arg Glu Glu Thr Ile Asp Thr Tyr
                95                 100                 105

Asn Gly Leu Ser Gly Ser Asp Ala Ala Glu Leu Thr Ser Asn Arg
               110                 115                 120

Asp Val Glu Ile Glu Val Asp Leu Gln His Ile Ser Glu Glu Glu
               125                 130                 135

Leu Pro Gly Lys Val Ser Ile Asn Ala Ser Leu Gly Glu Met Glu
               140                 145                 150

Thr Val Asp Glu Ala Glu Val Glu Glu Asp Lys Phe Glu Val Asp
               155                 160                 165

Thr Ser Gly Ile Val Leu Arg Asn Val Ala Val Arg Glu Val Asp
               170                 175                 180

Pro Lys Asp Glu His Asn Ala Lys Asp Val Phe Val Asp Ser
               185                 190                 195

Ser Gly Thr Ala Pro Asp Asn Ala Ala Val Glu Glu Val Val Asp
               200                 205                 210

Glu Ala Glu Val Glu Glu Asp Met Val Asp Val Asp Ile Leu Gly
               215                 220                 225

Leu Asp Leu Asn Asn Ala Thr Ile Glu Glu Ile Asp Leu Met Glu
               230                 235                 240

Glu Ala Leu Leu Glu Asn Phe Asp Val Asp Ser Pro Gly Asn Ala
               245                 250                 255

Ser Ser Gly Arg Thr Tyr Gly Gly Val Asp Glu Leu Gly Glu Leu
               260                 265                 270

Pro Ser Thr Ser Val Asp Cys Ile Ala Ile Asn Gly Lys Arg Arg
               275                 280                 285

Ser Leu Lys Pro Lys Pro Leu Pro Ile Val Arg Phe Gln Glu Gln
               290                 295                 300
```

```
Glu Gln Ile Val Leu Ser Ile Val Asp Glu Gly Leu Ile Ala
            305                 310                 315
Ser Ser Cys Glu Glu Gly Gln Pro Val Asp Tyr Asp Lys Gln
            320                 325                 330
Glu Glu Asn Ser Thr Ala Phe Asp Gln Lys Gln Leu Thr Asp
            335                 340                 345
Asp Phe Pro Glu Glu Gly Ile Ser Ile Val His Phe Pro Glu Pro
            350                 355                 360
Asn Asn Asp Ile Val Gly Ser Ser Lys Phe Leu Glu Gln Lys Gln
            365                 370                 375
Glu Leu Asp Gly Ser Tyr Lys Gln Asp Arg Ser Thr Thr Gly Leu
            380                 385                 390
His Glu Gln Asp Gln Ser Val Val Ser Ser His Gly Gln Asp Lys
            395                 400                 405
Ser Ile Val Gly Val Pro Gln Gln Ile Gln Tyr Asn Asp Gln Ser
            410                 415                 420
Ile Ala Gly Ser His Arg Gln Asp Gln Ser Ile Ala Gly Ala Pro
            425                 430                 435
Glu Gln Ile Gln Ser Val Ala Gly Tyr Ile Lys Pro Asn Gln Ser
            440                 445                 450
Ile Val Gly Ser Cys Lys Gln His Glu Leu Ile Ile Pro Glu Pro
            455                 460                 465
Lys Lys Ile Glu Ser Ile Ile Ser Tyr Asn Glu Ile Asp Gln Ser
            470                 475                 480
Ile Val Gly Ser His Lys Gln Asp Lys Ser Val Val Ser Val Pro
            485                 490                 495
Glu Gln Ile Gln Ser Ile Val Ser His Ser Lys Pro Asn Gln Ser
            500                 505                 510
Thr Val Asp Ser Tyr Arg Gln Ala Glu Ser Ile Ile Gly Val Pro
            515                 520                 525
Glu Lys Val Gln Ser Ile Thr Ser Tyr Asp Lys Leu Asp Gln Ser
            530                 535                 540
Ile Val Gly Ser Leu Lys Gln Asp Glu Pro Ile Ile Ser Val Pro
            545                 550                 555
Glu Lys Ile Gln Ser Ile Val His Tyr Thr Lys Pro Asn Gln Ser
            560                 565                 570
Ile Val Gly Leu Pro Lys Gln Gln Gln Ser Ile Val His Ile Val
            575                 580                 585
Glu Pro Lys Gln Ser Ile Asp Gly Phe Pro Lys Gln Asp Leu Ser
            590                 595                 600
Ile Val Gly Ile Ser Asn Glu Phe Gln Thr Lys Gln Leu Ala Thr
            605                 610                 615
Val Gly Thr His Asp Gly Leu Leu Met Lys Gly Val Glu Ala Lys
            620                 625                 630
Glu Thr Ser Gln Lys Thr Glu Gly Asp Thr Leu Gln Ala Thr Phe
            635                 640                 645
Asn Val Asp Asn Leu Ser Gln Lys Gln Glu Gly Leu Thr Lys Glu
            650                 655                 660
Ala Asp Glu Ile Thr Ile Ile Glu Lys Ile Asn Asp Glu Asp Leu
            665                 670                 675
Val Met Ile Glu Glu Gln Lys Ser Ile Ala Met Asn Glu Glu Gln
            680                 685                 690
```

-continued

```
Thr Ile Val Thr Glu Glu Asp Ile Pro Met Ala Lys Val Glu Ile
            695                 700                 705

Gly Ile Asp Lys Ala Lys Phe Leu His Leu Leu Ser Glu Glu Glu
            710                 715                 720

Ser Ser Trp Asp Glu Asn Glu Val Gly Ile Ile Glu Ala Asp Glu
            725                 730                 735

Gln Tyr Glu Val Asp Glu Thr Ser Met Ser Thr Glu Gln Asp Ile
            740                 745                 750

Gln Glu Ser Pro Asn Asp Asp Leu Asp Pro Gln Ala Leu Trp Ser
            755                 760                 765

Met Leu Gln Glu Leu Ala Glu Lys Asn Tyr Ser Leu Gly Asn Lys
            770                 775                 780

Leu Phe Thr Tyr Pro Asp Val Leu Lys Ala Asp Ser Thr Ile Asp
            785                 790                 795

Leu Tyr Phe Asn Arg Asp Leu Ser Ala Val Ala Asn Glu Pro Asp
            800                 805                 810

Val Leu Ile Lys Gly Ala Phe Asn Gly Trp Lys Trp Arg Phe Phe
            815                 820                 825

Thr Glu Lys Leu His Lys Ser Glu Leu Ala Gly Asp Trp Trp Cys
            830                 835                 840

Cys Lys Leu Tyr Ile Pro Lys Gln Ala Tyr Arg Met Asp Phe Val
            845                 850                 855

Phe Phe Asn Gly His Thr Val Tyr Glu Asn Asn Asn Asn Asn Asp
            860                 865                 870

Phe Val Ile Gln Ile Glu Ser Thr Met Asp Glu Asn Leu Phe Glu
            875                 880                 885

Asp Phe Leu Ala Glu Lys Gln Arg Glu Leu Glu Asn Leu Ala
            890                 895                 900

Asn Glu Glu Ala Glu Arg Arg Arg Gln Thr Asp Glu Gln Arg Arg
            905                 910                 915

Met Glu Glu Glu Arg Ala Ala Asp Lys Ala Asp Arg Val Gln Ala
            920                 925                 930

Lys Val Glu Val Glu Thr Lys Lys Asn Lys Leu Cys Asn Val Leu
            935                 940                 945

Gly Leu Ala Arg Ala Pro Val Asp Asn Leu Trp Tyr Ile Glu Pro
            950                 955                 960

Ile Thr Thr Gly Gln Glu Ala Thr Val Arg Leu Tyr Tyr Asn Ile
            965                 970                 975

Asn Ser Arg Pro Leu Val His Ser Thr Glu Ile Trp Met His Gly
            980                 985                 990

Gly Tyr Asn Asn Trp Ile Asp Gly Leu Ser Phe Ala Glu Arg Leu
            995                 1000                1005

Val His His His Asp Lys Asp Cys Asp Trp Trp Phe Ala Asp Val
            1010                1015                1020

Val Val Pro Glu Arg Thr Tyr Val Leu Asp Trp Val Phe Ala Asp
            1025                1030                1035

Gly Pro Pro Gly Ser Ala Arg Asn Tyr Asp Asn Asn Gly His
            1040                1045                1050

Asp Phe His Ala Thr Leu Pro Asn Asn Met Thr Glu Glu Tyr
            1055                1060                1065

Trp Met Glu Glu Glu Gln Arg Ile Tyr Thr Arg Leu Gln Gln Glu
            1070                1075                1080

Arg Arg Glu Arg Glu Glu Ala Ile Lys Arg Lys Ala Glu Arg Asn
```

-continued

```
                    1085                1090                1095
Ala Lys Met Lys Ala Glu Met Lys Glu Lys Thr Met Arg Met Phe
                1100                1105                1110
Leu Val Ser Gln Lys His Ile Val Tyr Thr Glu Pro Leu Glu Ile
                1115                1120                1125
His Ala Gly Thr Thr Ile Asp Val Leu Tyr Asn Pro Ser Asn Thr
                1130                1135                1140
Val Leu Thr Gly Lys Pro Glu Val Trp Phe Arg Cys Ser Phe Asn
                1145                1150                1155
Arg Trp Met Tyr Pro Gly Gly Val Leu Pro Pro Gln Lys Met Val
                1160                1165                1170
Gln Ala Glu Asn Gly Ser His Leu Lys Ala Thr Val Tyr Val Pro
                1175                1180                1185
Arg Asp Ala Tyr Met Met Asp Phe Val Phe Ser Glu Ser Glu Glu
                1190                1195                1200
Gly Gly Ile Tyr Asp Asn Arg Asn Gly Leu Asp Tyr His Ile Pro
                1205                1210                1215
Val Phe Gly Ser Ile Ala Lys Glu Pro Pro Met His Ile Val His
                1220                1225                1230
Ile Ala Val Glu Met Ala Pro Ile Ala Lys Val Gly Gly Leu Gly
                1235                1240                1245
Asp Val Val Thr Ser Leu Ser Arg Ala Val Gln Asp Leu Gly His
                1250                1255                1260
Asn Val Glu Val Ile Leu Pro Lys Tyr Gly Cys Leu Asn Leu Ser
                1265                1270                1275
Asn Val Lys Asn Leu Gln Ile His Gln Ser Phe Ser Trp Gly Gly
                1280                1285                1290
Ser Glu Ile Asn Val Trp Arg Gly Leu Val Glu Gly Leu Cys Val
                1295                1300                1305
Tyr Phe Leu Glu Pro Gln Asn Gly Met Phe Gly Val Gly Tyr Val
                1310                1315                1320
Tyr Gly Arg Asp Asp Asp Arg Arg Phe Gly Phe Phe Cys Arg Ser
                1325                1330                1335
Ala Leu Glu Phe Leu Leu Gln Ser Gly Ser Ser Pro Asn Ile Ile
                1340                1345                1350
His Cys His Asp Trp Ser Ser Ala Pro Val Ala Trp Leu His Lys
                1355                1360                1365
Glu Asn Tyr Ala Lys Ser Ser Leu Ala Asn Ala Arg Val Val Phe
                1370                1375                1380
Thr Ile His Asn Leu Glu Phe Gly Ala His His Ile Gly Lys Ala
                1385                1390                1395
Met Arg Tyr Cys Asp Lys Ala Thr Thr Val Ser Asn Thr Tyr Ser
                1400                1405                1410
Lys Glu Val Ser Gly His Gly Ala Ile Val Pro His Leu Gly Lys
                1415                1420                1425
Phe Tyr Gly Ile Leu Asn Gly Ile Asp Pro Asp Ile Trp Asp Pro
                1430                1435                1440
Tyr Asn Asp Asn Phe Ile Pro Val His Tyr Thr Cys Glu Asn Val
                1445                1450                1455
Val Glu Gly Lys Arg Ala Ala Lys Arg Ala Leu Gln Gln Lys Phe
                1460                1465                1470
Gly Leu Gln Gln Ile Asp Val Pro Val Val Gly Ile Val Thr Arg
                1475                1480                1485
```

```
Leu Thr Ala Gln Lys Gly Ile His Leu Ile Lys His Ala Ile His
            1490                1495                1500

Arg Thr Leu Glu Arg Asn Gly Gln Val Val Leu Leu Gly Ser Ala
            1505                1510                1515

Pro Asp Ser Arg Ile Gln Ala Asp Phe Val Asn Leu Ala Asn Thr
            1520                1525                1530

Leu His Gly Val Asn His Gly Gln Val Arg Leu Ser Leu Thr Tyr
            1535                1540                1545

Asp Glu Pro Leu Ser His Leu Ile Tyr Ala Gly Ser Asp Phe Ile
            1550                1555                1560

Leu Val Pro Ser Ile Phe Glu Pro Cys Gly Leu Thr Gln Leu Val
            1565                1570                1575

Ala Met Arg Tyr Gly Thr Ile Pro Ile Val Arg Lys Thr Gly Gly
            1580                1585                1590

Leu Phe Asp Thr Val Phe Asp Val Asp Asn Asp Lys Glu Arg Ala
            1595                1600                1605

Arg Asp Arg Gly Leu Glu Pro Asn Gly Phe Ser Phe Asp Gly Ala
            1610                1615                1620

Asp Ser Asn Gly Val Asp Tyr Ala Leu Asn Arg Ala Ile Ser Ala
            1625                1630                1635

Trp Phe Asp Ala Arg Ser Trp Phe His Ser Leu Cys Lys Arg Val
            1640                1645                1650

Met Glu Gln Asp Trp Ser Trp Asn Arg Pro Ala Leu Asp Tyr Ile
            1655                1660                1665

Glu Leu Tyr Arg Ser Ala Ser Lys Leu
            1670

<210> SEQ ID NO 13
<211> LENGTH: 60
<212> TYPE: PRT
<213> ORGANISM: maize
<220> FEATURE:
<221> NAME/KEY: 418..477
<222> LOCATION: REPEAT
<223> OTHER INFORMATION: First 60 amino acid residue SBE-superrepeat of
      180 amino acid repeat residue in DU1.

<400> SEQUENCE: 13

Asp Gln Ser Ile Ala Gly Ser His Arg Gln Asp Gln Ser Ile Ala
1               5                   10                  15

Gly Ala Pro Glu Gln Ile Gln Ser Val Ala Gly Tyr Ile Lys Pro
                20                  25                  30

Asn Gln Ser Ile Val Gly Ser Cys Lys Gln His Glu Leu Ile Ile
                35                  40                  45

Pro Glu Pro Lys Lys Ile Glu Ser Ile Ile Ser Tyr Asn Glu Ile
                50                  55                  60

<210> SEQ ID NO 14
<211> LENGTH: 60
<212> TYPE: PRT
<213> ORGANISM: maize
<220> FEATURE:
<221> NAME/KEY: 478..537
<222> LOCATION: REPEAT
<223> OTHER INFORMATION: Second 60 amino acid residue SBE-superrepeat of
      180 amino acid repeat residue in DU1.

<400> SEQUENCE: 14

Asp Gln Ser Ile Val Gly Ser His Lys Gln Asp Lys Ser Val Val
```

```
                 1               5                  10                 15
Ser Val Pro Glu Gln Ile Gln Ser Ile Val Ser His Ser Lys Pro
                        20                 25                 30

Asn Gln Ser Thr Val Pro Ser Tyr Arg Gln Ala Glu Ser Ile Ile
                        35                 40                 45

Gly Val Pro Glu Lys Val Gln Ser Ile Thr Ser Tyr Asp Lys Leu
                        50                 55                 60

<210> SEQ ID NO 15
<211> LENGTH: 60
<212> TYPE: PRT
<213> ORGANISM: maize
<220> FEATURE:
<221> NAME/KEY: 438..597
<222> LOCATION: REPEAT
<223> OTHER INFORMATION: Third 60 amino acid residue SBE-superrepeat of
      180 amino acid repeat residue in DU1.

<400> SEQUENCE: 15

Asp Gln Ser Ile Val Gly Ser Leu Lys Gln Asp Glu Pro Ile Ile
 1               5                  10                 15

Ser Val Pro Glu Lys Ile Gln Ser Ile Val His Tyr Thr Lys Pro
                        20                 25                 30

Asn Gln Ser Ile Val Gly Leu Pro Lys Gln Gln Gln Ser Ile Val
                        35                 40                 45

His Ile Val Glu Pro Lys Gln Ser Ile Asp Gly Phe Pro Lys Gln
                        50                 55                 60

<210> SEQ ID NO 16
<211> LENGTH: 10
<212> TYPE: PRT
<213> ORGANISM: maize
<220> FEATURE:
<221> NAME/KEY: 478..487
<222> LOCATION: REPEAT
<223> OTHER INFORMATION: Sequence of SBE-repeat in DU1.

<400> SEQUENCE: 16

Asp Gln Ser Ile Val Gly Ser His Lys Gln
 1               5                  10

<210> SEQ ID NO 17
<211> LENGTH: 10
<212> TYPE: PRT
<213> ORGANISM: maize
<220> FEATURE:
<221> NAME/KEY: 538..547
<222> LOCATION: REPEAT
<223> OTHER INFORMATION: Sequence of SBE-repeat in DU1.

<400> SEQUENCE: 17

Asp Gln Ser Ile Val Gly Ser Leu Lys Gln
 1               5                  10

<210> SEQ ID NO 18
<211> LENGTH: 10
<212> TYPE: PRT
<213> ORGANISM: maize
<220> FEATURE:
<221> NAME/KEY: 448.457
<222> LOCATION: REPEAT
<223> OTHER INFORMATION: Sequence of SBE-repeat in DU1.

<400> SEQUENCE: 18

Asn Gln Ser Ile Val Gly Ser Cys Lys Gln
```

```
1               5                   10

<210> SEQ ID NO 19
<211> LENGTH: 10
<212> TYPE: PRT
<213> ORGANISM: maize
<220> FEATURE:
<221> NAME/KEY: 568..577
<222> LOCATION: REPEAT
<223> OTHER INFORMATION: Sequence of SBE-repeat in DU1.

<400> SEQUENCE: 19

Asn Gln Ser Ile Val Gly Leu Pro Lys Gln
1               5                   10

<210> SEQ ID NO 20
<211> LENGTH: 10
<212> TYPE: PRT
<213> ORGANISM: maize
<220> FEATURE:
<221> NAME/KEY: 418..427
<222> LOCATION: REPEAT
<223> OTHER INFORMATION: Sequence of SBE-repeat in DU1.

<400> SEQUENCE: 20

Asp Gln Ser Ile Ala Gly Ser His Arg Gln
1               5                   10

<210> SEQ ID NO 21
<211> LENGTH: 10
<212> TYPE: PRT
<213> ORGANISM: maize
<220> FEATURE:
<221> NAME/KEY: 428..437
<222> LOCATION: REPEAT
<223> OTHER INFORMATION: Sequence of SBE-repeat in DU1.

<400> SEQUENCE: 21

Asp Gln Ser Ile Ala Gly Ala Pro Glu Gln
1               5                   10

<210> SEQ ID NO 22
<211> LENGTH: 10
<212> TYPE: PRT
<213> ORGANISM: maize
<220> FEATURE:
<221> NAME/KEY: 404..413
<222> LOCATION: REPEAT
<223> OTHER INFORMATION: Sequence of SBE-repeat in DU1.

<400> SEQUENCE: 22

Asp Lys Ser Ile Val Gly Val Pro Gln Gln
1               5                   10

<210> SEQ ID NO 23
<211> LENGTH: 10
<212> TYPE: PRT
<213> ORGANISM: maize
<220> FEATURE:
<221> NAME/KEY: 598..607
<222> LOCATION: REPEAT
<223> OTHER INFORMATION: Sequence of SBE-repeat in DU1.

<400> SEQUENCE: 23

Asp Leu Ser Ile Val Gly Asn Glu Phe Gln
1               5                   10

<210> SEQ ID NO 24
```

```
<211> LENGTH: 25
<212> TYPE: PRT
<213> ORGANISM: maize
<220> FEATURE:
<221> NAME/KEY: 529..553
<222> LOCATION: REPEAT
<223> OTHER INFORMATION: Conserved M-box sequence in maize SBEI.

<400> SEQUENCE: 24

Lys Cys Ile Ala Tyr Ala Glu Ser His Asp Gln Ser Ile Val Gly
 1               5                  10                  15

Asp Lys Thr Ile Ala Phe Leu Leu Met Asp
                20                  25

<210> SEQ ID NO 25
<211> LENGTH: 25
<212> TYPE: PRT
<213> ORGANISM: pea
<220> FEATURE:
<221> NAME/KEY: 529..553
<222> LOCATION: REPEAT
<223> OTHER INFORMATION: Conserved M-box sequence in pea SBEII.

<400> SEQUENCE: 25

Lys Cys Val Ser Tyr Ala Glu Ser His Asp Gln Ser Ile Val Gly
 1               5                  10                  15

Asp Lys Thr Ile Ala Phe Leu Leu Met Asp
                20                  25

<210> SEQ ID NO 26
<211> LENGTH: 25
<212> TYPE: PRT
<213> ORGANISM: wheat
<220> FEATURE:
<221> NAME/KEY: 529..553
<222> LOCATION: REPEAT
<223> OTHER INFORMATION: Conserved M-box sequence in wheat SBEI.

<400> SEQUENCE: 26

Lys Cys Ile Ala Tyr Ala Glu Ser His Asp Gln Ser Ile Val Gly
 1               5                  10                  15

Asp Lys Thr Met Ala Phe Leu Leu Met Asp
                20                  25

<210> SEQ ID NO 27
<211> LENGTH: 25
<212> TYPE: PRT
<213> ORGANISM: maize
<220> FEATURE:
<221> NAME/KEY: 572..596
<222> LOCATION: REPEAT
<223> OTHER INFORMATION: Conserved M-box sequence in maize SBEIa.

<400> SEQUENCE: 27

Lys Cys Val Thr Tyr Cys Glu Ser His Asp Gln Ala Leu Val Gly
 1               5                  10                  15

Asp Lys Thr Ile Ala Phe Trp Leu Met Asp
                20                  25

<210> SEQ ID NO 28
<211> LENGTH: 15
<212> TYPE: PRT
<213> ORGANISM: maize
<220> FEATURE:
<221> NAME/KEY: 572..596
<222> LOCATION: REPEAT
<223> OTHER INFORMATION: Conserved M-box sequence in maize SBEIIb.
```

```
<400> SEQUENCE: 28

Lys Cys Val Thr Tyr Ala Glu Ser His Asp Gln Ala Leu Val Gly
 1               5                  10                  15

<210> SEQ ID NO 29
<211> LENGTH: 25
<212> TYPE: PRT
<213> ORGANISM: pea
<220> FEATURE:
<221> NAME/KEY: 572..596
<222> LOCATION: REPEAT
<223> OTHER INFORMATION: Conserved M-box sequence in pea SBEI.

<400> SEQUENCE: 29

Lys Cys Val Val Tyr Cys Glu Ser His Asp Gln Ala Leu Val Gly
 1               5                  10                  15

Asp Lys Thr Met Ala Phe Leu Leu Met Asp
                20                  25

<210> SEQ ID NO 30
<211> LENGTH: 25
<212> TYPE: PRT
<213> ORGANISM: yeast
<220> FEATURE:
<221> NAME/KEY: 477..501
<222> LOCATION: REPEAT
<223> OTHER INFORMATION: Conserved M-box sequence in yeast GLC3 glycogen
      synthase.

<400> SEQUENCE: 30

Lys Val Val Ala Tyr Cys Glu Ser His Asp Gln Ala Leu Val Gly
 1               5                  10                  15

Asp Lys Ser Leu Ala Phe Trp Leu Met Asp
                20                  25

<210> SEQ ID NO 31
<211> LENGTH: 25
<212> TYPE: PRT
<213> ORGANISM: Homo sapiens
<220> FEATURE:
<221> NAME/KEY: 477..501
<222> LOCATION: REPEAT
<223> OTHER INFORMATION: Conserved M-box sequence in human liver
      glycogen synthase.

<400> SEQUENCE: 31

Lys Cys Ile Ala Tyr Ala Glu Ser His Asp Gln Ala Leu Val Gly
 1               5                  10                  15

Asp Lys Thr Leu Ala Phe Trp Leu Met Asp
                20                  25

<210> SEQ ID NO 32
<211> LENGTH: 28
<212> TYPE: PRT
<213> ORGANISM: maize
<220> FEATURE:
<221> NAME/KEY: 150..177
<222> LOCATION: REPEAT
<223> OTHER INFORMATION: Second 28 amino acid residue repeat of 85
      residue repeat in N-terminus of DU1.

<400> SEQUENCE: 32

Glu Thr Val Asp Glu Ala Glu Val Glu Glu Asp Lys Phe Glu Val
 1               5                  10                  15

Asp Thr Ser Gly Ile Val Leu Arg Asn Val Ala Val Arg
```

<210> SEQ ID NO 33
<211> LENGTH: 29
<212> TYPE: PRT
<213> ORGANISM: artificial sequence
<220> FEATURE:
<221> NAME/KEY: 178..205
<222> LOCATION: REPEAT
<223> OTHER INFORMATION: Second 28 amino acid residue repeat of 85 residue repeat in N-terminus of DU1.

<400> SEQUENCE: 33

Glu Val Asp Pro Lys Asp Glu His Asn Ala Lys Asp Val Phe Val
 1               5                  10                  15

Val Asp Ser Ser Gly Thr Ala Pro Asp Asn Ala Ala Val Glu
                20                  25

<210> SEQ ID NO 34
<211> LENGTH: 27
<212> TYPE: PRT
<213> ORGANISM: maize
<220> FEATURE:
<221> NAME/KEY: 206..233
<222> LOCATION: REPEAT
<223> OTHER INFORMATION: Third 28 amino acid residue repeat of 85 residue repeat in N-terminus of DU1.

<400> SEQUENCE: 34

Glu Val Val Asp Glu Ala Glu Val Glu Glu Asp Met Val Asp Val
 1               5                  10                  15

Asp Ile Leu Gly Leu Asp Leu Asn Asn Ala Thr Ile
                20                  25

<210> SEQ ID NO 35
<211> LENGTH: 1230
<212> TYPE: PRT
<213> ORGANISM: potato
<220> FEATURE:
<223> OTHER INFORMATION: Deduced amino acid sequence of potato starch synthase SSIII.

<400> SEQUENCE: 35

Met Asp Val Pro Phe Pro Leu His Arg Ser Leu Ser Cys Thr Ser
 1               5                  10                  15

Val Ser Asn Ala Ile Thr His Leu Lys Ile Lys Pro Ile Leu Gly
                20                  25                  30

Phe Val Ser His Gly Thr Thr Ser Leu Ser Val Gln Ser Ser Ser
                35                  40                  45

Trp Arg Lys Asp Gly Met Val Thr Gly Val Ser Phe Ser Ile Cys
                50                  55                  60

Ala Asn Phe Ser Gly Arg Arg Arg Lys Val Ser Thr Pro Arg
                65                  70                  75

Ser Gln Gly Ser Ser Pro Lys Gly Phe Val Pro Arg Lys Pro Ser
                80                  85                  90

Gly Met Ser Thr Gln Arg Lys Val Gln Lys Ser Asn Gly Asp Lys
                95                  100                 105

Glu Ser Lys Ser Thr Ser Thr Ser Lys Glu Ser Glu Ile Ser Asn
                110                 115                 120

Gln Lys Thr Val Glu Ala Arg Val Glu Thr Ser Asp Asp Thr
                125                 130                 135

Lys Gly Val Val Arg Asp His Lys Phe Leu Glu Asp Glu Asp Glu

```
                    140                 145                 150
Ile Asn Gly Ser Thr Lys Ser Ile Ser Met Ser Pro Val Arg Val
                155                 160                 165
Ser Ser Gln Phe Val Glu Ser Glu Thr Gly Gly Asp Asp Lys
            170                 175                 180
Asp Ala Val Lys Leu Asn Lys Ser Lys Arg Ser Glu Glu Ser Gly
                185                 190                 195
Phe Ile Ile Asp Ser Val Ile Arg Glu Gln Ser Gly Ser Gln Gly
                200                 205                 210
Glu Thr Asn Ala Ser Ser Lys Gly Ser His Ala Val Gly Thr Lys
                215                 220                 225
Leu Tyr Glu Ile Leu Gln Val Asp Val Glu Pro Gln Gln Leu Lys
                230                 235                 240
Glu Asn Asn Ala Gly Asn Val Glu Tyr Lys Gly Pro Val Ala Ser
                245                 250                 255
Lys Leu Leu Glu Ile Thr Lys Ala Ser Asp Val Glu His Thr Glu
                260                 265                 270
Ser Asn Glu Ile Asp Asp Leu Asp Thr Asn Ser Phe Phe Lys Ser
                275                 280                 285
Asp Leu Ile Glu Glu Asp Glu Pro Leu Ala Ala Gly Thr Val Glu
                290                 295                 300
Thr Gly Asp Ser Ser Leu Asn Leu Arg Leu Glu Met Glu Ala Asn
                305                 310                 315
Leu Arg Arg Gln Ala Ile Glu Arg Leu Ala Glu Glu Asn Leu Leu
                320                 325                 330
Gln Gly Ile Arg Leu Phe Cys Phe Pro Glu Val Val Lys Pro Asp
                335                 340                 345
Glu Asp Val Glu Ile Phe Leu Asn Arg Gly Leu Ser Thr Leu Lys
                350                 355                 360
Asn Glu Ser Asp Val Leu Ile Met Gly Ala Phe Asn Glu Trp Arg
                365                 370                 375
Tyr Arg Ser Phe Thr Thr Arg Leu Thr Glu Thr His Leu Asn Gly
                380                 385                 390
Asp Trp Trp Ser Cys Lys Ile His Val Pro Lys Glu Ala Tyr Arg
                395                 400                 405
Ala Asp Phe Val Phe Phe Asn Gly Gln Asp Val Tyr Asp Asn Asn
                410                 415                 420
Asp Gly Asn Asp Phe Ser Ile Thr Val Lys Gly Gly Met Gln Ile
                425                 430                 435
Ile Asp Phe Glu Asn Phe Leu Leu Glu Glu Lys Trp Arg Glu Gln
                440                 445                 450
Glu Lys Leu Ala Lys Glu Gln Ala Glu Arg Glu Arg Leu Ala Glu
                455                 460                 465
Glu Gln Arg Arg Ile Glu Ala Glu Lys Ala Glu Ile Glu Ala Asp
                470                 475                 480
Arg Ala Gln Ala Lys Glu Glu Ala Ala Lys Lys Lys Val Leu
                485                 490                 495
Arg Glu Leu Met Val Lys Ala Thr Lys Thr Arg Asp Ile Thr Trp
                500                 505                 510
Tyr Ile Glu Pro Ser Glu Phe Lys Cys Glu Asp Lys Val Arg Leu
                515                 520                 525
Tyr Tyr Asn Lys Ser Ser Gly Pro Leu Ser His Ala Lys Asp Leu
                530                 535                 540
```

-continued

```
Trp Ile His Gly Gly Tyr Asn Asn Trp Lys Asp Gly Leu Ser Ile
            545                 550                 555
Val Lys Lys Leu Val Lys Ser Glu Arg Ile Asp Gly Asp Trp Trp
            560                 565                 570
Tyr Thr Glu Val Val Ile Pro Asp Gln Ala Leu Phe Leu Asp Trp
            575                 580                 585
Val Phe Ala Asp Gly Pro Pro Lys His Ala Ile Ala Tyr Asp Asn
            590                 595                 600
Asn His Arg Gln Asp Phe His Ala Ile Val Pro Asn His Ile Pro
            605                 610                 615
Glu Glu Leu Tyr Trp Val Glu Glu His Gln Ile Phe Lys Thr
            620                 625                 630
Leu Gln Glu Glu Arg Arg Leu Arg Glu Ala Ala Met Arg Ala Lys
            635                 640                 645
Val Glu Lys Thr Ala Leu Leu Lys Thr Glu Thr Lys Glu Arg Thr
            650                 655                 660
Met Lys Ser Phe Leu Leu Ser Gln Lys His Val Val Tyr Thr Glu
            665                 670                 675
Pro Leu Asp Ile Gln Ala Gly Ser Ser Val Thr Val Tyr Tyr Asn
            680                 685                 690
Pro Ala Asn Thr Val Leu Asn Gly Lys Pro Glu Ile Trp Phe Arg
            695                 700                 705
Cys Ser Phe Asn Arg Trp Thr His Arg Leu Gly Pro Leu Pro Pro
            710                 715                 720
Gln Lys Met Ser Pro Ala Glu Asn Gly Thr His Val Arg Ala Thr
            725                 730                 735
Val Lys Val Pro Leu Asp Ala Tyr Met Met Asp Phe Val Phe Ser
            740                 745                 750
Glu Arg Glu Asp Gly Gly Ile Phe Asp Asn Lys Ser Gly Met Asp
            755                 760                 765
Tyr His Ile Pro Val Phe Gly Gly Val Ala Lys Glu Pro Pro Met
            770                 775                 780
His Ile Val His Ile Ala Val Glu Met Ala Pro Ile Ala Lys Val
            785                 790                 795
Gly Gly Leu Gly Asp Val Val Thr Ser Leu Ser Arg Ala Val Gln
            800                 805                 810
Asp Leu Asn His Asn Val Asp Ile Ile Leu Pro Lys Tyr Asp Cys
            815                 820                 825
Leu Lys Met Asn Asn Val Lys Asp Phe Arg Phe His Lys Asn Tyr
            830                 835                 840
Phe Trp Gly Gly Thr Glu Ile Lys Val Trp Phe Gly Lys Val Glu
            845                 850                 855
Gly Leu Ser Val Tyr Phe Leu Glu Pro Gln Asn Gly Leu Phe Ser
            860                 865                 870
Lys Gly Cys Val Tyr Gly Cys Ser Asn Asp Gly Glu Arg Phe Gly
            875                 880                 885
Phe Phe Cys His Ala Ala Leu Glu Phe Leu Leu Gln Gly Gly Phe
            890                 895                 900
Ser Pro Asp Ile Ile His Cys His Asp Trp Ser Ser Ala Pro Val
            905                 910                 915
Ala Trp Leu Phe Lys Glu Gln Tyr Thr His Tyr Gly Leu Ser Lys
            920                 925                 930
```

```
Ser Arg Ile Val Phe Thr Ile His Asn Leu Glu Phe Gly Ala Asp
            935                 940                 945

Leu Ile Gly Arg Ala Met Thr Asn Ala Asp Lys Ala Thr Thr Val
            950                 955                 960

Ser Pro Thr Tyr Ser Gln Glu Val Ser Gly Asn Pro Val Ile Ala
            965                 970                 975

Pro His Leu His Lys Phe His Gly Ile Val Asn Gly Ile Asp Pro
            980                 985                 990

Asp Ile Trp Asp Pro Leu Asn Asp Lys Phe Ile Pro Ile Pro Tyr
            995                1000                1005

Thr Ser Glu Asn Val Val Glu Gly Lys Thr Ala Ala Lys Glu Ala
           1010                1015                1020

Leu Gln Arg Lys Leu Gly Leu Lys Gln Ala Asp Leu Pro Leu Val
           1025                1030                1035

Gly Ile Ile Thr Arg Leu Thr His Gln Lys Gly Ile His Leu Ile
           1040                1045                1050

Lys His Ala Ile Trp Arg Thr Leu Glu Arg Asn Gly Gln Val Val
           1055                1060                1065

Leu Leu Gly Ser Ala Pro Asp Pro Arg Val Gln Asn Asn Phe Val
           1070                1075                1080

Asn Leu Ala Asn Gln Leu His Ser Lys Tyr Asn Asp Arg Ala Arg
           1085                1090                1095

Leu Cys Leu Thr Tyr Asp Glu Pro Leu Ser His Leu Ile Tyr Ala
           1100                1105                1110

Gly Ala Asp Phe Ile Leu Val Pro Ser Ile Phe Glu Pro Cys Gly
           1115                1120                1125

Leu Thr Gln Leu Thr Ala Met Arg Tyr Gly Ser Ile Pro Val Val
           1130                1135                1140

Arg Lys Thr Gly Gly Leu Tyr Asp Thr Val Phe Asp Val Asp His
           1145                1150                1155

Asp Lys Glu Arg Ala Gln Gln Cys Gly Leu Glu Pro Asn Gly Phe
           1160                1165                1170

Ser Phe Asp Gly Ala Asp Ala Gly Gly Val Asp Tyr Ala Leu Asn
           1175                1180                1185

Arg Ala Leu Ser Ala Trp Tyr Asp Gly Arg Asp Trp Phe Asn Ser
           1190                1195                1200

Leu Cys Lys Gln Val Met Glu Gln Asp Trp Ser Trp Asn Arg Pro
           1205                1210                1215

Ala Leu Asp Tyr Leu Glu Leu Tyr His Ala Ala Arg Lys Leu Glu
           1220                1225                1230

<210> SEQ ID NO 36
<211> LENGTH: 9
<212> TYPE: DNA
<213> ORGANISM: artificial sequence
<220> FEATURE:
<222> LOCATION: repeat_unit
<223> OTHER INFORMATION: Sequence of the nine base pair direct repeats
      flanking a Mu1 element in cloned fragment.

<400> SEQUENCE: 36 gtgagaatg                                                              9

<210> SEQ ID NO 37
<211> LENGTH: 32
<212> TYPE: DNA
<213> ORGANISM: artificial sequence
```

-continued

```
<220> FEATURE:
<221> NAME/KEY: primer
<223> OTHER INFORMATION: Primer containing restriction sites

<400> SEQUENCE: 37
aaacccggga attcgatgga gatggtccta cg                                           32
```

What is claimed is:

1. A method of producing starch, said method comprising the steps of:

transforming a cell with an expression vector comprising an isolated nucleic acid molecule having the sequence shown in SEQ ID No. 1 encoding a starch synthase enzyme from maize, operably linked to elements that allow expression of said nucleic acid molecule; and extracting and purifying said starch.

2. An isolated nucleic acid molecule comprising a nucleotide sequence selected from the group consisting of:

nt 120 to nt 1221 of SEQ ID No. 1; nt 655 to nt 1221 of SEQ ID No. 1; nt 565 to nt 816 of SEQ ID No. 1; nt 1369 to nt 1944 of SEQ ID No. 1; nt 1 to nt 1437 of SEQ ID No. 1; nt 1438 to nt 2424 of SEQ ID No. 1; and nt 2425 to nt 3791 of SEQ ID No. 1, said isolated nucleic acid molecule encoding a starch synthase enzyme.

3. A method of producing starch, said method comprising the steps of:

transforming a cell with an expression vector comprising the nucleic acid molecule of claim 2, operably linked to elements that allow expression of said nucleic acid molecule; and extracting and purifying said starch.

4. The method of claim or claim 1 or claim 3, wherein the cell carries an additional mutation in a gene involved in a pathway selected from the group consisting of starch synthesis, starch metabolism, glucose synthesis, glucose metabolism, glycogen synthesis, glycogen metabolism, carbohydrate synthesis and carbohydrate metabolism.

5. An isolated nucleic acid molecule having a nucleotide sequence selected from the group consisting of:

nt 120 to nt 1221 of SEQ ID No. 1; nt 655 to nt 1221 of SEQ ID No. 1; nt 565 to nt 816 of SEQ ID No. 1; nt 1369 to nt 1944 of SEQ ID No. 1; nt 1 to nt 1437 of SEQ ID No. 1; nt 1438 to nt 2424 of SEQ ID No. 1; and nt 2425 to nt 3791 of SEQ ID No. 1.

6. An expression vector comprising the nucleic acid molecule of claim 2 or claim 5, operably linked to elements that allow expression of said nucleic acid molecule.

7. A host cell transfected with the vector of claim 6.

8. A transgenic plant comprising the vector of claim 6.

9. A fusion construct, comprising the isolated nucleic acid molecule of claim 5 fused to nucleic acid encoding an affinity purification peptide.

* * * * *

UNITED STATES PATENT AND TRADEMARK OFFICE
CERTIFICATE OF CORRECTION

PATENT NO. : 6,639,125 B1
DATED : October 28, 2003
INVENTOR(S) : Alan M. Myers et al.

It is certified that error appears in the above-identified patent and that said Letters Patent is hereby corrected as shown below:

Column 7,
Line 56, "mg-" should read -- $mg^{-1}$ --;

Column 9,
Line 53, "a n" should read -- an --;
Line 62, "b e" should read -- be --;

Column 10,
Line 66, "a n" should read -- an --;

Column 11,
Lines 19, 61 and 67, "b e" should read -- be --;
Line 36, "i n" should read -- in --;

Column 12,
Line 22, "o r" should read -- or --;
Line 41, "a n" should read -- an --;

Column 13,
Line 7, "n t 655" should read -- nt 655 --;

Column 14,
Line 46, "a n" should read -- an --;

Column 15,
Line 33, "λXZAPII-express" should read -- λZAPII-express --;
Line 39, "GTACAATGACAACIATCCC-3')" should read
-- GTACAATGACAACTTTATCCC-3') --;

Column 16,
Line 29, "λXgt11" should read -- λgt11 --;
Line 43, "5-101" should read -- 5-10 µ1 --;

UNITED STATES PATENT AND TRADEMARK OFFICE
CERTIFICATE OF CORRECTION

PATENT NO.     : 6,639,125 B1
DATED          : October 28, 2003
INVENTOR(S)    : Alan M. Myers et al.

It is certified that error appears in the above-identified patent and that said Letters Patent is hereby corrected as shown below:

Column 29,
Lines 38-47, delete paragraph (second occurrence);

Column 30,
Lines 2 and 31, "anti-DU1.N" should read -- anti-DU1N --;
Line 22, "Lo" should read -- to --;

Column 32,
Line 13, "SSI" should read -- SSII --; and

Column 34,
Line 34, "b e" should read -- be --.

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,639,125 B1
DATED : October 28, 2003
INVENTOR(S) : Alan M. Myers et al.

It is certified that error appears in the above-identified patent and that said Letters Patent is hereby corrected as shown below:

Column 7,
Line 56, "mg-" should read -- $mg^{-1}$ --;

Column 9,
Line 53, "a n" should read -- an --;
Line 62, "b e" should read -- be --;

Column 10,
Line 66, "a n" should read -- an --;

Column 11,
Lines 19, 61 and 67, "b e" should read -- be --;
Line 36, "i n" should read -- in --;
Line 22, "a n" should read -- an --;

Column 12,
Line 22, "o r" should read -- or --;
Line 41, "a n" should read -- an --;

Column 13,
Line 7, "n t 655" should read -- nt 655 --;

Column 14,
Line 46, "a n" should read -- an --;

Column 15,
Line 33, "λXZAPII-express" should read -- λZAPII-express --;
Line 39, "GTACAATGACAACIATCCC-3')" should read
-- GTACAATGACAACTTTATCCC-3') --;

Column 16,
Line 29, "λXgt11" should read -- λgt11 --;
Line 43, "5-101" should read -- 5-10 μl --;

UNITED STATES PATENT AND TRADEMARK OFFICE
CERTIFICATE OF CORRECTION

PATENT NO.   : 6,639,125 B1
DATED        : October 28, 2003
INVENTOR(S)  : Alan M. Myers et al.

It is certified that error appears in the above-identified patent and that said Letters Patent is hereby corrected as shown below:

Column 29,
Lines 38-47, delete paragraph (second occurrence);

Column 30,
Lines 2 and 31, "anti-DU1.N" should read -- anti-DU1N --;
Line 22, "Lo" should read -- to --;

Column 32,
Line 13, "SSI" should read -- SSII --; and

Column 34,
Line 34, "b e" should read -- be --.

This certificate supersedes Certificate of Correction issued September 28, 2004.

Signed and Sealed this

Sixteenth Day of November, 2004

JON W. DUDAS
*Director of the United States Patent and Trademark Office*